(12) United States Patent
Shen et al.

(10) Patent No.: US 8,987,284 B2
(45) Date of Patent: Mar. 24, 2015

(54) PHOSPHORUS CONTAINING QUINAZOLINE COMPOUNDS AND METHODS OF USE

(75) Inventors: Wang Shen, San Mateo, CA (US); Aimin Zhang, Castro Valley, CA (US); Junfa Fan, Hayward, CA (US); Xiaoling Zheng, Fremont, CA (US)

(73) Assignee: Newgen Therapeutics, Inc., Menlo Park, CA (US)

( * ) Notice: Subject to any disclaimer, the term of this patent is extended or adjusted under 35 U.S.C. 154(b) by 115 days.

(21) Appl. No.: 13/380,808

(22) PCT Filed: Jul. 2, 2010

(86) PCT No.: PCT/US2010/001897
§ 371 (c)(1),
(2), (4) Date: Apr. 10, 2012

(87) PCT Pub. No.: WO2011/002523
PCT Pub. Date: Jan. 6, 2011

(65) Prior Publication Data
US 2012/0196833 A1    Aug. 2, 2012

Related U.S. Application Data

(60) Provisional application No. 61/222,551, filed on Jul. 2, 2009.

(51) Int. Cl.
| | |
|---|---|
| *A01N 43/54* | (2006.01) |
| *A61K 31/517* | (2006.01) |
| *C07D 239/72* | (2006.01) |
| *C07D 401/00* | (2006.01) |
| *C07F 9/6512* | (2006.01) |
| *C07F 9/6558* | (2006.01) |
| *C07F 9/6568* | (2006.01) |
| *C07F 9/6571* | (2006.01) |

(52) U.S. Cl.
CPC ......... *C07F 9/65685* (2013.01); *C07F 9/65128* (2013.01); *C07F 9/65586* (2013.01); *C07F 9/657181* (2013.01)
USPC ..................... 514/266.1; 514/266.2; 544/283; 544/284

(58) Field of Classification Search
USPC ..................... 514/266.1, 266.2; 544/283, 284
See application file for complete search history.

(56) References Cited

U.S. PATENT DOCUMENTS

| | | | |
|---|---|---|---|
| 6,391,874 | B1 | 5/2002 | Cockerill et al. |
| 6,894,057 | B2 | 5/2005 | Gaudilliere et al. |
| 2005/0107358 | A1 | 5/2005 | Himmelsbach et al. |
| 2006/0115815 | A1 | 6/2006 | Birkus et al. |
| 2008/0039426 | A1 | 2/2008 | Jankowski et al. |
| 2008/0234267 | A1 | 9/2008 | Lackey |

FOREIGN PATENT DOCUMENTS

| | | |
|---|---|---|
| CA | 2516426 A1 | 9/2004 |
| CA | 2541928 A1 | 4/2005 |
| CN | 1751033 A | 3/2006 |
| CN | 1867564 A | 11/2006 |
| JP | 2002-539199 A | 11/2002 |
| JP | 2006-508979 A | 3/2006 |
| JP | 2007-510667 A | 4/2007 |
| JP | 2007-532658 A | 11/2007 |
| JP | 2009-523724 A | 6/2009 |
| WO | WO-00/51991 A1 | 9/2000 |
| WO | WO-00/55141 A1 | 9/2000 |
| WO | WO-01/04111 A1 | 1/2001 |
| WO | WO-03/089439 A1 | 10/2003 |
| WO | WO-2004/046101 A2 | 6/2004 |
| WO | WO-2004/046101 A3 | 6/2004 |
| WO | WO-2005/037824 A2 | 4/2005 |
| WO | WO-2005/046678 A1 | 5/2005 |
| WO | 2005/105094 * | 11/2005 |
| WO | WO-2005/105094 A2 | 11/2005 |
| WO | WO-2007/085638 A1 | 8/2007 |
| WO | WO-2007/087068 A2 | 8/2007 |
| WO | WO-2007/087068 A3 | 8/2007 |
| WO | WO-2011/002523 A1 | 1/2011 |

OTHER PUBLICATIONS

Vippagunta et al (2000).*
McMahon et al (2001).*
Pinedo et al (2001).*
Baselga, J. et al. (Jul. 2009, e-pub. Jun. 18, 2009). "Novel Anticancer Targets: Revisiting ERBB2 and Discovering ERBB3," *Nature Review of Cancer* 9(7):463-475.
Burgess, A.W. (Oct. 2008). "EGFR Family: Structure Physiology Signalling and Therapeutic Targets," *Growth Factors* 26(5):263-274.
European Search Report mailed on Mar. 7, 2013, for European Patent Application No. 10794499.3 filed on Jul. 2, 2010, four pages.
Hynes, N.E. et al. (Aug. 8, 1994). "The Biology of erbB-2/neu/HER-2 and Its Role In Cancer," *Biochimica et Biophysica Acta* 1198:165-184.
Klapper, L.N. et al. (2000). "Biochemical and Clinical Implications of the ErbB/HER Signaling Network of Growth Factor Receptors," *Advanced Cancer Research* 77:25-79.

(Continued)

*Primary Examiner* — Paul V. Ward
(74) *Attorney, Agent, or Firm* — Morrison & Foerster LLP

(57) ABSTRACT

Disclosed are novel quinazoline derivatives containing phosphorus substitutions and methods for the treatment of hyperproliferative diseases (e.g. cancer) using the compounds. These compounds are type I receptor protein kinase inhibitors useful in treating disorders related to abnormal protein kinase activities such as cancer and inflammation in mammals. Also disclosed are pharmaceutical compositions containing the compounds, methods for the preparation of the compounds and their pharmaceutically acceptable salts.

24 Claims, 2 Drawing Sheets

(56) References Cited

OTHER PUBLICATIONS

Lemmon, M.A. (2009, e-pub. Oct. 31, 2008). "Ligand-Induced ErbB Receptor Dimerization," *Experimental Cell Research* 315:638-648.

Maier, L. (1990). "Organic Phosphorus Compounds 91. Synthesis and Properties of 1-Amino-2-Arylethylphosphonic and Phosphinic Acids As Well As Phosphine Oxides," *Phosphorus, Sulfur and Silicon and the Related Elements* 53(1-4):43-67.

Mastalerz, H. et al. (2007, e-pub. Jun. 10, 2007). "5-((4-Aminopiperidin-1-yl)methyl)pyrrolotriazine Dual Inhibitors of EGFR and HER2 Protein Tyrosine Kinases," *Bioorganic Medicinal Chemistry Letters* 17:4947-4954.

Mendelsohn, J. et al. (2000). "The EGF Receptor Family As Targets for Cancer Therapy," *Oncogene* 19:6550-6565.

Milanezi, F. et al. (2008). "EGFR/HER2 In Breast Cancer: A Biological Approach For Molecular Diagnosis And Therapy," *Expert Review Molecule Diagnosis* 8(4):417-434.

O'Donovan, N. et al. (2007). "EGFR And HER-2 Antagonists In Breast Cancer," *Anticancer Res.* 27(3A):1285-1294.

Salomon, D.S. et al. (1995). "Epidermal Growth Factor-Related Peptides and Their Receptors in Human Malignancies," *Critical Reviews in Oncology and Hematology* 19:183-232.

Tai, W. et al. (Sep. 15, 2010). "The Role of HER2 in Cancer Therapy and Targeted Drug Delivery," *J Control Release* 146(3):264-275, 28 pages.

* cited by examiner

PHOSPHORUS CONTAINING QUINAZOLINE COMPOUNDS AND METHODS OF USE

CROSS-REFERENCE TO RELATED APPLICATIONS

This application is a National Phase application under 35 U.S.C. §371 of International Application No. PCT/US2010/001897 filed Jul. 2, 2010 and claims priority benefit of U.S. provisional patent application Ser. No. 61/222,551 filed Jul. 2, 2009, the disclosure of which are incorporated herein by reference in their entirety.

FIELD OF INVENTION

The invention relates to novel quinazoline derivatives containing phosphorus substitutions as type I receptor protein kinase inhibitors. These inhibitors are useful in treating disorders related to abnormal protein kinase activities such as cancer and inflammation in mammals. The invention relates to the pharmaceutical composition containing these inhibitors, methods for the preparation of these inhibitors and their pharmaceutically acceptable salts.

BACKGROUND OF THE INVENTION

The type I receptor tyrosine kinase family is comprised of four closely related receptors: ErbB1 (EFGR or HER1), ErbB2 (HER2), ErbB3 (HER) and ErbB4 (HER4). These receptors are transmembrane glycoproteins which contain an extracellular domain for ligand binding and, with the exception of HER3, an intracellular catalytically active tyrosine kinase domain. These receptors transmit extracellular signals through the cytosol via a signal transduction cascade to the nucleus. The extracellular signal is transmitted by ligand binding to the dimeric receptor, with the exception of erbB2, of which a high affinity soluble ligand has yet to be identified. After ligand binding, the type I receptor tyrosine kinases either homodimerize or heterodimerize with another member of the subfamily of receptors (Lemmon M A, Experimental Cell Research (2009), 315, 638-648). ErbB2 participates in this process by heterodimerization. In fact, it has been shown that ErbB2 is the preferred heterodimerization partner (Mehelsohn Oncogene 2000). Dimerization leads to activation of the ErbB receptors by autophosphorylation of the intracellular domain. This autophosphorylation recruits adaptor proteins and leads to a phosphorylation cascade that transmits the signal throughout the cell. The type I receptor tyrosine kinase family (ErbB family) signals through the ras/raf/MEK/MAPK pathway as well as the PI3K/Akt pathway. These signaling pathways lead to both cell proliferation and cell survival through inhibition of apoptosis.

It has been demonstrated that ErbB family receptors play important roles in cancer (Burgess A W, Growth Factors (2008), 26(5), 263-74). Squamous carcinomas of the head and neck, and lung express high levels of EGFR. Also, constitutively active EGFR has been found in gliomas, breast cancer and lung cancer (Salomon, et al., Critical Review Oncology/Hematology (1995), 19, 183-232; Klapper, et al., Advanced Cancer Research (2000), 77, 25-79, and Hynes and Stem, *Biochimica et Biophysica Acta* (1994), 1198, 165-184). ErbB2 overexpression occurs in approximately 30% of all breast cancer (Milanezi, et al., Expert Review Molecule Diagnosis. (2008), 8(4), 417-34). It has been also implicated in other human cancers including colon, ovary, bladder, stomach, esophagus, lung, uterus and prostate. ErbB2 overexpression has also been correlated with poor prognosis in human cancer, including metastasis, and early relapses (Baselga J and Swain S M, Nature Review of Cancer (2009), 9(7), 463-75)

The type I tyrosine kinase receptor family has been an active area of anti-cancer research (O'Donovan and Crown *Anticancer Res.* (2007) 27(3A), 1285-94). Although several inhibitors of the EGFR and the ErbB2 signaling pathway have demonstrated clinical efficacy in cancer treatment and a few molecules have been approved by the FDA, due to the prevalence and complexity of cancers, there remains a need for better treatment for cancers such as small molecule pharmaceuticals with better pharmacological properties and/or lower toxcitiy.

BRIEF SUMMARY OF THE INVENTION

This invention provides for phosphorus substituted 4-anilino quinazolines of Formula I, and pharmaceutically acceptable salts and prodrugs thereof, that are useful in the treatment of hyperproliferative diseases, such as cancer. Specifically, the present invention relates to compounds of Formula I that act as EGFR and ErbB2 inhibitors. Also provided are formulations containing compounds of Formula I and methods of using the compounds to treat a patient in need thereof. In addition, there are described processes for preparing the inhibitory compounds of Formula (I), or Formula (A).

In one aspect, provided is a compound of Formula (A):

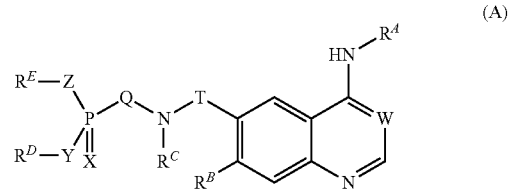

(A)

wherein:

W is N or a C—CN group;

$R^A$ is a substituted monocyclic, bicyclic or tricyclic aryl or heteroaryl moiety, or an arylalkyl group;

$R^B$ is hydrogen, halogen, cyano, nitro, trifluoromethyl, difluoromethyl, trifluoromethoxy, difluoromethoxy, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkylalkyl, heterocyclyl, heterocyclylalkyl, —$NR^1SO_2R^2$, —$SO_2NR^1R^3$, —$C(O)R^4$, —$C(O)OR^5$, —$OC(O)R^4$, —$NR^1C(O)OR^5$, —$NR^1C(O)R^4$, —$C(O)NR^1R^3$, —$NR^1R^3$, —$NR^1C(O)NR^1R^3$, —$OR^5$, —$S(O)R^2$, —$SO_2R^2$ or —$SR^2$, wherein each said alkyl, alkenyl, alkynyl, cycloalkyl, cycloalkylalkyl, heterocyclyl and heterocyclylalkyl is unsubstituted or optionally substituted with up to five groups independently selected from the group consisting of oxo, halogen, $C_1$-$C_6$ alkyl, $C_2$-$C_6$ alkenyl, $C_2$-$C_6$ alkynyl, $C_3$-$C_8$ cycloalkyl, $C_3$-$C_8$ cycloalkylalkyl, cyano, trifluoromethyl, difluoromethoxy, trifluoromethoxy, azido, —$NR^{11}SO_2R^{12}$, —$SO_2NR^{11}R^{13}$, —$C(O)R^{14}$, —$C(O)OR^{15}$, —$OC(O)R^{14}$, —$NR^{11}C(O)OR^{16}$, —$NR^{11}C(O)R^{14}$, —$C(O)NR^{11}R^{13}$, —$NR^{11}R^{13}$, —$NR^{11}C(O)NR^{11}R^{13}$, —$OR^{15}$, —$S(O)R^{12}$, —$SO_2R^{12}$, —$SR^{12}$, heterocyclyl and heterocyclylalkyl;

T is a bond or a divalent radical formed by removing an additional hydrogen atom from a $C_1$-$C_6$ alkyl, $C_2$-$C_6$ alkenyl, $C_2$-$C_6$ alkynyl, $C_3$-$C_8$ cycloalkyl, $C_3$-$C_8$ cycloalkylalkyl, aryl, arylalkyl, heteroaryl, heteroarylalkyl, heterocyclyl or heterocyclylalkyl; wherein each said alkyl, alkenyl, alkynyl, cycloalkyl, aryl, heteroaryl and heterocyclyl is unsubstituted or optionally substituted with up to three groups independently selected from the group consisting of oxo, halogen, $C_1$-$C_3$ alkyl, $C_2$-$C_3$ alkenyl, $C_2$-$C_3$ alkynyl, cyano, trifluoromethyl, difluoromethoxy, trifluoromethoxy, azido, —$NR^{11}SO_2R^{12}$, —$SO_2NR^{11}R^{13}$, —$C(O)R^{14}$, —$C(O)OR^{15}$, —$OC(O)R^{14}$, —$NR^{11}C(O)OR^{15}$, —$NR^{11}C(O)R^{14}$, —$C(O)NR^{11}R^{13}$, —$NR^{11}R^{13}$, —$NR^{11}C(O)NR^{11}R^{13}$, —$OR^{15}$, —$S(O)R^{12}$, —$SO_2R^{12}$ and —$SR^{12}$;

Q is a bond or $C_1$-$C_6$ alkyl, wherein said alkyl is unsubstituted or optionally substituted with up to three groups independently selected from the group consisting of oxo, halogen, $C_1$-$C_3$ alkyl, cyano, trifluoromethyl, difluoromethoxy, trifluoromethoxy, —$NR^{11}R^{13}$ and —$OR^{15}$;

X is O or S;

Y and Z are independently O, S, $NR^1$ or a bond;

$R^C$ is H, $C_1$-$C_6$ alkyl, $C_3$-$C_6$ cycloalkyl, —$SO_2NR^3R^1$, —$C(O)R^4$, —$C(O)OR^5$, —$C(O)NR^1R^3$, or —$SO_2R^2$, wherein each said alkyl and cycloalkyl is unsubstituted or optionally substituted with up to five groups independently selected from the group consisting of oxo, halogen, cyano, azido and —$OR^{15}$;

$R^D$ is $C_1$-$C_8$ alkyl, $C_3$-$C_8$ cycloalkyl, aryl, arylalkyl, heteroaryl, heteroarylalkyl, heterocyclyl or heterocyclylalkyl, wherein each said alkyl, cycloalkyl, aryl, arylalkyl, heteroaryl, heteroarylalkyl, heterocyclyl and heterocyclylalkyl is unsubstituted or optionally substituted with up to five groups independently selected from the group consisting of the group consisting of oxo, halogen, cyano, —$OR^{15}$, —$NR^{11}R^{13}$, $SO_2R^{12}$, —$SR^{12}$, trifluoromethyl, difluoromethoxy and trifluoromethoxy; and $R^E$ is $C_1$-$C_8$ alkyl, $C_3$-$C_8$ cycloalkyl, aryl, arylalkyl, heteroaryl, heteroarylalkyl, heterocyclyl or heterocyclylalkyl, wherein each said alkyl, cycloalkyl, aryl, arylalkyl, heteroaryl, heteroarylalkyl, heterocyclyl and heterocyclylalkyl is unsubstituted or optionally substituted with up to five groups independently selected from the group consisting of the group consisting of oxo, halogen, cyano, —$OR^{15}$, —$NR^{11}R^{13}$, —$SO_2R^{12}$, —$SR^{12}$, trifluoromethyl, difluoromethoxy and trifluoromethoxy;

or wherein $R^C$ and $R^D$ are together with Y, Q and the atoms to which they are attached to form a 4 to 10 membered heterocyclic ring which is optionally substituted with up to five groups independently selected from the group consisting of halogen, oxo, —$OR^{15}$, —$NR^{11}R^{13}$, —$SO_2SR^{12}$, $C_1$-$C_6$ alkyl; $C_3$-$C_6$ cycloalkyl, trifluoromethyl, difluoromethoxy, trifluoromethoxy, azido, aryl, heteroaryl, arylalkyl, heteroarylalkyl, heterocyclyl and heterocyclylalkyl;

or wherein $R^D$ and $R^E$ are taken together with Y, Z and the phosphorus atom to which they are attached to form a 4 to 10 membered heterocyclic ring which is optionally substituted with up to five groups independently selected from the group consisting of halogen, oxo, —$OR^{15}$, —$NR^{11}R^{13}$, —$SO_2R^{12}$, —$SR^{12}$, $C_1$-$C_6$alkyl, $C_1$-$C_6$cyclylalkyl, trifluoromethyl, difluoromethoxy, trifluoromethoxy, azido, aryl, heteroaryl, arylalkyl, heteroarylalkyl, heterocyclyl and heterocyclylalkyl;

wherein:
  each $R^1$ is independently hydrogen, $C_1$-$C_6$ alkyl or $C_3$-$C_6$ cycloalkyl, wherein each said alkyl and cycloalkyl is unsubstituted or optionally substituted with up to five groups independently selected from the group consisting of oxo, halogen, cyano, azido and —$OR^{15}$;
  each $R^2$ is independently $C_1$-$C_6$ alkyl, $C_3$-$C_6$ cycloalkyl, aryl, arylalkyl, heteroaryl, heteroarylalkyl, heterocyclyl or heterocyclylalkyl, wherein each said alkyl, cycloalkyl, aryl, arylalkyl, heteroaryl, heteroarylalkyl, heterocyclyl and heterocyclylalkyl is unsubstituted or optionally substituted with up to five groups independently selected from the group consisting of the group consisting of oxo, halogen, cyano and —$OR^{15}$;
  each $R^3$ is independently hydrogen, $C_1$-$C_6$ alkyl, $C_2$-$C_6$ alkenyl, $C_2$-$C_6$ alkynyl, $C_3$-$C_8$ cycloalkyl, $C_3$-$C_8$ cycloalkylalkyl, heterocyclyl or heterocyclylalkyl, wherein each said alkyl, cycloalkyl, cycloalkylalkyl, heterocyclyl and heterocyclylalkyl is unsubstituted or optionally substituted with up to five groups independently selected from the group consisting of oxo, halogen, cyano, azido and —$OR^{15}$;
  each $R^4$ is independently hydrogen, $C_1$-$C_6$ alkyl or $C_3$-$C_6$ cycloalkyl, wherein each said alkyl and cycloalkyl is unsubstituted or optionally substituted with up to five groups independently selected from the group consisting of oxo, halogen, cyano, azido and —$OR^{15}$; and
  each $R^5$ is hydrogen, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkylalkyl, heterocyclyl or heterocyclylalkyl, wherein each said alkyl, cycloalkyl, cycloalkylalkyl, heterocyclyl and heterocyclylalkyl is unsubstituted or optionally substituted with up to five groups independently selected from the group consisting of oxo, halogen, cyano and azido;

or wherein when $R^1$ and $R^2$ are attached to the same atom or are attached to adjacent atoms, $R^1$ and $R^2$ are together with the atom or the atoms to which they are attached to form a 4 to 10 membered heterocyclic ring which is optionally substituted with up to three groups independently selected from the group consisting of halogen, oxo, cyano, trifluoromethyl, difluoromethoxy, trifluoromethoxy, azido, heterocyclyl and heterocyclylalkyl;

or wherein when $R^1$ and $R^3$ are attached to the same atom or are attached to adjacent atoms, $R^1$ and $R^3$ are taken together with the atom or the atoms to which they are attached to form a 4 to 10 membered heterocyclic ring which is optionally substituted with up to three groups independently selected from the group consisting of halogen, oxo, cyano, trifluoromethyl, difluoromethoxy, trifluoromethoxy, azido, heterocyclyl and heterocyclylalkyl;

or wherein when $R^1$ and $R^4$ are attached to the same atom or are attached to adjacent atoms, $R^1$ and $R^4$ are taken together with the atom or the atoms to which they are attached to form a 4 to 10 membered heterocyclic ring which is optionally substituted with up to three groups independently selected from the group consisting of halogen, oxo, cyano, trifluoromethyl, difluoromethoxy, trifluoromethoxy, azido, heterocyclyl and heterocyclylalkyl;

or wherein when $R^1$ and $R^5$ are attached to the same atom or are attached to adjacent atoms, $R^1$ and $R^5$ are taken together with the atom or the atoms to which they are attached to form a 4 to 10 membered heterocyclic ring which is optionally substituted with up to three groups independently selected from the group consisting of halogen, oxo, cyano, trifluoromethyl, difluoromethoxy, trifluoromethoxy, azido, heterocyclyl and heterocyclylalkyl;

wherein:
  each $R^{11}$ is independently hydrogen, $C_1$-$C_6$ alkyl or $C_3$-$C_6$ cycloalkyl;
  each $R^{12}$ is independently $C_1$-$C_6$ alkyl, $C_3$-$C_6$ cycloalkyl, aryl, arylalkyl, heteroaryl, heteroarylalkyl, heterocyclyl or heterocyclylalkyl;
  each $R^{13}$ is independently hydrogen, $C_1$-$C_6$ alkyl, $C_2$-$C_6$ alkenyl, $C_2$-$C_6$alkynyl, $C_3$-$C_8$ cycloalkyl, $C_3$-$C_8$ cycloalkylalkyl, heterocyclyl or heterocyclylalkyl;
  each $R^{14}$ is independently hydrogen, $C_1$-$C_6$ alkyl or $C_3$-$C_6$ cycloalkyl;

each $R^{15}$ is hydrogen, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkylalkyl, heterocyclyl or heterocyclylalkyl; and each $R^{16}$ is independently $C_1$-$C_6$ alkyl, $C_3$-$C_6$ cycloalkyl, $C_3$-$C_8$ cycloalkylalkyl, heterocyclyl or heterocyclylalkyl;

or a salt or solvate thereof.

The invention also provides compounds of the Formula (I):

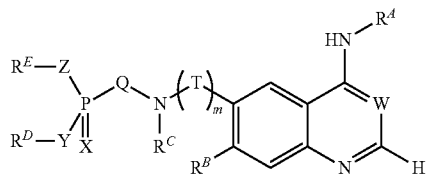

Formula I or a salt, solvate, or physiologically functional derivatives thereof;

wherein:

W is N or a C—CN group;

$R^A$ is a substituted monocyclic, bicyclic or tricyclic aryl or heteroaryl moiety;

$R^B$ is hydrogen, halogen, cyano, nitro, trifluoromethyl, difluoromethyl, trifluoromethoxy, difluoromethoxy, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkylalkyl, heterocyclyl, heterocyclylalkyl, —NR$^1$SO$_2$R$^2$, —SO$_2$NR$^3$R$^1$, —C(O)R$^4$, —C(O)OR$^5$, —OC(O)R$^4$, —NR$^1$C(O)OR$^5$, —NR$^1$C(O)R$^4$, —C(O)NR$^1$R$^3$, —NR$^1$R$^3$, —NR$^1$C(O)NR$^1$R$^3$, —OR$^5$, —S(O)R$^2$, —SO$_2$R$^2$, or —SR$^2$, wherein said alkyl, alkenyl, alkynyl, cycloalkyl, cycloalkylalkyl, heterocyclyl, and heterocyclylalkyl is optionally substituted with up to five groups independently selected from oxo, halogen, $C_1$-$C_6$ alkyl, $C_2$-$C_6$ alkenyl, $C_2$-$C_6$ alkynyl, $C_3$-$C_8$ cycloalkyl, $C_3$-$C_8$ cycloalkylalkyl, cyano, trifluoromethyl, difluoromethoxy, trifluoromethoxy, azido, —NR$^1$SO$_2$R$^2$, —SO$_2$NR$^3$R$^1$, —C(O)R$^4$, —C(O)OR$^5$, —OC(O)R$^4$, —NR$^1$C(O)OR$^6$, —NR$^1$C(O)R$^4$, —C(O)NR$^1$R$^3$, —NR$^1$R$^3$, —NR$^1$C(O)NR$^1$R$^3$, —OR$^5$, —S(O)R$^2$, —SO$_2$R$^2$, or —SR$^2$, heterocyclyl, and heterocyclylalkyl;

$R^1$ is hydrogen, $C_1$-$C_6$ alkyl, $C_3$-$C_6$ cycloalkyl, where the alkyl or cycloalkyl can be substituted with up to five groups independently selected from oxo, halogen, cyano, azido, —OR$^5$;

$R^2$ is $C_1$-$C_6$ alkyl, $C_3$-$C_6$ cycloalkyl, aryl, arylalkyl, heteroaryl, heteroarylalkyl, heterocyclyl, heterocyclylalkyl, or where each of the above alkyl, cycloalkyl, aryl, arylalkyl, heteroaryl, heteroarylalkyl, heterocyclyl, and heterocyclylalkyl is optionally substituted with up to five groups independently selected from the group consisting of oxo, halogen, cyano, —OR$^5$;

$R^3$ is hydrogen, $C_1$-$C_6$ alkyl, $C_2$-$C_6$ alkenyl, $C_2$-$C_6$ alkynyl, $C_3$-$C_8$ cycloalkyl, $C_3$-$C_8$ cycloalkylalkyl, heterocyclyl, heterocyclylalkyl, where said alkyl, cycloalkyl, cycloalkylalkyl, heterocyclyl, heterocyclylalkyl can be substituted with up to five groups independently selected from oxo, halogen, cyano, azido, —OR$^5$;

$R^4$ is hydrogen, $C_1$-$C_6$ alkyl or $C_3$-$C_6$ cycloalkyl, where the alkyl or cycloalkyl can be substituted with up to five groups independently selected from oxo, halogen, cyano, azido, OR$^5$;

$R^5$ is hydrogen, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkylalkyl, heterocyclyl, heterocyclylalkyl, where said alkyl, cycloalkyl, cycloalkylalkyl, heterocyclyl, heterocyclylalkyl can be substituted with up to five groups independently selected from oxo, halogen, cyano, azido;

$R^6$ is $C_1$-$C_6$ alkyl or $C_3$-$C_6$ cycloalkyl, $C_3$-$C_8$ cycloalkylalkyl, heterocyclyl, heterocyclylalkyl;

$R^1$ and $R^2$ together with the atoms to which they are attached can form a 4 to 10 membered heterocyclic ring, each of which is optionally substituted with up to three groups independently selected from halogen, oxo, cyano, trifluoromethyl, difluoromethoxy, trifluoromethoxy, azido, heterocyclyl and heterocyclylalkyl, or $R^1$ and $R^3$ together with the atoms to which they are attached can form 4 to 10 membered heterocyclic ring, each of which is optionally substituted with up to three groups independently selected from halogen, oxo, cyano, trifluoromethyl, difluoromethoxy, trifluoromethoxy, azido, heterocyclyl and heterocyclylalkyl;

$R^1$ and $R^4$ together with the atoms to which they are attached can form a 4 to 10 membered heterocyclic ring, each of which is optionally substituted with up to three groups independently selected from halogen, oxo, cyano, trifluoromethyl, difluoromethoxy, trifluoromethoxy, azido, heterocyclyl and heterocyclylalkyl; or $R^1$ and $R^5$ together with the atoms to which they are attached can form 4 to 10 membered heterocyclic ring, each of which is optionally substituted with up to three groups independently selected from halogen, oxo, cyano, trifluoromethyl, difluoromethoxy, trifluoromethoxy, azido, heterocyclyl and heterocyclylalkyl;

T represents $C_1$-$C_6$ alkyl, $C_2$-$C_6$ alkenyl, $C_2$-$C_6$ alkynyl, $C_3$-$C_8$ cycloalkyl, $C_3$-$C_8$ cycloalkylalkyl, aryl, arylalkyl, heteroaryl, heteroarylalkyl, heterocyclyl or heterocyclylalkyl; where each alkyl, alkenyl, alkynyl, cycloalkyl, aryl, heteroaryl and heterocyclyl portion is optionally substituted with up to three groups independently selected from oxo, halogen, $C_1$-$C_3$ alkyl, $C_2$-$C_3$ alkenyl, $C_2$-$C_3$ alkynyl, cyano, trifluoromethyl, difluoromethoxy, trifluoromethoxy, azido, —NR$^1$SO$_2$R$^2$, —SO$_2$NR$^3$R$^1$, —C(O)R$^4$, —C(O)OR$^5$, —OC(O)R$^4$, —NR$^1$C(O)OR$^5$, —NR$^1$C(O)R$^4$, —C(O)NR$^1$R$^3$, —NR$^1$R$^3$, —NR$^1$C(O)NR$^1$R$^3$, —OR$^5$, —S(O)R$^2$, —SO$_2$R$^2$, or —SR$^2$; where R$^1$, R$^2$, R$^3$, R$^4$ and R$^5$ are the same as R$^1$, R$^2$, R$^3$, R$^4$ and R$^5$ as defined above; T may optionally contain one or more heteroatoms, which heteroatoms may be further substituted or oxidized; and m is an integer from 0 to 1;

$R^C$ is H, $C_1$-$C_6$ alkyl, $C_3$-$C_6$ cycloalkyl, —SO$_2$NR$^3$R$^1$, —C(O)R$^4$, —C(O)OR$^5$, —C(O)NR$^1$R$^3$, —SO$_2$R$^2$, where the alkyl or cycloalkyl can be substituted with up to five groups independently selected from oxo, halogen, cyano, azido, —OR$^5$; where R$^1$, R$^2$, R$^3$, R$^4$ and R$^5$ are the same as R$^1$, R$^2$, R$^3$, R$^4$ and R$^5$ as defined above;

Q represents a bond, $C_1$-$C_6$ alkyl, where the alkyl is optionally substituted with up to three groups independently selected from oxo, halogen, $C_1$-$C_3$ alkyl, cyano, trifluoromethyl, difluoromethoxy, trifluoromethoxy, —NR$^1$R$^3$, —OR$^5$; where R$^1$, R$^3$ and R$^5$ are the same as R$^1$, R$^3$ and R$^5$ as defined above;

X represents O or S;

Y and Z are independently selected from a group of O, S, NR$^1$, and a divalent bond; where R$^1$ is the same as R$^1$ as defined above;

$R^D$ and $R^E$ independently are selected from $C_1$-$C_8$ alkyl, $C_3$-$C_8$ cycloalkyl, aryl, arylalkyl, heteroaryl, heteroarylalkyl, heterocyclyl, heterocyclylalkyl, trifluoromethyl, where each of the above alkyl, cycloalkyl, aryl, arylalkyl, heteroaryl, heteroarylalkyl, heterocyclyl, and heterocyclylalkyl is optionally substituted with up to five groups independently selected from the group consisting of oxo, halogen, cyano, —OR$^5$, —NR$^1$R$^3$, —SO$_2$R$^2$, —SR$^2$, trifluoromethyl, difluoromethoxy, trifluoromethoxy, where R$^1$, R$^2$, R$^3$, and R$^5$ are the same as R$^1$, R$^2$, R$^3$ and R$^5$ as defined above;

$R^C$ and $R^D$ together with the atoms to which they are attached can form a 4 to 10 membered heterocyclic ring, which is optionally substituted with up to five groups independently selected from halogen, oxo, —$OR^5$, —$NR^1R^3$, —$SO_2R^2$, —$SR^2$, $C_1$-$C_6$ alkyl; $C_3$-$C_6$ cycloalkyl; trifluoromethyl, difluoromethoxy, trifluoromethoxy, azido, aryl, heteroaryl, arylalkyl, heteroarylalkyl, heterocyclyl and heterocyclylalkyl, where $R^1$, $R^2$, $R^3$, and $R^5$ are the same as $R^1$, $R^2$, $R^3$, and $R^5$ as defined above;

or $R^D$ and $R^E$ together with the atoms to which they are attached can form a 4 to 10 membered heterocyclic ring, which is optionally substituted with up to five groups independently selected from halogen, oxo, —$OR^5$, —$NR^1R^3$, —$SO_2R^2$, —$SR^2$, $C_1$-$C_6$alkyl, $C_1$-$C_6$cyclylalkyl; trifluoromethyl, difluoromethoxy, trifluoromethoxy, azido, aryl, heteroaryl, arylalkyl, heteroarylalkyl, heterocyclyl and heterocyclylalkyl, where $R^1$, $R^2$, $R^3$, and $R^5$ are the same as $R^1$, $R^2$, $R^3$, and $R^5$ as defined above;

In some embodiments, provided is a composition comprising a compound of the Formula (I), Formula (A), (Aa), (Aa-1), (Aa-2), (Ab), (Ab-1) or (Ac), or any variations thereof, a pharmaceutically acceptable salt thereof or a hydrate or solvate thereof, and a pharmaceutically acceptable carrier.

In another aspect, provided is a method of treating a hyperproliferative disease in a mammal (e.g. human), comprising administering to the mammal (e.g. human) a therapeutically effective amount of a compound of the Formula (I), Formula (A), (Aa), (Aa-1), (Aa-2), (Ab), (Ab-1) or (Ac), or any variations thereof, or a salt or solvate thereof. In some embodiments, the method is for the treatment of a Her2 positive cancer in a mammal (e.g. human). In some embodiments, the Her2 positive cancer is breast cancer, gastric cancer, ovarian cancer.

Also provided is the use of a compound of the Formula (I), Formula (A), (Aa), (Aa-1), (Aa-2), (Ab), (Ab-1) or (Ac), or any variations thereof, in the manufacture of a medicament for the treatment of a hyperproliferative disease, such as a Her2 positive cancer in human (e.g. breast cancer, gastric cancer, ovarian cancer).

Also provided is a kit comprising a compound of the Formula (I), Formula (A), (Aa), (Aa-1), (Aa-2), (Ab), (Ab-1) or (Ac), or any variations thereof, and instructions for use in the treatment of a hyperproliferative disease, such as a Her2 positive cancer in human (e.g. breast cancer, gastric cancer, ovarian cancer).

Additional advantages and novel features of this invention shall be set forth in part in the description that follows, and in part will become apparent to those skilled in the art upon examination of the following specification, or may be learned by the practice of the invention. The advantages of the invention may be realized and attained by means of the instrumentalities, combinations, compositions, and methods particularly laid out in the appended claims.

DETAILED DESCRIPTION OF THE INVENTION

Figure 1:
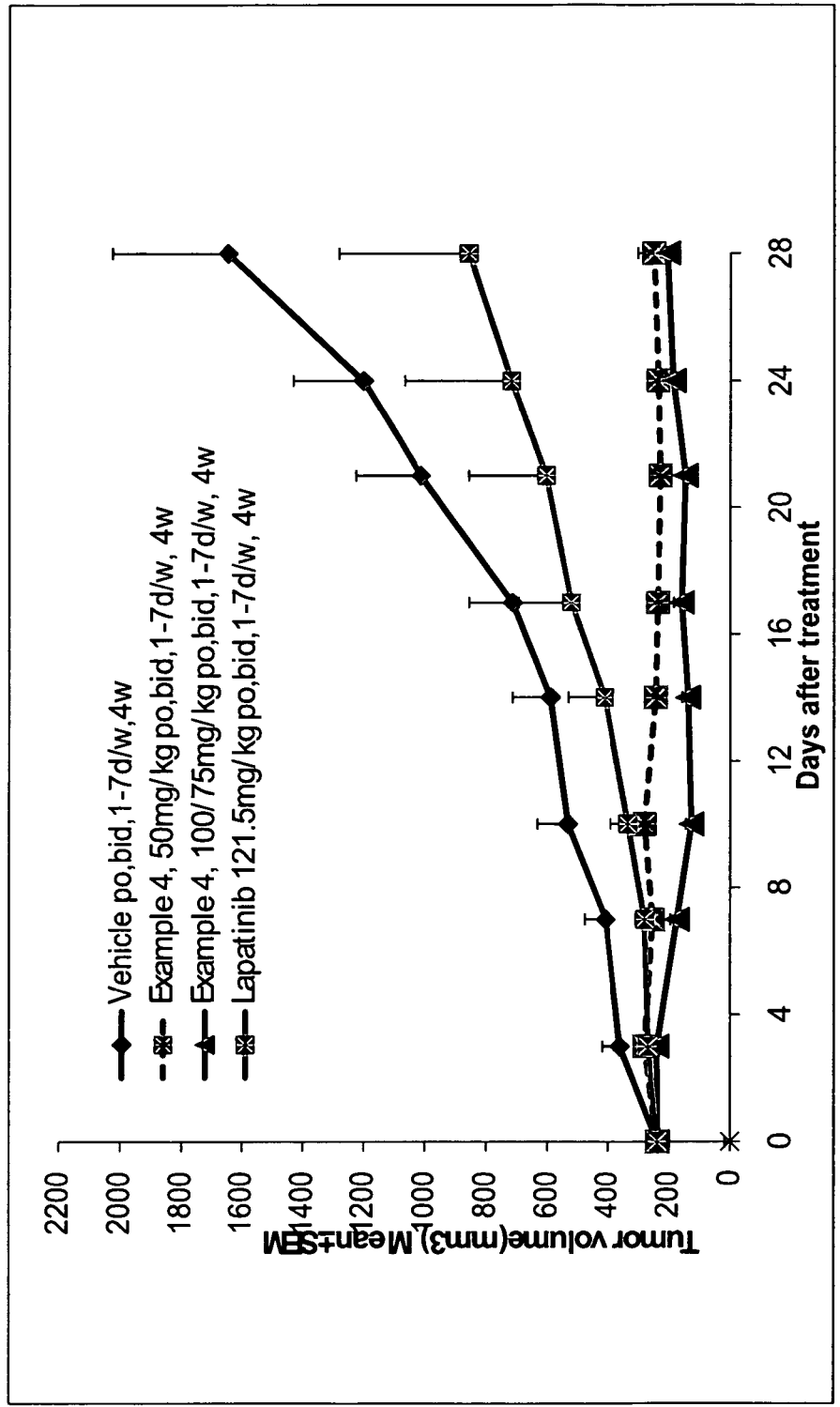
FIG. 1 shows the anticancer effect of Example 4 against NCI-N87 xenograft in Balb/c nude mice.

Phosphorus containing compounds have been used widely in industrial use and agro chemicals. However phosphorus containing compounds are rarely used in pharmaceuticals because many of them are known toxins and the phosphorus containing compounds are often difficult to synthesize. We describe phosphorus containing compounds that demonstrated anticancer activities both in vitro and in vivo, and with favorable pharmacological properties.

Definitions

Except as expressly defined otherwise, the following definition of terms is employed throughout this specification.

The term "alkyl" as used herein refers to a saturated linear or branched-chain hydrocarbon of one to twelve carbon atoms, wherein the alkyl radical may be independently substituted with one or more substituents described below. Examples of alkyl groups include, but are not limited to, methyl, ethyl, n-propyl, isopropyl, butyl, isobutyl, sec-butyl, tert-butyl, pentyl, isopentyl, tert-pentyl, hexyl, isohexyl, and the like. More preferred alkyl radicals are $C_{1-8}$ alkyls. More preferred alkyl radicals are $C_{1-4}$ alkyls.

"Alkylene" refers to the same residues as alkyl, but having bivalency. Examples of alkylene include ethylene (—$CH_2CH_2$—) and propylene (—$CH_2CH_2CH_2$—).

The term "alkenyl" refers to linear or branched-chain hydrocarbon radical of two to twelve carbon atoms, containing at least one double bond, such as ethenyl, propenyl, and the like, wherein the alkenyl radical may be optionally substituted independently with one or more substituents described herein, and includes radicals having "cis" and "trans" orientations, or alternatively, "E" and "Z" orientations. The preferred alkenyl radicals are those with 2-6 carbon atoms.

The term "alkynyl" refers to a linear or branched hydrocarbon radical of two to twelve carbon atoms containing at least one triple bond. Examples include ethynyl, propynyl, and the like, wherein the alkynyl radical may be optionally substituted independently with one or more substituents described herein. Preferred alkynyl radicals may have 2-6 carbon atoms.

The term "cycloalkyl" refers to saturated or partially unsaturated cyclic hydrocarbon radical having from three to twelve carbon atoms, wherein the cycloalkyl may be optionally substituted independently with one or more substituents described herein. The term "cycloalkyl" further includes spirocyclic, bicyclic and tricyclic cycloalkyl structures, wherein the bicyclic and tricyclic structures may include a saturated or partially unsaturated cycloalkyl fused to a saturated or partially unsaturated cycloalkyl or heterocycloalkyl ring or an aryl or heteroaryl ring. Spiro moieties are also included within the scope of this definition. Examples of cycloalkyl groups include, but are not limited to, cyclopropyl, cyclobutyl, cyclopentyl, cyclohexyl, cycloheptyl, adamantyl, norboranes and the like.

The term "cycloalkylalkyl" means an alkyl moiety (as defined above) substituted with one or more cycloalkyl moiety (also as defined above). The preferred cycloalkylalkyl radicals are cycloalkyl-$C_{1-3}$-alkyls. Examples include cyclopropylmethyl, (1-cyclohexenyl)ethyl, and the like.

The term "heteroalkyl" refers to saturated or partially unsaturated linear or branched-chain hydrocarbon radical of one to twelve carbon atoms, wherein at least one of the carbon atoms is replaced with a heteroatom selected from N, O, or S, and wherein the radical may be a carbon radical or heteroatom radical (i.e., the heteroatom may appear in the middle or at the end of the radical). The heteroatom may be oxized, such as S(O), S(O)$_2$. The heteroalkyl radical may be optionally substituted independently with one or more substituents described herein. The term "heteroalkyl" encompasses alkoxy and heteroalkoxy radicals.

The term "heterocyclyl" refers to a saturated or partially unsaturated cyclic radical of 3 to 8 ring atoms in which at least one ring atom is a heteroatom selected from nitrogen, oxygen and sulfur, the remaining ring atoms being C where one or more ring atoms may be optionally substituted independently with one or more substituent described below. The radical may be a carbon radical or heteroatom radical. "Heterocyclyl" also includes radicals where heterocycle radicals are fused with aromatic or heteroaromatic rings. Spiro moieties are also included within the scope of this definition. Examples of heterocycloalkyl rings include, but are not limited to, pyrrolidine, piperidine, piperazine, tetrahydropyranyl, morpholine, thiomorpholine, homopiperazine, phthalimide, and derivatives thereof.

The term "heterocyclylalkyl" means an alkyl moiety (as defined above) substituted with one or more cycloalkyl moiety (also as defined above). The preferred heterocyclylalkyl radicals are heterocyclyl-$C_{1-3}$-alkyls. Examples include (2-tetrahydrofuryl)methyl, (1-pyrrolidinyl)propyl, and the like.

"Aryl" means an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl), which is optionally mono-, di-, or trisubstituted with, e.g., halogen, lower alkyl, lower alkyloxy, trifluoromethyl, aryl, heteroaryl, and hydroxy.

"Heteroaryl" means a monocyclic aromatic radical of 5 to 10 ring atoms or a polycyclic aromatic radical, containing one or more ring heteroatoms selected from N, O, or S, the remaining ring atoms being C. The aromatic radical is optionally substituted independently with one or more substituents described herein. Examples include, but are not limited to, furyl, thienyl, pyrrolyl, pyridyl, pyrazolyl, pyrimidinyl, imidazolyl, pyrazinyl, indolyl, thiophen-2-yl, quinolyl, benzopyranyl, thiazolyl, and derivatives thereof.

The term "arylalkyl" means an alkyl moiety (as defined above) substituted with one or more aryl moiety (also as defined above). The preferred arylalkyl radicals are aryl-$C_{1-3}$-alkyls. Examples include benzyl, phenylethyl, and the like.

The term "heteroarylalkyl" means an alkyl moiety (as defined above) substituted with a heteroaryl moiety (as defined above). The preferred heteroarylalkyl radicals are 5- or 6-membered heteroaryl-$C_{1-3}$-alkyl. Examples include furfuryl, oxazolemethyl, pyridylethyl and the like.

The term "halo" represents fluoro, chloro, bromo or iodo. Likewise, the term "halogen" refers to a fluorine, chlorine, bromine, or iodine substituent.

In one aspect, provided is a compound of Formula (A):

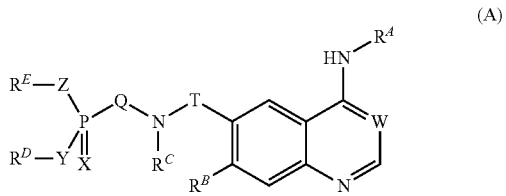

(A)

wherein:
W is N or a C—CN group;
$R^A$ is a substituted monocyclic, bicyclic or tricyclic aryl or heteroaryl moiety, or an arylalkyl group;
$R^B$ is hydrogen, halogen, cyano, nitro, trifluoromethyl, difluoromethyl, trifluoromethoxy, difluoromethoxy, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkylalkyl, heterocyclyl, heterocyclylalkyl, —$NR^1SO_2R^2$, —$SO_2NR^1R^3$, —$C(O)R^4$, —$C(O)OR^5$, —$OC(O)R^4$, —$NR^1C(O)OR^5$, —$NR^1C(O)R^4$, —$C(O)NR^1R^3$, —$NR^1R^3$, —$NR^1C(O)NR^1R^3$, —$OR^5$, —$S(O)R^2$, —$SO_2R^2$ or —$SR^2$, wherein each said alkyl, alkenyl, alkynyl, cycloalkyl, cycloalkylalkyl, heterocyclyl and heterocyclylalkyl is unsubstituted or optionally substituted with up to five groups independently selected from the group consisting of oxo, halogen, $C_1$-$C_6$ alkyl, $C_2$-$C_6$ alkenyl, $C_2$-$C_6$ alkynyl, $C_3$-$C_8$ cycloalkyl, $C_3$-$C_8$ cycloalkylalkyl, cyano, trifluoromethyl, difluoromethoxy, trifluoromethoxy, azido, —$NR^{11}SO_2R^{12}$, —$SO_2NR^{11}R^{13}$, —$C(O)R^{14}$, —$C(O)OR^{15}$, —$OC(O)R^{14}$, —$NR^{11}C(O)OR^{16}$, —$NR^{11}C(O)R^{14}$, —$C(O)NR^{11}R^{13}$, —$NR^{11}R^{13}$, —$NR^{11}C(O)NR^{11}R^{13}$, —$OR^{15}$, —$S(O)R^{12}$, —$SO_2R^{12}$, —$SR^{12}$, heterocyclyl and heterocyclylalkyl;

T is a bond or a divalent radical formed by removing an additional hydrogen atom from a $C_1$-$C_6$ alkyl, $C_2$-$C_6$ alkenyl, $C_2$-$C_6$ alkynyl, $C_3$-$C_8$ cycloalkyl, $C_3$-$C_8$ cycloalkylalkyl, aryl, arylalkyl, heteroaryl, heteroarylalkyl, heterocyclyl or heterocyclylalkyl; wherein each said alkyl, alkenyl, alkynyl, cycloalkyl, aryl, heteroaryl and heterocyclyl is unsubstituted or optionally substituted with up to three groups independently selected from the group consisting of oxo, halogen, $C_1$-$C_3$ alkyl, $C_2$-$C_3$ alkenyl, $C_2$-$C_3$ alkynyl, cyano, trifluoromethyl, difluoromethoxy, trifluoromethoxy, azido, —$NR^{11}SO_2R^{12}$, —$SO_2NR^{11}R^{13}$, —$C(O)R^{14}$, —$C(O)OR^{15}$, —$OC(O)R^{14}$, —$NR^{11}C(O)OR^{15}$, —$NR^{11}C(O)R^{14}$, —$C(O)NR^{11}R^{13}$, $NR^{11}R^{13}$, —$NR^{11}C(O)NR^{11}R^{13}$, —$OR^{15}$, —$S(O)R^{12}$, —$SO_2R^{12}$ and —$SR^{12}$;

Q is a bond or $C_1$-$C_6$ alkyl, wherein said alkyl is unsubstituted or optionally substituted with up to three groups independently selected from the group consisting of oxo, halogen, $C_1$-$C_3$ alkyl, cyano, trifluoromethyl, difluoromethoxy, trifluoromethoxy, —$NR^{11}R^{13}$ and —$OR^{15}$;

X is O or S;
Y and Z are independently O, S, $NR^1$ or a bond;
$R^C$ is H, $C_1$-$C_6$ alkyl, $C_3$-$C_6$ cycloalkyl, —$SO_2NR^3R^1$, —$C(O)R^4$, —$C(O)OR^5$, —$C(O)NR^1R^3$, or —$SO_2R^2$, wherein each said alkyl and cycloalkyl is unsubstituted or optionally substituted with up to five groups independently selected from the group consisting of oxo, halogen, cyano, azido and —$OR^{15}$;

$R^D$ is $C_1$-$C_8$ alkyl, $C_3$-$C_8$ cycloalkyl, aryl, arylalkyl, heteroaryl, heteroarylalkyl, heterocyclyl or heterocyclylalkyl, wherein each said alkyl, cycloalkyl, aryl, arylalkyl, heteroaryl, heteroarylalkyl, heterocyclyl and heterocyclylalkyl is unsubstituted or optionally substituted with up to five groups independently selected from the group consisting of the group consisting of oxo, halogen, cyano, —$OR^{15}$, $NR^{11}R^{13}$, $SO_2R^{12}$, —$SR^{12}$, trifluoromethyl, difluoromethoxy and trifluoromethoxy; and $R^E$ is $C_1$-$C_8$ alkyl, $C_3$-$C_8$ cycloalkyl, aryl, arylalkyl, heteroaryl, heteroarylalkyl, heterocyclyl or heterocyclylalkyl, wherein each said alkyl, cycloalkyl, aryl, arylalkyl, heteroaryl, heteroarylalkyl, heterocyclyl and heterocyclylalkyl is unsubstituted or optionally substituted with up to five groups independently selected from the group consisting of the group consisting of oxo, halogen, cyano, —$OR^{15}$, —$NR^{11}R^{13}$, —$SO_2R^{12}$, —$SR^{12}$, trifluoromethyl, difluoromethoxy and trifluoromethoxy;

or wherein $R^C$ and $R^D$ are together with Y, Q and the atoms to which they are attached to form a 4 to 10 membered heterocyclic ring which is optionally substituted with up to five groups independently selected from the group consisting of halogen, oxo, —$OR^{15}$, —$SO_2R^{12}$, —$SR^{12}$, $C_1$-$C_6$ alkyl; $C_3$-$C_6$ cycloalkyl, trifluoromethyl, difluoromethoxy, trifluoromethoxy, azido, aryl, heteroaryl, arylalkyl, heteroarylalkyl, heterocyclyl and heterocyclylalkyl;

or wherein $R^D$ and $R^E$ are taken together with Y, Z and the phosphorus atom to which they are attached to form a 4 to 10 membered heterocyclic ring which is optionally substituted with up to five groups independently selected from the group consisting of halogen, oxo, —$OR^{15}$, —$NR^{11}R^{13}$, —$SO_2R^{12}$, $SR^{12}$, $C_1$-$C_6$alkyl, $C_1$-$C_6$cyclylalkyl, trifluoromethyl, difluoromethoxy, trifluoromethoxy, azido, aryl, heteroaryl, arylalkyl, heteroarylalkyl, heterocyclyl and heterocyclylalkyl;

Wherein:

each $R^1$ is independently hydrogen, $C_1$-$C_6$ alkyl or $C_3$-$C_6$ cycloalkyl, wherein each said alkyl and cycloalkyl is unsubstituted or optionally substituted with up to five groups independently selected from the group consisting of oxo, halogen, cyano, azido and —$OR^{15}$;

each $R^2$ is independently $C_1$-$C_6$ alkyl, $C_3$-$C_6$ cycloalkyl, aryl, arylalkyl, heteroaryl, heteroarylalkyl, heterocyclyl or heterocyclylalkyl, wherein each said alkyl, cycloalkyl; aryl, arylalkyl, heteroaryl, heteroarylalkyl, heterocyclyl and heterocyclylalkyl is unsubstituted or optionally substituted with up to five groups independently selected from the group consisting of the group consisting of oxo, halogen, cyano and —$OR^{15}$;

each $R^3$ is independently hydrogen, $C_1$-$C_6$ alkyl, $C_2$-$C_6$ alkenyl, $C_2$-$C_6$ alkynyl, $C_3$-$C_8$ cycloalkyl, $C_3$-$C_8$ cycloalkylalkyl, heterocyclyl or heterocyclylalkyl, wherein each said alkyl, cycloalkyl, cycloalkylalkyl, heterocyclyl and heterocyclylalkyl is unsubstituted or optionally substituted with up to five groups independently selected from the group consisting of oxo, halogen, cyano, azido and —$OR^{15}$;

each $R^4$ is independently hydrogen, $C_1$-$C_6$ alkyl or $C_3$-$C_6$ cycloalkyl, wherein each said alkyl and cycloalkyl is unsubstituted or optionally substituted with up to five groups independently selected from the group consisting of oxo, halogen, cyano, azido and —$OR^{15}$; and each $R^5$ is hydrogen, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkylalkyl, heterocyclyl or heterocyclylalkyl, wherein each said alkyl, cycloalkyl, cycloalkylalkyl, heterocyclyl and heterocyclylalkyl is unsubstituted or optionally substituted with up to five groups independently selected from the group consisting of oxo, halogen, cyano and azido;

or wherein when $R^1$ and $R^2$ are attached to the same atom or are attached to adjacent atoms, $R^1$ and $R^2$ are together with the atom or the atoms to which they are attached to form a 4 to 10 membered heterocyclic ring which is optionally substituted with up to three groups independently selected from the group consisting of halogen, oxo, cyano, trifluoromethyl, difluoromethoxy, trifluoromethoxy, azido, heterocyclyl and heterocyclylalkyl;

or wherein when $R^1$ and $R^3$ are attached to the same atom or are attached to adjacent atoms, $R^1$ and $R^3$ are taken together with the atom or the atoms to which they are attached to form a 4 to 10 membered heterocyclic ring which is optionally substituted with up to three groups independently selected from the group consisting of halogen, oxo, cyano, trifluoromethyl, difluoromethoxy, trifluoromethoxy, azido, heterocyclyl and heterocyclylalkyl;

or wherein when $R^1$ and $R^4$ are attached to the same atom or are attached to adjacent atoms, $R^1$ and $R^4$ are taken together with the atom or the atoms to which they are attached to form a 4 to 10 membered heterocyclic ring which is optionally substituted with up to three groups independently selected from the group consisting of halogen, oxo, cyano, trifluoromethyl, difluoromethoxy, trifluoromethoxy, azido, heterocyclyl and heterocyclylalkyl;

or wherein when $R^1$ and $R^5$ are attached to the same atom or are attached to adjacent atoms, $R^1$ and $R^5$ are taken together with the atom or the atoms to which they are attached to form a 4 to 10 membered heterocyclic ring which is optionally substituted with up to three groups independently selected from the group consisting of halogen, oxo, cyano, trifluoromethyl, difluoromethoxy, trifluoromethoxy, azido, heterocyclyl and heterocyclylalkyl;

wherein:

each $R^{11}$ is independently hydrogen, $C_1$-$C_6$ alkyl or $C_3$-$C_6$ cycloalkyl;

each $R^{12}$ is independently $C_1$-$C_6$ alkyl, $C_3$-$C_6$ cycloalkyl, aryl, arylalkyl, heteroaryl, heteroarylalkyl, heterocyclyl or heterocyclylalkyl;

each $R^{13}$ is independently hydrogen, $C_1$-$C_6$ alkyl, $C_2$-$C_6$ alkenyl, $C_2$-$C_6$ alkynyl, $C_3$-$C_8$ cycloalkyl, $C_3$-$C_8$ cycloalkylalkyl, heterocyclyl or heterocyclylalkyl;

each $R^{14}$ is independently hydrogen, $C_1$-$C_6$ alkyl or $C_3$-$C_6$ cycloalkyl;

each $R^{15}$ is hydrogen, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkylalkyl, heterocyclyl or heterocyclylalkyl; and each $R^{16}$ is independently $C_1$-$C_6$ alkyl, $C_3$-$C_6$ cycloalkyl, $C_3$-$C_8$ cycloalkylalkyl, heterocyclyl or heterocyclylalkyl;

or a salt or solvate thereof.

In some embodiments, the compound is of the Formula (Aa):

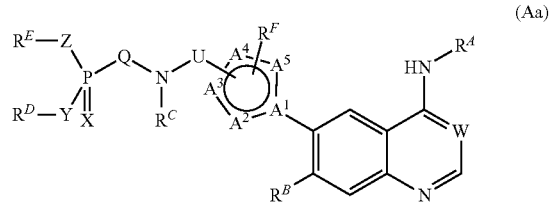

(Aa)

wherein $A^1$, $A^2$, $A^3$, $A^4$ and $A^5$ are taken together to form a five-membered heteroaryl; each $A^1$, $A^2$, $A^3$, $A^4$ and $A^5$ is independently O, N, S, C or CH; provided that at least one of $A^1$, $A^2$, $A^3$, $A^4$ and $A^5$ is a heteroatom selected from the group consisting of O, N, and S, and at least one of $A^1$, $A^2$, $A^3$, $A^4$ and $A^5$ is C or CH; U is $C_1$-$C_3$ alkylene optionally substituted with up to three groups independently selected from the group consisting of halogen, cyano, oxo, —$OR^{15}$ and $C_1$-$C_3$alkyl; provided that U is attached to the five-membered heteroaryl through a carbon atom on the heteroaryl; $R^F$ is hydrogen, halogen, cyano, nitro, trifluoromethyl, difluoromethyl, trifluoromethoxy, difluoromethoxy, $C_1$-$C_6$ alkyl, $C_3$-$C_6$ cycloalkyl, $C_4$-$C_6$cycloalkylalkyl, heterocyclyl, heterocyclylalkyl, —$NR^1SO_2R^2$, —$SO_2NR^3R^1$, —$C(O)R^4$, —$C(O)OR^5$, —$NR^1C(O)OR^5$, —$NR^1C(O)R^4$, —$C(O)NR^1R^3$, $NR^1R^3$, —$NR^1C(O)NR^1R^3$, —$OR^5$, —$S(O)R^2$, —$SO_2R^2$, or —$SR^2$; and W, Q, X, Y, Z, $R^A$, $R^B$, $R^C$, $R^D$ and $R^E$ are as defined for formula (A); or a salt or solvate thereof. In some embodiments, the five-membered heteroaryl is selected from the group consisting of:

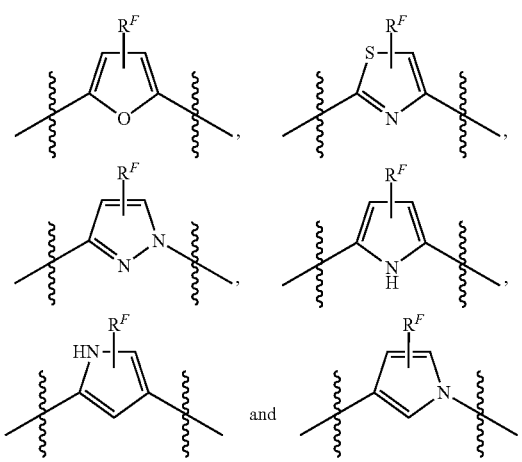

In some embodiments, the compound is of the Formula (Aa-1):

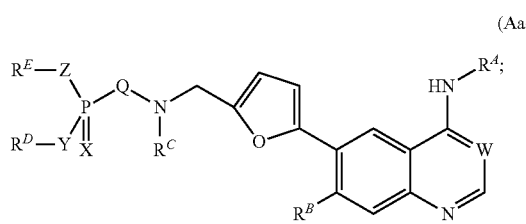

(Aa-1)

wherein W, Q, X, Y, Z, $R^A$, $R^B$, $R^C$, $R^D$ and $R^E$ are as defined for formula (A); or a salt or solvate thereof.

In some embodiments, the compound is of the Formula (Aa-2):

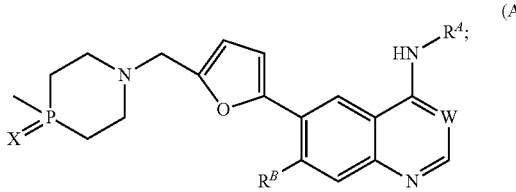

(Aa-2)

wherein W, X, $R^A$ and $R^B$ are as defined for formula (A); or a salt or solvate thereof.

In some embodiments, the compound is of the Formula (Ab):

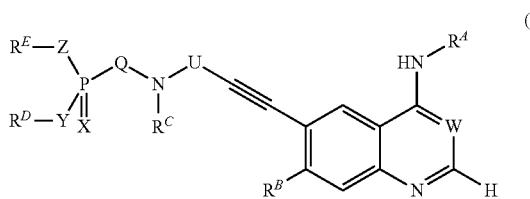

(Ab)

wherein U is $C_1$-$C_3$ alkylene optionally substituted with up to three groups independently selected from the group consisting of halogen, cyano, oxo, —$OR^{15}$ and $C_1$-$C_3$alkyl; and W, Q, X, Y, Z, $R^A$, $R^B$, $R^C$, $R^D$ and $R^E$ are as defined for formula (A); or a salt or solvate thereof.

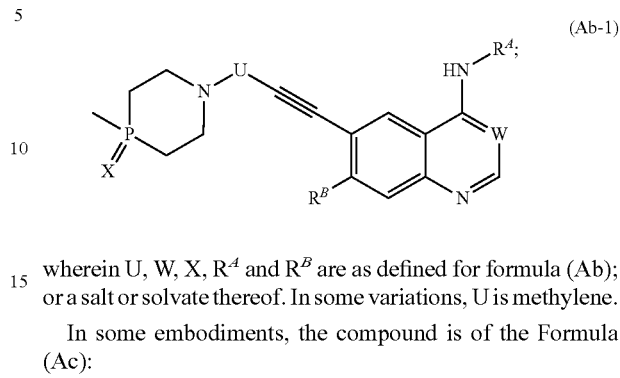

(Ab-1)

wherein U, W, X, $R^A$ and $R^B$ are as defined for formula (Ab); or a salt or solvate thereof. In some variations, U is methylene.

In some embodiments, the compound is of the Formula (Ac):

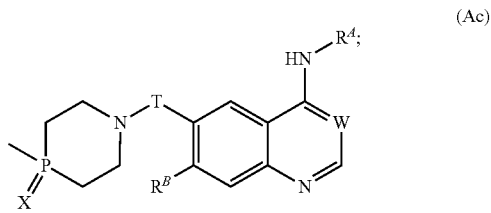

(Ac)

wherein T, W, X, $R^A$ and $R^B$ are as defined for formula (A); or a salt or solvate thereof.

In some embodiments, the compound is of the Formula (A), (Aa), (Aa-1), (Aa-2), (Ab), (Ab-1) or (Ac), wherein $R^A$ is selected from the group consisting of:

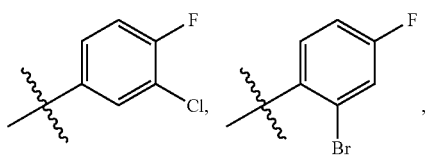

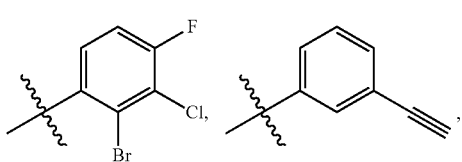

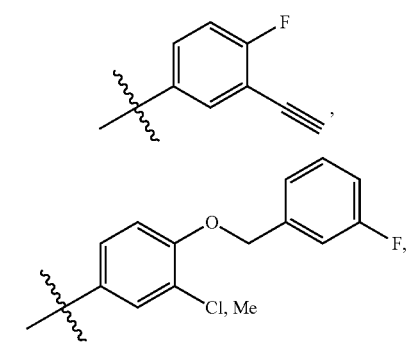

-continued

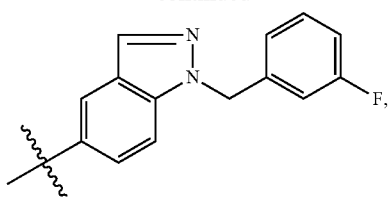

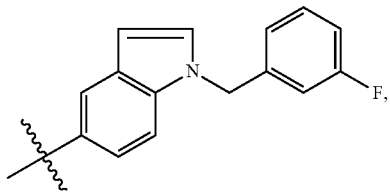

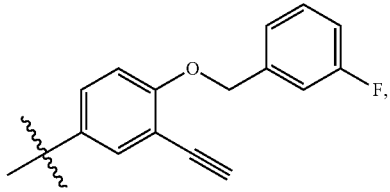

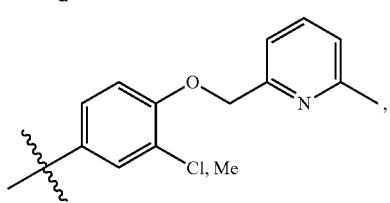

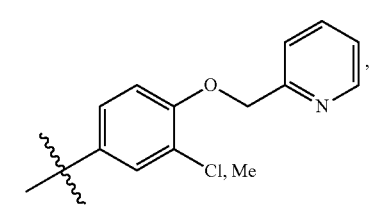

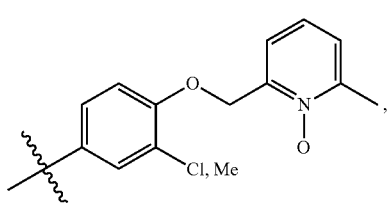

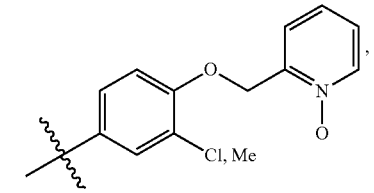

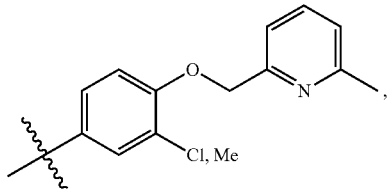

-continued

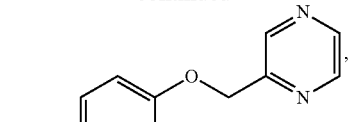

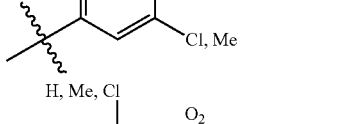

and

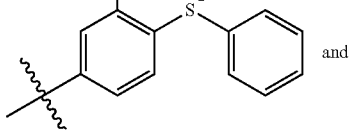

or a salt or solvate thereof. In some embodiments, $R^A$ is

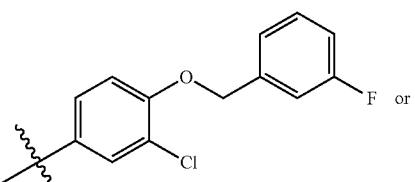 or

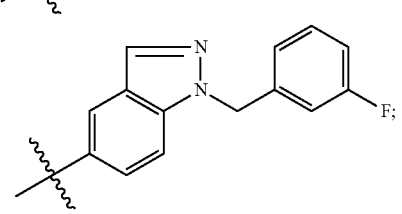

or a salt or solvate thereof.

In some embodiments, the compound is of the Formula (A), (Aa), (Aa-1), (Aa-2), (Ab), (Ab-1) or (Ac), or any variations described herein, where $R^B$ is selected from the group consisting of hydrogen, halogen, and —$OR^5$; or a salt or solvate thereof. In some variations, $R^B$ is hydrogen. $R^A$ is

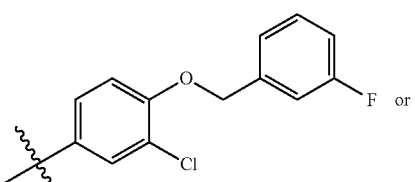 or

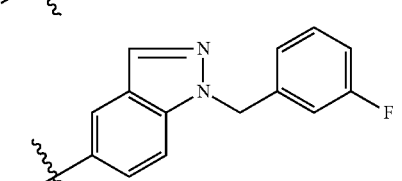

and $R^B$ is selected from the group consisting of hydrogen, halogen, and —$OR^5$.

In some embodiments, the compound is of the Formula (A), (Aa), (Aa-1), (Aa-2), (Ab), (Ab-1) or (Ac), or any variations described herein, where X is O. In some embodiments, X is S. In some variations, $R^A$ is

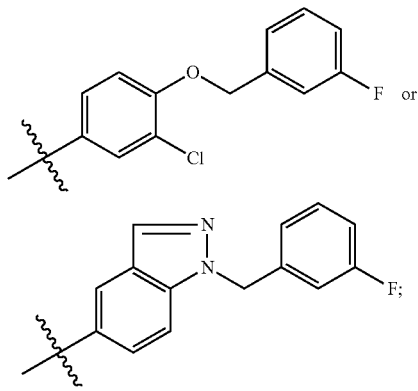

$R^B$ is selected from the group consisting of hydrogen, halogen, and —$OR^5$; and X is O.

In some embodiments, the compound is of the Formula (A), (Aa), (Aa-1), (Aa-2), (Ab), (Ab-1) or (Ac), or any variations described herein, where W is N. In some embodiments, W is C—CN. In some variations, $R^A$ is

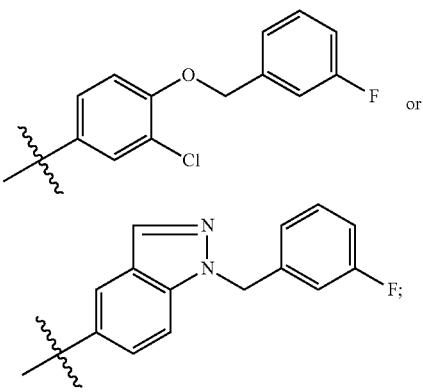

$R^B$ is selected from the group consisting of hydrogen, halogen, and —$OR^5$; X is O and W is N.

The invention also provides compounds of the Formula (I):

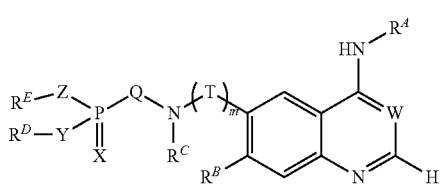

Formula I or a salt, solvate, or physiologically functional derivatives thereof;
wherein:
W is N or a C—CN group;
$R^A$ is a substituted monocyclic, bicyclic or tricyclic aryl or heteroaryl moiety;

$R^B$ is hydrogen, halogen, cyano, nitro, trifluoromethyl, difluoromethyl, trifluoromethoxy, difluoromethoxy, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkylalkyl, heterocyclyl, heterocyclylalkyl, —$NR^1SO_2R^2$, —$SO_2NR^3R^1$, —$C(O)R^4$, —$C(O)OR^5$, —$OC(O)R^4$, —$NR^1C(O)OR^5$, —$NR^1C(O)R^4$, —$C(O)NR^1R^3$, —$NR^1R^3$, —$NR^1C(O)NR^1R^3$, —$OR^5$, —$S(O)R^2$, —$SO_2R^2$, or —$SR^2$, wherein said alkyl, alkenyl, alkynyl, cycloalkyl, cycloalkylalkyl, heterocyclyl, and heterocyclylalkyl is optionally substituted with up to five groups independently selected from oxo, halogen, $C_1$-$C_6$ alkyl, $C_2$-$C_6$ alkenyl, $C_2$-$C_6$ alkynyl, $C_3$-$C_8$ cycloalkyl, $C_3$-$C_8$ cycloalkylalkyl, cyano, trifluoromethyl, difluoromethoxy, trifluoromethoxy, azido, —$NR^1SO_2R^2$, —$SO_2NR^3R^1$, —$C(O)R^4$, —$C(O)OR^5$, —$OC(O)R^4$, —$NR^1C(O)OR^6$, —$NR^1C(O)R^4$, —$C(O)NR^1R^3$, —$NR^1R^3$, —$NR^1C(O)NR^1R^3$, —$OR^5$, —$S(O)R^2$, —$SO_2R^2$, or —$SR^2$, heterocyclyl, and heterocyclylalkyl;

$R^1$ is hydrogen, $C_1$-$C_6$ alkyl, $C_3$-$C_6$ cycloalkyl, where the alkyl or cycloalkyl can be substituted with up to five groups independently selected from oxo, halogen, cyano, azido, —$OR^5$;

$R^2$ is $C_1$-$C_6$ alkyl, $C_3$-$C_6$ cycloalkyl, aryl, arylalkyl, heteroaryl, heteroarylalkyl, heterocyclyl, heterocyclylalkyl, or where each of the above alkyl, cycloalkyl, aryl, arylalkyl, heteroaryl, heteroarylalkyl, heterocyclyl, and heterocyclylalkyl is optionally substituted with up to five groups independently selected from the group consisting of oxo, halogen, cyano, —$OR^5$;

$R^3$ is hydrogen, $C_1$-$C_6$ alkyl, $C_2$-$C_6$ alkenyl, $C_2$-$C_6$ alkynyl, $C_3$-$C_8$ cycloalkyl, $C_3$-$C_8$ cycloalkylalkyl, heterocyclyl, heterocyclylalkyl, where said alkyl, cycloalkyl, cycloalkylalkyl, heterocyclyl, heterocyclylalkyl can be substituted with up to five groups independently selected from oxo, halogen, cyano, azido, —$OR^5$;

$R^4$ is hydrogen, $C_1$-$C_6$ alkyl or $C_3$-$C_6$ cycloalkyl, where the alkyl or cycloalkyl can be substituted with up to five groups independently selected from oxo, halogen, cyano, azido, —$OR^5$;

$R^5$ is hydrogen, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkylalkyl, heterocyclyl, heterocyclylalkyl, where said alkyl, cycloalkyl, heterocyclyl, heterocyclylalkyl can be substituted with up to five groups independently selected from oxo, halogen, cyano, azido;

$R^6$ is $C_1$-$C_6$ alkyl or $C_3$-$C_6$ cycloalkyl, $C_3$-$C_8$ cycloalkylalkyl, heterocyclyl, heterocyclylalkyl;

$R^1$ and $R^2$ together with the atoms to which they are attached can form a 4 to 10 membered heterocyclic ring, each of which is optionally substituted with up to three groups independently selected from halogen, oxo, cyano, trifluoromethyl, difluoromethoxy, trifluoromethoxy, azido, heterocyclyl and heterocyclylalkyl, or $R^1$ and $R^3$ together with the atoms to which they are attached can form 4 to 10 membered heterocyclic ring, each of which is optionally substituted with up to three groups independently selected from halogen, oxo, cyano, trifluoromethyl, difluoromethoxy, trifluoromethoxy, azido, heterocyclyl and heterocyclylalkyl;

$R^1$ and $R^4$ together with the atoms to which they are attached can form a 4 to 10 membered heterocyclic ring, each of which is optionally substituted with up to three groups independently selected from halogen, oxo, cyano, trifluoromethyl, difluoromethoxy, trifluoromethoxy, azido, heterocyclyl and heterocyclylalkyl; or $R^1$ and $R^5$ together with the atoms to which they are attached can form 4 to 10 membered heterocyclic ring, each of which is optionally substituted with up to three groups independently selected from halogen, oxo, cyano, trifluoromethyl, difluoromethoxy, trifluoromethoxy, azido, heterocyclyl and heterocyclylalkyl;

T represents $C_1$-$C_6$ alkyl, $C_2$-$C_6$ alkenyl, $C_2$-$C_6$ alkynyl, $C_3$-$C_8$ cycloalkyl, $C_3$-$C_8$ cycloalkylalkyl, aryl, arylalkyl, heteroaryl, heteroarylalkyl, heterocyclyl or heterocyclylalkyl; where each alkyl, alkenyl, alkynyl, cycloalkyl, aryl, heteroaryl and heterocyclyl portion is optionally substituted with up to three groups independently selected from oxo, halogen, $C_1$-$C_3$ alkyl, $C_2$-$C_3$ alkenyl, $C_2$-$C_3$ alkynyl, cyano, trifluoromethyl, difluoromethoxy, trifluoromethoxy, azido, $SO_2R^2$, —$SO_2NR^3R^1$, —$C(O)R^4$, —$C(O)OR^5$, —$OC(O)R^4$, —$NR^1C(O)OR^5$, —$NR^1C(O)R^4$, —$C(O)NR^1R^3$, —$NR^1R^3$, —$NR^1C(O)NR^1R^3$, —$OR^5$, —$S(O)R^2$, —$SO_2R^2$, or —$SR^2$; where $R^1, R^2, R^3, R^4$ and $R^5$ are the same as $R^1, R^2, R^3, R^4$ and $R^5$ as defined above; T may optionally contain one or more heteroatoms, which heteroatoms may be further substituted or oxidized; and m is an integer from 0 to 1;

$R^C$ is H, $C_1$-$C_6$ alkyl, $C_3$-$C_6$ cycloalkyl, —$SO_2NR^3R^1$, —$C(O)R^4$, —$C(O)OR^5$, —$C(O)NR^1R^3$, —$SO_2R^2$, where the alkyl or cycloalkyl can be substituted with up to five groups independently selected from oxo, halogen, cyano, azido, —$OR^5$; where $R^1, R^2, R^3, R^4$ and $R^5$ are the same as $R^1, R^2, R^3, R^4$ and $R^5$ as defined above;

Q represents a bond, $C_1$-$C_6$ alkyl, where the alkyl is optionally substituted with up to three groups independently selected from oxo, halogen, $C_1$-$C_3$ alkyl, cyano, trifluoromethyl, difluoromethoxy, trifluoromethoxy, —$NR^1R^3$, —$OR^5$; where $R^1, R^3$ and $R^5$ are the same as $R^1, R^3$ and $R^5$ as defined above;

X represents O or S;

Y and Z are independently selected from a group of O, S, $NR^1$, and a divalent bond; where $R^1$ is the same as $R^1$ as defined above;

$R^D$ and $R^E$ independently are selected from $C_1$-$C_8$ alkyl, $C_3$-$C_8$ cycloalkyl, aryl, arylalkyl, heteroaryl, heteroarylalkyl, heterocyclyl, heterocyclylalkyl, trifluoromethyl, where each of the above alkyl, cycloalkyl, aryl, arylalkyl, heteroaryl, heteroarylalkyl, heterocyclyl, and heterocyclylalkyl is optionally substituted with up to five groups independently selected from the group consisting of oxo, halogen, cyano, —$OR^5$, —$NR^1R^3$, —$SO_2R^2$, —$SR^2$, trifluoromethyl, difluoromethoxy, trifluoromethoxy, where $R^1, R^2, R^3$, and $R^5$ are the same as $R^1, R^2, R^3$ and $R^5$ as defined above;

$R^C$ and $R^D$ together with the atoms to which they are attached can form a 4 to 10 membered heterocyclic ring, which is optionally substituted with up to five groups independently selected from halogen, oxo, —$OR^5$, —$NR^1R^3$, —$SO_2R^2$, —$SR^2$, $C_1$-$C_6$ alkyl; $C_3$-$C_6$ cycloalkyl; trifluoromethyl, difluoromethoxy, trifluoromethoxy, azido, aryl, heteroaryl, arylalkyl, heteroarylalkyl, heterocyclyl and heterocyclylalkyl, where $R^1, R^2, R^3$, and $R^5$ are the same as $R^1, R^2, R^3$, and $R^5$ as defined above;

or $R^D$ and $R^E$ together with the atoms to which they are attached can form a 4 to 10 membered heterocyclic ring, which is optionally substituted with up to five groups independently selected from halogen, oxo, —$OR^5$, —$NR^1R^3$, —$SO_2R^2$, —$SR^2$, $C_1$-$C_6$alkyl, $C_1$-$C_6$cyclylalkyl; trifluoromethyl, difluoromethoxy, trifluoromethoxy, azido, aryl, heteroaryl, arylalkyl, heteroarylalkyl, heterocyclyl and heterocyclylalkyl, where $R^1, R^2, R^3$, and $R^5$ are the same as $R^1, R^2, R^3$, and $R^5$ as defined above;

In one preferred embodiment, T of Formula I is a heteroarylalkyl, and m is 1, as indicated in Formula Ia.

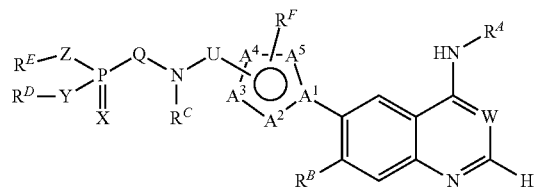

Formula Ia where $R^A, R^B, R^C, R^D, R^E, Q, Y, Z$ are the same as $R^A, R^B, R^C, R^D, R^E, X, Q, Y, Z$ as defined above.

at least one of $A^1, A^2, A^3, A^4, A^5$ is a heteroatom selected from O, N, and S; and at least one of $A^1, A^2, A^3, A^4, A^5$ is a carbon atom.

U is a $C_1$-$C_3$ alkyl, and is optionally substituted with up to three groups independently selected from halogen, cyano, oxo, —$OR^5$, $C_1$-$C_3$alkyl; and U is connected to the five-membered heteroaryl through a carbon atom on the heteroaryl.

$R^F$ is selected from hydrogen, halogen, cyano, nitro, trifluoromethyl, difluoromethyl, trifluoromethoxy, difluoromethoxy, $C_1$-$C_6$ alkyl, $C_3$-$C_6$ cycloalkyl, $C_4$-$C_6$ cycloalkylalkyl, heterocyclyl, heterocyclylalkyl, —$NR^1SO_2R^2$, —$SO_2NR^3R^1$, —$C(O)R^4$, —$C(O)OR^5$, —$NR^1C(O)OR^5$, —$NR^1C(O)R^4$, —$C(O)NR^1R^3$, —$NR^1R^3$, —$NR^1C(O)NR^1R^3$, —$OR^5$, —$S(O)R^2$, —$SO_2R^2$, or —$SR^2$; where $R^1, R^2, R^3, R^4$ and $R^5$ are the same as $R^1, R^2, R^3, R^4$ and $R^5$ as defined above. In some embodiments, the five-membered heteroaryl containing $A^1, A^2, A^3, A^4$ and $A^5$ is selected from the group consisting of:

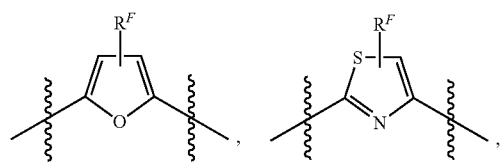

,

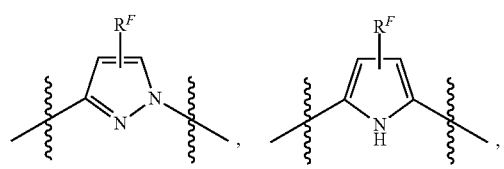

,

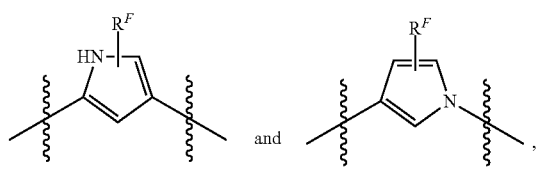

,

In some embodiments, the compound is of the formula (Ia-1):

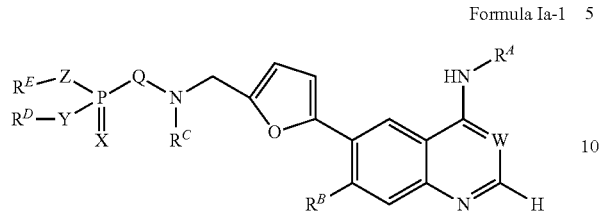

Formula Ia-1 wherein $R^A$, $R^B$, $R^C$, $R^D$, $R^E$, Q, W, X, Y, Z are as defined for Formula (I).

In another preferred embodiment, T of Formula I is an alkynyl group, and m is 1, as indicated in Formula Ib.

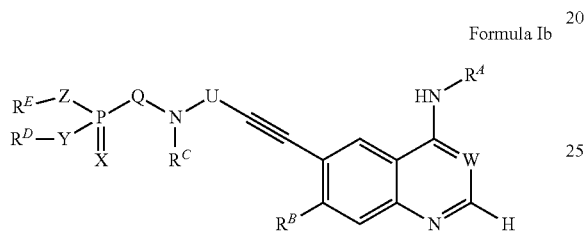

Formula Ib where $R^A$, $R^B$, Rc, $R^D$, $R^E$, X, Q, Y, Z, U are the same $R^A$, $R^B$, Rc, $R^D$, $R^E$, X, Q, Y, Z, U as defined above.

In yet another preferred embodiment, $R^B$ in Formula I or Formula Ia or Formula Ib is hydrogen or $-OR^5$; where $R^5$ is the same as $R^5$ as defined above;

In still another preferred embodiment, X in Formula I or Formula Ia or Formula Ib is O.

In a preferred embodiment, $A^3$ in Formula Ia is a carbon, and U is a methylene ($-CH_2-$) group, and is connected to the five-membered heterocycle through $A^3$.

Preferred examples of $R^A$ in Formula I or Formula Ia or Formula Ib include, but not limited to:

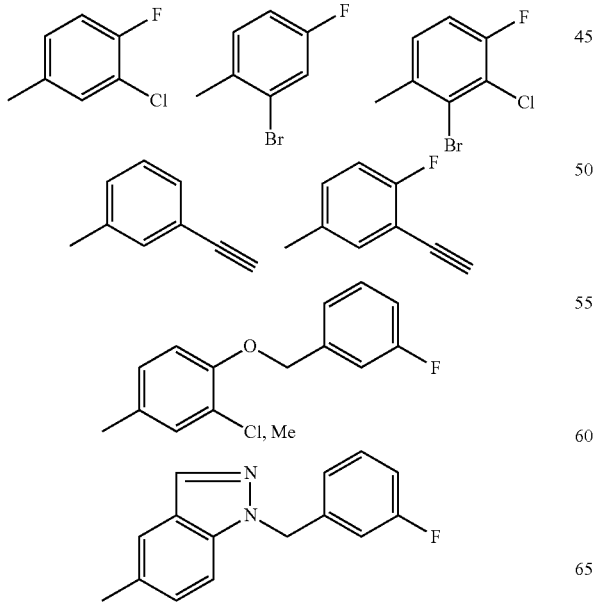

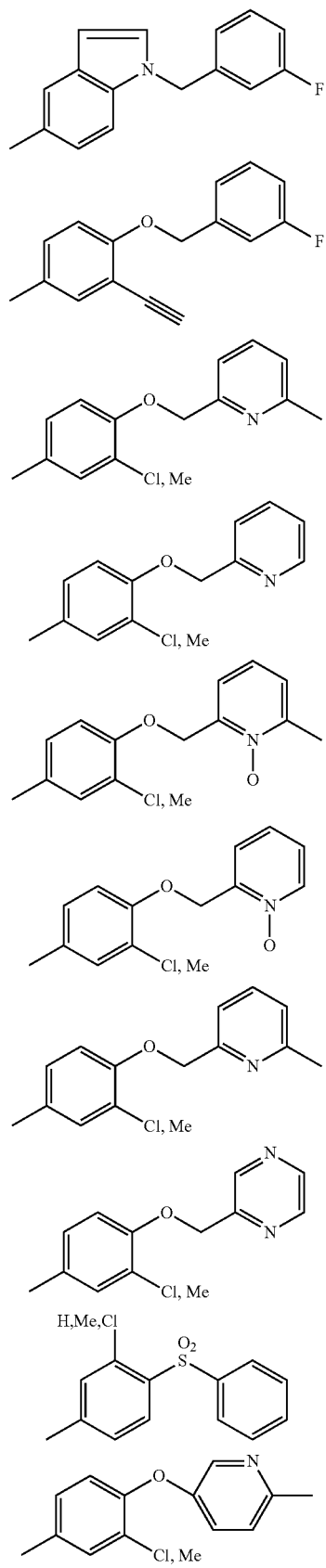

In some embodiments, the compound is selected from the group consisting of:

N-(3-chloro-4-(3-fluorobenzyloxy)phenyl)-6-(5-((4-methyl-1,4-azaphosphino-1-yl)methyl)furan-2-yl)quinazolin-4-amine;

6-(5-((2-(dimethylphosphino)ethylaminoyl)methyl)furan-2-yl)-N-(4-(3-fluorobenzyloxy)-3-chlorophenyl)quinazolin-4-amine;

6-(5-(((dimethylphosphinoyl)methylamino)methyl)furan-2-yl)-N-(4-(3-fluorobenzyloxy)-3-chlorophenyl)quinazolin-4-amine;

N-(3-chloro-4-(3-fluorobenzyloxy)phenyl)-6-(3-(4-methyl-1,4-azaphosphino-1-yl)prop-1-ynyl)quinazolin-4-amine;

N-(3-chloro-4-(3-fluorobenzyloxy)phenyl)-6-(3-(4-methyl-1,4-azaphosphino-1-yl)propyl)quinazolin-4-amine;

dimethyl 2-((5-(4-(3-chloro-4-(3-fluorobenzyloxy)phenylamino)quinazolin-6-yl)furan-2-yl)methylamino)ethylphosphonate;

N-(3-chloro-4-(3-fluorobenzyloxy)phenyl)-6-(5-((2-(5,5-dimethyl-1,3,2-dioxaphosphino-2-yl)ethylamino)methyl)furan-2-yl)quinazolin-4-amine;

N-(3-chloro-4-(pyridin-2-ylmethoxy)phenyl)-6-(5-((4-methyl-1,4-azaphosphino-1-yl)methyl)furan-2-yl)quinazolin-4-amine;

N-(3-chloro-4-((6-methylpyridin-2-yl)methoxy)phenyl)-6-(5-((4-methyl-1,4-azaphosphino-1-yl)methyl)furan-2-yl)quinazolin-4-amine;

6-(3-(2-(dimethylphosphinoyl)ethylamino)prop-1-ynyl)-N-(4-(3-fluorobenzyloxy)-3-chlorophenyl)quinazolin-4-amine;

N-(4-(3-fluorobenzyloxy)-3-chlorophenyl)-6-((E)-3-(4-methyl-1,4-azaphosphino-1-yl)prop-1-enyl)quinazolin-4-amine;

N-(4-(6-methylpyridin-3-yloxy)-3-methylphenyl)-6-(5-((4-methyl-1,4-azaphosphinan-1-yl)methyl)furan-2-yl)quinazolin-4-amine;

N-(4-(3-fluorobenzyloxy)-3-chlorophenyl)-6-(5-((4-((dimethylphosphinoyl)-methyl)piperazin-1-yl)methyl)furan-2-yl)quinazolin-4-amine;

N-(4-(3-fluorobenzyloxy)-3-bromophenyl)-6-(5-((4-methyl-1,4-azaphosphino-1-yl)methyl)furan-2-yl)quinazolin-4-amine;

2-((2-chloro-4-(6-(5-((4-methyl-1,4-azaphosphino-1-yl)methyl)furan-2-yl)quinazolin-4-ylamino)phenoxy)methyl)pyridine 1-oxide;

N-(1-(3-fluorobenzyl)-1H-indazol-5-yl)-6-(5-((4-methyl-1,4-azaphosphino-1-yl)methyl)furan-2-yl)quinazolin-4-amine;

N-(3-chloro-4-(3-fluorobenzyloxy)phenyl)-6-(5-((4-ethoxy-1,4-azaphosphino-1-yl)methyl)furan-2-yl)quinazolin-4-amine;

(R)-6-(5-((4-methyl-1,4-azaphosphino-1-yl)methyl)furan-2-yl)-N-(1-phenylethyl)quinazolin-4-amine;

N-(3-chloro-2-fluorophenyl)-6-(5-((4-methyl-1,4-azaphosphino-1-yl)methyl)furan-2-yl)quinazolin-4-amine;

N-(4-Bromo-2-fluorophenyl)-6-(5-((4-methyl-1,4-azaphosphino-1-yl)methyl)furan-2-yl)quinazolin-4-amine;

N-(4-Bromo-3-chloro-2-fluorophenyl)-6-(5-((4-methyl-1,4-azaphosphino-1-yl)methyl)furan-2-yl)quinazolin-4-amine;

N-(3-chloro-4-(pyrazin-2-ylmethoxy)phenyl)-6-(5-((4-methyl-1,4-azaphosphino-1-yl)methyl)furan-2-yl)quinazolin-4-amine;

N-(4-(3-fluorobenzyloxy)-3-ethynylphenyl)-6-(5-((4-methyl-1,4-azaphosphino-1-yl)methyl)furan-2-yl)quinazolin-4-amine;

2-((2-chloro-4-(6-(5-((4-methyl-1,4-azaphosphino-1-yl)methyl)furan-2-yl)quinazolin-4-ylamino)phenoxy)methyl)-6-methylpyridine 1-oxide;

6-(5-((2-(dimethylphosphinoyl)ethylamino)methyl)furan-2-yl)-N-(1-(3-fluorobenzyl)-1H-indazol-5-yl)quinazolin-4-amine;

2-(N-((5-(4-(1-(3-fluorobenzyl)-1H-indazol-5-ylamino)quinazolin-6-yl)furan-2-yl)methyl)-N-(2-(dimethylphosphino)ethyl)amino)ethane;

2-(N-((5-(4-(1-(3-fluorobenzyl)-1H-indazol-5-ylamino)quinazolin-6-yl)furan-2-yl)methyl)-N-(2-(dimethylphosphinoyl)ethyl)amino)ethanol; and N-(1-(3-fluorobenzyl)-1H-indazol-5-yl)-6-(3-(4-methyl-1,4-azaphosphino-1-yl)prop-1-ynyl)quinazolin-4-amine;

or a salt or solvate thereof.

In some embodiments, provided is a composition comprising a compound of the Formula (I), Formula (A), (Aa), (Aa-1), (Aa-2), (Ab), (Ab-1) or (Ac), or any variations thereof, a pharmaceutically acceptable salt thereof or a hydrate or solvate thereof, and a pharmaceutically acceptable carrier. Methods of making compounds of the Formula (I), Formula (A), (Aa), (Aa-1), (Aa-2), (Ab), (Ab-1) or (Ac), or any variations thereof, are also provided.

In another aspect, provided is a method of treating a hyperproliferative disease in a mammal (e.g. human), comprising administering to the mammal (e.g. human) a therapeutically effective amount of a compound of the Formula (I), Formula (A), (Aa), (Aa-1), (Aa-2), (Ab), (Ab-1) or (Ac), or any variations thereof, or a salt or solvate thereof. In some embodiments, the method is for the treatment of a Her2 positive cancer in a mammal (e.g. human). In some embodiments, the Her2 positive cancer is breast cancer, gastric cancer, ovarian cancer.

Also provided is the use of a compound of the Formula (I), Formula (A), (Aa), (Aa-1), (Aa-2), (Ab), (Ab-1) or (Ac), or any variations thereof, in the manufacture of a medicament for the treatment of a hyperproliferative disease, such as a Her2 positive cancer in human (e.g. breast cancer, gastric cancer, ovarian cancer).

Also provided is a kit comprising a compound of the Formula (I), Formula (A), (Aa), (Aa-1), (Aa-2), (Ab), (Ab-1) or (Ac), or any variations thereof, and instructions for use in the treatment of a hyperproliferative disease, such as a Her2 positive cancer in human (e.g. breast cancer, gastric cancer, ovarian cancer).

The invention may also be directed to pharmaceutically acceptable salts, pharmaceutically acceptable prodrugs, and pharmaceutically active metabolites of the compound of general Formula I. Methods of making the compounds of Formula I are also described.

In a further aspect, the present invention provides compounds that inhibit the activity of ErbB family receptor tyrosine kinases, comprising compounds of the Formula (I), Formula (A), (Aa), (Aa-1), (Aa-2), (Ab), (Ab-1) or (Ac), or any variations thereof.

In a further aspect, the present invention provides a method of treating diseases or medical conditions mediated by type I receptor tyrosine kinases which comprises administering to mammals an effective amount of a compound of the Formula (I), Formula (A), (Aa), (Aa-1), (Aa-2), (Ab), (Ab-1) or (Ac), or any variations thereof, or a pharmaceutically acceptable salt, solvate or in vivo transformable prodrug thereof. The type I receptor tyrosine kinase mediated condition that can be treated according to the methods of this invention includes hyperproliferative disorders, such as cancer of the head and neck, lung, breast, colon, ovary, bladder, stomach, kidney, skin, pancreas, leukemias, lymphomas, esophagus, uterus or prostate, among other kinds of hyperproliferative disorders.

The compounds of the Formula (I), Formula (A), (Aa), (Aa-1), (Aa-2), (Ab), (Ab-1) or (Ac), or any variations thereof, may be used advantageously in combination with other known therapeutic agents.

The invention also relates to pharmaceutical compositions comprising an effective amount of an agent selected from compounds of Formula I or a pharmaceutically acceptable prodrug, pharmaceutically active metabolite, or pharmaceutically acceptable salt thereof.

The invention also includes all salts, solvates, and physiologically functional derivatives of compounds of the Formula (I), Formula (A), (Aa), (Aa-1), (Aa-2), (Ab), (Ab-1) or (Ac), or any variations described herein, such as pharmaceutically acceptable salts and prodrugs. The invention also includes any or all of the stereochemical forms, including any enantiomeric or diasteriomeric forms, and any tautomers or other forms of the compounds described. Unless stereochemistry is explicitly indicated in a chemical structure or name, the structure or name is intended to embrace all possible stereoisomers of a compound depicted. In addition, where a specific stereochemical form is depicted, it is understood that other stereochemical forms are also embraced by the invention. All forms of the compounds are also embraced by the invention, such as crystalline or non-crystalline forms of the compounds. Compositions comprising a compound of the invention are also intended, such as a composition of substantially pure compound, including a specific stereochemical form thereof. Compositions comprising a mixture of compounds of the invention in any ratio are also embraced by the invention, including mixtures of two or more stereochemical forms of a compound of the invention in any ratio, such that racemic, non-racemic, enantioenriched and scalemic mixtures of a compound are embraced.

The present invention also includes isotopically-labeled compounds of the Formula (I), Formula (A), (Aa), (Aa-1), (Aa-2), (Ab), (Ab-1) or (Ac), or any variations described herein. The isotopically labeled compounds are identical to the compounds of this invention, but for the faction one or more atoms are replaced by an isotope of the same element. Exemplary isotopes that can be incorporated into compounds of the invention include isotopes of hydrogen, carbon, nitrogen, oxygen, phosphorus, sulfur, chlorine, such as $^2$H, $^3$H, $^{11}$C, $^{13}$C, $^{14}$C $^{13}$N, $^{15}$O, $^{17}$O, $^{32}$P, $^{35}$S, $^{18}$F, $^{36}$Cl. Certain isotope labeled compounds (e.g. $^3$H and $^{14}$C) are useful in compound or substrate tissue distribution study. Wherein certain heavier isotope (e.g. $^2$H) may afford certain therapeutical advantage resulting from possible greater metabolic stability.

The compounds of this invention may possess one or more asymmetric centers, and such compounds can be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. Accordingly, this invention also includes racemates and resolved enantiomers, and diastereomers compounds of the Formula I. The methods for the determination of stereochemistry and the separation of stereoisomers are well known in the art (see discussion in Chapter 4 of "March's Advanced Organic Chemistry", 6th edition M. B. Smith and J. March, John Wiley and Sons, New York, 2007).

In addition to compounds of the Formula I, the invention also includes solvates, pharmaceutically acceptable prodrugs, pharmaceutically active metabolites, and pharmaceutically acceptable salts of such compounds.

The term "solvate" refers to an aggregate of a molecule with one or more solvent molecules.

A "pharmaceutically acceptable prodrug" is a compound that may be converted under physiological conditions or by solvolysis to the specified compound or to a pharmaceutically acceptable salt of such compound.

A "pharmaceutically active metabolite" is a pharmacologically active product produced through metabolism in the body of a specified compound or salt thereof. Metabolites of a compound may be identified using routine techniques known in the art and their activities determined using tests such as those described herein.

Prodrugs and active metabolites of a compound may be identified using routine techniques known in the art. Various forms of prodrugs are known in the art. For examples of such prodrug derivatives, see, for example, a) *Design of Prodrugs*, edited by H. Bundgaard, (Elsevier, 1985) and *Methods in Enzymology*, Vol. 42, p. 309-396, edited by K. Widder, et al. (Academic Press, 1985); b) Chapter 27, *"Recent Advances in Oral Prodrug Discovery"*, A. Cho in *Annual Reports in Medicinal Chemistry*, edited by A. Wood (Academic Press, 2006), 41:395. c) *Prodrugs: Challenges and Rewards, Part* 1 *and* 2, edited by V. J. Stella, et al. (Springer, 2007).

A "pharmaceutically acceptable salt" is a salt that retains the biological effectiveness of the free acids and bases of the specified compound and that is not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable sale. Examples of pharmaceutically acceptable salts include those salts prepared by reaction of the compounds of the present invention with a mineral or organic acid or an inorganic base, such salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyn-1,4-dioates, hexyne-1,6-dioates, benzoates, chlorobenzoates, methylbenzoates, dinitromenzoates, hydroxybenzoates, methoxybenzoates, phthalates, sulfonates, xylenesulfonates, pheylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, tosylates, besylates, acetate and mandelates.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid such as glucuronic acid or galacturonic acid, an alphahydroxy acid such as citric acid or tartaric acid, an amino acid such as aspartic acid or glutamic acid, an aromatic acid such as benzoic acid or cinnamic acid, a sulfonic acid such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The inventive compounds may be prepared using the reaction routes and synthesis schemes as described below, employing the techniques available in the art using starting materials that are readily available.

Preparation

A compound of Formula I, or a pharmaceutically acceptable salt thereof, may be prepared by any process known to be applicable to the preparation of chemically related compounds. Suitable processes include, for example, those illustrated in WO2001/004111, and in Mastalerz, Harold, et al, *Bioorganic Medicinal Chemistry Letters,* 2007, 17, 4947. Such processes, when used to prepare compounds of the Formula I are provided as a further feature of the invention, and the groups $A^1, A^2, A^3, A^4, A^5, R^B, R^C, R^D, R^E, Y, Z, U$ are defined the same as above. Necessary starting materials may be obtained by standard procedures of synthetic organic chemistry. The preparation of such starting materials is described in conjunction with the following representative processes and within the accompanying Examples. Alternatively, the necessary starting materials can be obtained by analogous procedures to the illustrated, which are within the ordinary skill of an organic chemist.

The following synthetic schemes are meant to be representative examples only and are not mean to limit the invention in any way.

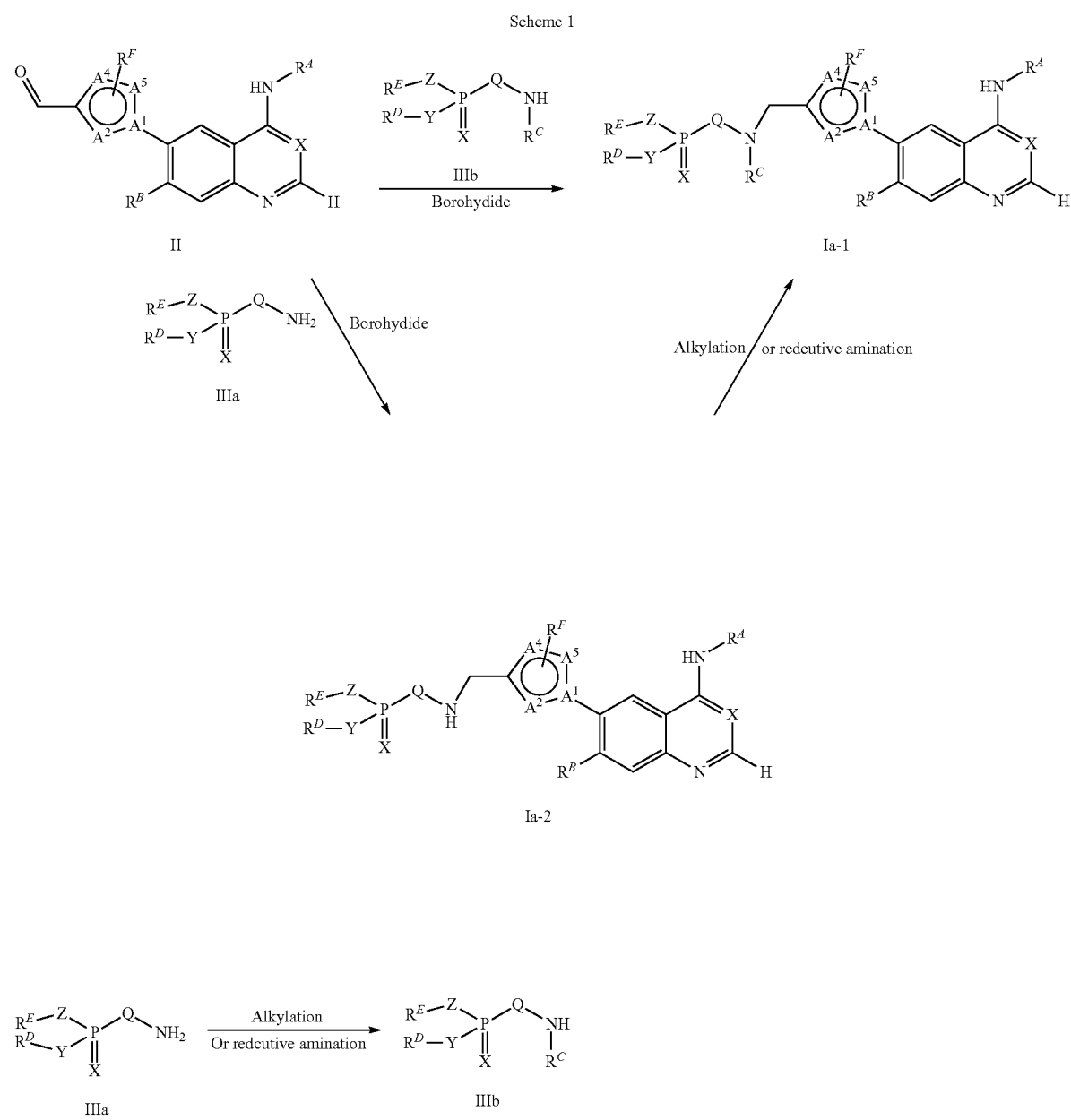

Scheme 1 shows a representative preparation of a compound of Formula Ia. Reductive amination between compounds of Formula II and compounds of either formula Ma or formula Mb affords a compound of Formula Ia-2 or Formula Ia-1. In a further prospective, compounds of formula Ia-2 can be alkylated with an alkylating reagent, such as $R^C I$ or $R^C IBr$ to yield compounds of formula Ia-1. Alternatively, compounds of Formula Ia-2 can undergo reductive amination with an aldehyde to afford compounds of Formula Ia-1. The borohydride used for reductive amination can be sodium triacetoxylboronhydride or sodium cyanoborohydride, solvent can be dichloromethane, or tetrahydrofuran (THF), or an alcoholic solvent (e.g. ethanol). The reaction is typically carried out at ambient temperature.

The compounds of general Formula II can be prepared by the procedures described in pulished PCT application number WO2001/004111.

Compounds of Formula IIIb may be prepared from compounds of Formula IIIa via alkylation with $R^C$-halide (preferred halide for the transformation is Br or I). Alternatively, reductive amination with appropriate aldehydes also converts compounds of Formula IIIa to compounds of Formula IIIb. The borohydride used for reductive amination in Scheme 2 can be sodium triacetoxylboronhydride or sodium cyanoborohydride, solvent can be dichloromethane, or tetrahydrofuran (THF), or an alcoholic solvent (e.g. ethanol). The reaction is typically carried out at ambient temperature.

VII or Formula VIII, and the resulting intermediates are deprotected to give compounds of Formula IIIa-2 or Formula IIIa-3.

Groups $R^D$, $R^E$, Q, Y, Z in Scheme 2 are defined the same as above. $R^G$ is the same as $R^F$, as defined above, where n is integer selected from 0-3. "M" is a metal, represented by but not limited to magnesium (as MgCl or MgBr or MgI), sodium, potassium, lithium, Zinc (as ZnCl or ZnBr or ZnI), Cu, and cesium. The linker connecting "Y" and "Z" in compounds' of Formula VII or Formula IIIB-2 is a alkyl or heteroaldkyl diraticals, and may contains 0-3 heteroatoms (e.g. $NR^1$, O, S), which may be further substituted or oxidized. Compounds of Formula IIIc-1, or Formula IIIa-2, or Formula IIIa-3 are sub-class of compounds of Formula IIIa.

Scheme 3

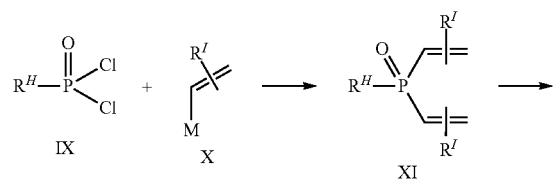

Scheme 2

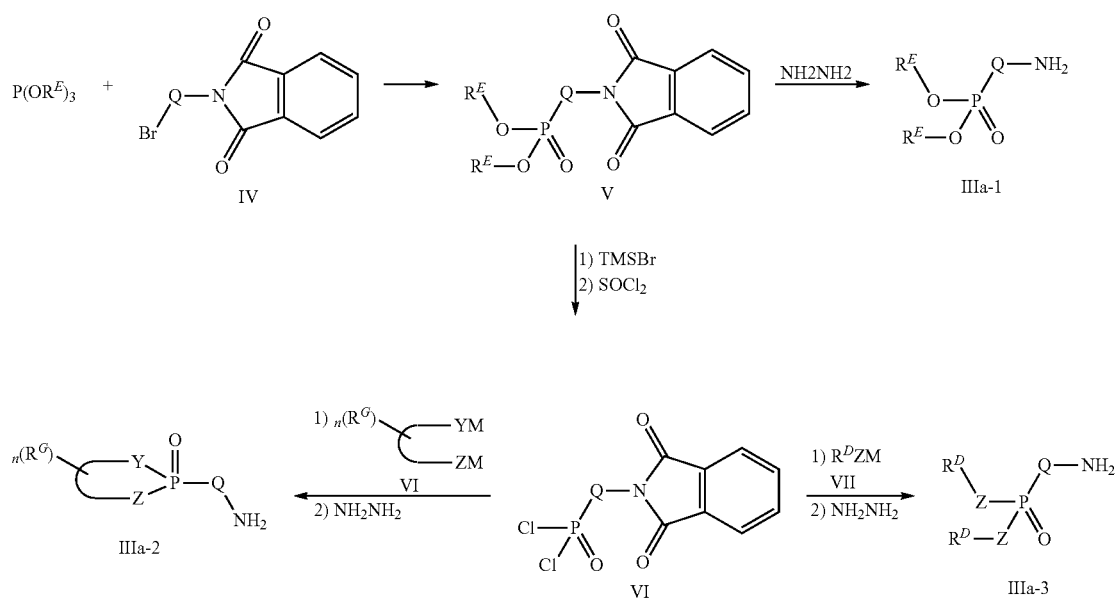

Representative preparations of compounds related to Formula IIIa are shown in Scheme 2. Trialkyl phosphites are reacted with bromide of formula IV at temperature 80 to 150° C. in an appropriate solvent or in neat. Deprotection of the resulting compounds of Formula V affords compounds of Formula IIIc-1.

Alternatively, compounds of Formula V can be deprotected with trimethylsilyl bromide (TMSBr), and the resulting intermediates are converted to phosphonyl chlorides of formula VI when refluxed with thionyl chloride. The phosphonyl chlorides of Formula VI are reacted with compounds of Formula -continued

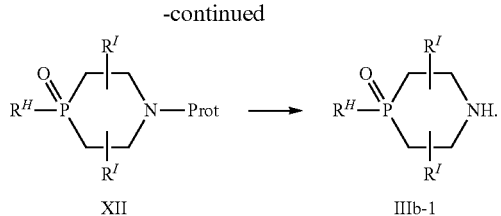

A representative preparation of cyclic secondary amines of Formula IIIb-1 is shown in Scheme 3. Formula IIIb-1 is a sub-class of Formula Mb. Reaction of a phosphoryl dichloride of Formula IX with 2 equivalents of alkenylmetal (e.g. alkenyl Grignard reagents or alkenyllithium reagents) of Formula X give dialkenylphosphorus compounds of Formula. XI. Aza-Michael addition of aa appropriate protected amine (e.g. benzylamine) afford compounds of Formula XII. Deprotection (e.g. hydrogenolysis with hydrogen at about 50 psi) afford compounds of Formula IIIb-1.

$R^H$ and $R^I$ is independently selected from a group of $C_1$-$C_6$ alkyl, $C_3$-$C_6$ cycloalkyl, $C_3$-$C_6$ cycloalkylalkyl, heterocyclyl, heterocyclylalkyl, aryl, heteroaryl, arylalkyl and heteroarylalkyl, —$OR^5$; $R^5$ is defined the same as above. M is a metal, and is the same as "M" as defined above.

Therapeutic Aspects of the Invention

Therapeutically effective amounts of the compounds of the invention may be used to treat diseases mediated by modulation or regulation of ErbB family kinases. An "effective amount" is intended to mean that amount of compound that, when administered to a mammal in need of such treatment, is sufficient to effect treatment for a disease mediated by the activity of one or more ErbB family kinases. Thus, for example, a therapeutically effective amount of a compound selected from Formula I or a salt, active metabolite or prodrug thereof, is a quantity sufficient to modulate, regulate, or inhibit the activity of one or more ErbB family kinases such that a disease condition which is mediated by that activity is reduced or alleviated.

The amount of a given agent that will correspond to such an amount will vary depending upon factors such as the particular compound, disease condition and its severity, the identity (e.g., weight) of the mammal in need of treatment, but can nevertheless be routinely determined by one skilled in the art. "Treating" is intended to mean at least the mitigation of a disease condition in a mammal, such as a human, that is affected, at least in part, by the activity of one or more ErbB family tyrosine kinases and/or serine, threonine kinases, and includes, but is not limited to, preventing the disease condition from occurring in a mammal, particularly when the mammal is found to be predisposed to having the disease condition but has not yet been diagnosed as having it; modulating and/or inhibiting the disease condition; and/or alleviating the disease condition.

In order to use a compound of the Formula I, or a pharmaceutically acceptable salt or in vivo cleavable prodrug thereof, for the therapeutic treatment (including prophylactic treatment) of mammals including humans, it is normally formulated in accordance with standard pharmaceutical practice as a pharmaceutical composition. According to this aspect of the invention there is provided a pharmaceutical composition that comprises a compound of the Formula I, or a pharmaceutically acceptable salt or in vivo cleavable prodrug thereof, as defined hereinbefore in association with a pharmaceutically acceptable diluent or carrier.

The compositions of the invention may be in a form suitable for oral use (for example as tablets, lozenges, capsules, suspensions, emulsions, dispersible powders or granules, syrups or elixirs), for topical use (for example as creams, ointments, gels, or aqueous or oily solutions or suspensions), for inhalation (for example as a finely divided powder or a liquid aerosol), for administration by insufflation (for example as a finely divided powder) or for parenteral administration (for example as a sterile aqueous or oily solution for intravenous, subcutaneous, or intramuscular dosing or as a suppository for rectal dosing). For example, compositions intended for oral use may contain one or more coloring, sweetening, flavoring and/or preservative agents.

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or oil such as peanut oil, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), coloring agents, flavoring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent, and one or more preservatives. Suitable dispersing or wetting agents and suspending agents are exemplified by those already mentioned above. Additional excipients such as sweetening, flavoring and coloring agents, may also be present.

The pharmaceutical compositions of the invention may also be in the form of oil-in-water emulsions. The oily phase may be a vegetable oil, such as olive oil or arachis oil, or a mineral oil such as liquid paraffin, or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient, which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedures well known in the art.

Compositions for administration by insufflation may be in the form of a finely divided powder containing particles of average diameter of, for example, 30 μm or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

The amount of a compound of this invention that is combined with one or more excipients to produce a single dosage form will necessarily vary depending upon the host treated and the particular route of administration. For example, a formulation intended for oral administration to humans may contain, for example, from 0.5 mg to 5 g of active agent compounded with an appropriate and convenient amount of excipients, which may vary from about 5 to about 98 percent by weight of the total composition. Dosage unit forms will generally contain about 1 mg to about 500 mg of an active ingredient. For further information on routes of administration and dosage regimes, see: *Ansel's Pharmaceutical Dosage Forms and Drug Delivery Systems*, by Loyd V. Allen, Howard C. Ansel, Nicholas G. Popovich, Lippincott Williams & Wilkins, 2004.

The size of the dose for therapeutic or prophylactic purposes of a compound of Formula I will naturally vary according to the nature and severity of the conditions, the age and sex of the animal or patient and the route of administration, according to well known principles of medicine.

The compounds of the invention are administered either singly or in combination to a mammal to treat hyperproliferative disease, such as various types of cancer, e.g., cancer of the colon, ovary, bladder, stomach, lung, uterus, and prostate. The compound may be administered via any acceptable route, e.g., intra venous, oral, intra muscular, via suppository, etc. The compounds can be formulated as oral dosage forms, e.g., tablets, capsules, liquid suspension, etc, as suppositories, or may be prepared as a liquid for injection, for example. The skilled practitioner can select the appropriate route and dosage amount for treatment of the specific hyperproliferative disease to be treated.

The examples below are intended to illustrate embodiments of the invention, and are not intended to limit the scope of the specification or claims in any way.

Example 1

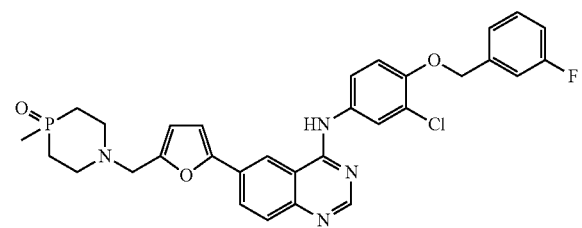 [SMILES: CP1(=O)CCN(Cc2ccc(-c3ccc4ncnc(Nc5ccc(OCc6cccc(F)c6)c(Cl)c5)c4c3)o2)CC1]

N-(3-chloro-4-(3-fluorobenzyloxy)phenyl)-6-(5-((4-methyl-1,4-azaphosphino-1-yl)methyl)furan-2-yl)quinazolin-4-amine Step A: 1-benzyl-4-methyl-1,4-azaphosphinane 4-oxide (compound 1.1)

To a vigorously stirred solution of methylphosphonic dichloride (6.65 g, 50 mmol) in THF (100 mL) at −78° C. was added vinylmagnesium chloride (1.6 M in THF, 66 mL, 105 mmol) dropwisely over 30 min. After the addition is completed, the reaction mixture was warmed to 0° C. over 1 hour, and to it was added benzylamine (6.43 g, 60 mmol) and methanol (100 mL). The reaction mixture was then refluxed for 36 hours. After cooled to room temperature, the reaction mixture was poured into a separation funnel containing saturated aqueous ammonium chloride (100 mL), ethyl acetate (200 mL) and water (100 mL). The organic layer was separated, and the aqueous layer was extracted with methylene chloride (100 mL) twice. The combined organic layer and extracts were dried over anhydrous magnesium sulfate, filtered and concentrated. The residue was purified by flash chromatography, eluting with 20% methanol in dichloromethane to give the desired product as white crystalline solid (5.69 g, 51%). LCMS ESI(+) m/z: 224 (M+1).

Step B: 4-methyl-1,4-azaphosphinane 4-oxide hydrogen chloride salt (compound 1.2)

A solution of 1-benzyl-4-methyl-1,4-azaphosphinane 4-oxide (5 g) in methanol (50 mL) and 3 M HCl (10 mL) with palladium on carbon (10%, 1.0 g) was hydrogenated on a Parr shaker for 24 hours at 60 psi. The mixture was filtered through Celite and all solvents were removed under reduced pressure to give a white crystalline solid, which was used without further purification.

Step C: 6-Iodo-4-quinazolinone (compound 1.3)

A solution of 2-amino-5-iodobenzoic acid (14.2 g, 50 mmol) and formamide (100 mL) was refluxed for 10 hours.

After cooling to room temperature, water (100 mL) was added. The solid product was collected by filtration, washed with water. Further drying in a vacuum provided 6-Iodo-4-quinazolinone (11 g, 81%) as a gray solid.

Step D: 4-chloro-6-iodoquinazoline (compound 1.4)

To a solution of 6-Iodo-quinazolin-4-ol (5.0 g, 18 mmol) in thionyl chloride (10 mL) was added slowly DMF (0.5 mL) and the mixture is heated immediately to reflux. Heating is continued for 4.5 hours, followed by cooling to room temperature. The reaction mixture was then evaporated under reduced pressure to dryness. The residue was then redesolved in DCM (20 mL), and to it was added toluene (50 mL), and the mixture was then evaporated under reduced pressure to dryness. The procedure was repeated one more time to rid the product of thionyl chloride to yield 5.2 g (99%) of desired product as a tan solid.

Step E:
3-chloro-4-(3-fluoro-benzyloxy)-phenylamine (compound 1.5)

Sodium hydride (60% dispersion in oil, 1.4 g, 33.5 mmol) was suspended in anhydrous THF (50 ml) under nitrogen and the resulting mixture is cooled to 0° C. To above suspension was added dropwisely (3-Fluoro-phenyl)-methanol (2.90 ml, 27 mmol), followed by a solution of 2-chloro-1-fluoro-4-nitro-benzene (4.2 g, 24 mmol) in dry DMF (20 ml). The reaction mixture was then stirred at room temperature for another 4 hours. The reaction mixture concentrated under vacuum to about 40 mL, and was poured into 200 ml of ice:water. The resultant solid was isolated by filtration, washed with water (50 ml), and air dried to yield a yellow solid, 2-Chloro-1-(3-fluoro-benzyloxy)-4-nitro-benzene (5.8 g). The solid was suspended in MeOH (50 ml) and treated wet 5% Pt/C (Degussa type, Aldrich, 1.5 g). The flask is flushed with hydrogen gas from a balloon and the reaction mixture was stirred under hydrogen balloon for 2 hours. The reaction mixture was filtered through a Celite plug and the solvent is removed under reduced pressure to yield 5.2 g of the desired product.

Step F: [3-chloro-4-(3-fluoro-benzyloxy)-phenyl]-(6-iodo-quinazolin-4-yl)-amine hydrochloride salt (compound 1.6)

3-Chloro-4-(3-fluoro-benzyloxy)-phenylamine (3.1 g, 12 mmol) and 4-chloro-6-iodo-quinazoline (3.28 g, 11.3 mmol) were dissolved in isopropanol (50 ml). The reaction mixture was refluxed for 12 hours. The solid product was collected by filtration, washed with cold isopropanol (10 mL) and ether (20 mL), and air dried to afford 3.8 g of the clean desired material.

Step G: 5-(4-(3-chloro-4-(3-fluorobenzyloxy)phenylamino)quinazolin-6-yl)furan-2-carbaldehyde (compound 1.7)

A mixture of [3-chloro-4-(3-fluoro-benzyloxy)-phenyl]-(6-iodo-quinazolin-4-yl)-amine hydrochloride salt (5.05 g, 10 mmol), 2-furylboronic acid (1.85 g, 12 mmol) and palladium catalyst (730 mg, 1.0 mmol) in 10 mL of $K_2CO_3$ (2.0M), 10 mL of EtOH and 40 mL of DME was heated at 75° C. under nitrogen atmosphere for 4 hr. LS-MS showed the reaction completed. Concentrated the mixture under reduced pressure and washed the residue with water (2×50 mL) then with cool ether (100 mL) to get a gray solid (4.5 g), which was used for next step without further purification.

Step H: N-(3-chloro-4-(3-fluorobenzyloxy)phenyl)-6-(5-((4-methyl-1,4-azaphosphino-1-yl)methyl)furan-2-yl)quinazolin-4-amine (compound 1)

To a suspension of compound 1.2 (169 mg, 1 mmol) and the compound 1.7 from step G (473 mg, 1 mmol) in DCE (5 mL) was added DIPEA (1.5 mmol) and HOAc (1.5 mmol). After stirring the mixture for 30 minutes, 2.0 mmol of NaBH(OAc)$_3$ was added followed by Stirring the mixture overnight. 1.0 mL of 5M NaOH was added and the mixture was extracted with DCM (2×20 mL). Combined organics was washed with brine and dried over MgSO$_4$. Filtration and concentration followed by purification through flash column chromatography on silica gel (10% methanol in DCM) to get pale brown powder. $^1$H NMR (CD$_3$OD, 300 MHz) δ 8.67 (d, 1H), 8.49 (s, 1H), 8.18 (dd, 1H), 7.91 (d, 1H), 7.63 (dd, 1H), 7.42 (td, 1H), 7.32 (d, 1H), 7.27 (dd, 1H), 7.17 (d, 1H), 7.07 (td, 1H), 6.98 (d, 1H), 6.51 (d, 1H), 6.51 (d, 1H), 5.23 (s, 2H), 3.82 (s, 2H), 3.36 (s, 1H), 3.05 (m, 2H), 2.90 (m, 2H), 2.04 (m, 4H), 1.58 (d, 3H). LCMS ESI(+) m/z: 591 (M+1).

Example 2

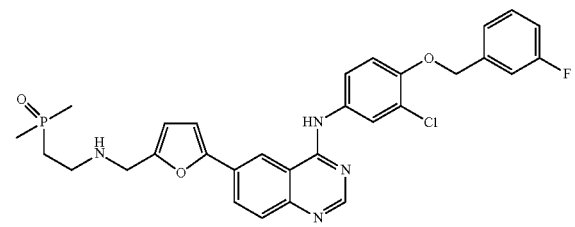 [SMILES: CP(C)(=O)CCNCc1ccc(-c2ccc3ncnc(Nc4ccc(OCc5cccc(F)c5)c(Cl)c4)c3c2)o1]

6-(5-((2-(dimethylphosphino)ethylaminoyl)methyl)furan-2-yl)-N-(4-(3-fluorobenzyloxy)-3-chlorophenyl)quinazolin-4-amine Step A:
N-benzyl-2-(dimethylphosphinoyl)ethanamine (compound 2.1)

To a vigorously stirred solution of dimethylphosphonic chloride (6.65 g, 50 mmol) in THF (100 mL) at −78° C. was added vinylmagnesium chloride (1.6 M in THF, 33 mL, 52.5 mmol) dropwisely over 30 min. After the addition is completed, the reaction mixture was warmed to 0° C. over 1 hour, and to it was added benzylamine (6.43 g, 30 mmol) and methanol (100 mL). The reaction mixture was then refluxed for 36 hours. After cooled to room temperature, the solvent was removed and the residue was poured into a separation funnel containing ethyl acetate (200 mL) and water (100 mL). The organic layer was separated, and the aqueous layer was extracted with methylene chloride (100 mL) twice. The combined organic layer and extracts were dried over anhydrous magnesium sulfate, filtered and concentrated. The residue was purified by flash chromatography, eluting with 20% methanol in dichloromethane to give the desired product as white crystalline solid (5.69 g, 51%). LCMS ESI(+) m/z: 224 (M+1).

Step B: 2-(dimethylphosphinoyl)ethanamine (compound 2.2)

A solution of compound 2.2 (200 mg) in methanol (50 mL) with palladium on carbon (10%, 50 mg) was hydrogenated on a Parr shaker for 24 hours at 60 psi. The mixture was filtered through Celite and all solvents were removed under reduced pressure to give a white crystalline solid, which was used without further purification. LCMS ESI(+) m/z: 122 (M+1).

Step C: 6-(5-((2-(dimethylphosphino)ethylaminoyl)methyl)furan-2-yl)-N-(4-(3-fluorobenzyloxy)-3-chlorophenyl)quinazolin-4-amine (compound 2)

5-(4-(4-(3-fluorobenzyloxy)-3-chlorophenylamino)quinazolin-6-yl)furan-2-carbaldehyde and 2-(dimethylphosphinoyl)ethanamine (compound 2.2) were suspended in dichloromethane (20 mL). Sequentially, acetic acid (3 drops) and sodium triacetoxyborohydride (2 equiv.) were added at room temperature. The mixture was stirred at room temperature until the starting material disappeared. The reaction was quenched with 2N NaOH aqueous solution and extracted with dichloromethane. The combined organic layer and extracts were dried over anhydrous magnesium sulfate, filtered and concentrated. The residue was purified by flash chromatography, eluting with 20% methanol in dichloromethane to give the desired product as yellow crystalline solid. LCMS ESI(+) m/z: 580 (M+1). $^1$H NMR (300 MHz, CD$_3$OD) δ 8.73 (d, 1H), 8.50 (s, 1H): 8.20 (m, 1H), 7.92 (d, 1H), 7.80 (m, 1H), 7.68 (m, 1H), 7.46 (m, 1H), 7.36 (m, 1H), 7.30 (m, 1H), 7.22 (m, 1H), 7.11 (m, 1H), 7.00 (d, 1H), 6.53 (d, 1H), 5.25 (s, 2H), 3.94 (s, 2H), 3.08 (m, 2H), 2.15 (m, 2H), 1.57 (s, 3H), 1.53 (s, 3H).

Example 3

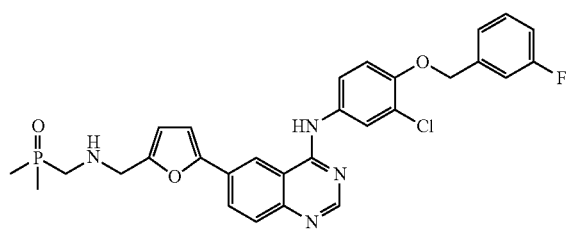 [SMILES: CP(C)(=O)CNCc1ccc(-c2ccc3ncnc(Nc4ccc(OCc5cccc(F)c5)c(Cl)c4)c3c2)o1]

6-(5-(((dimethylphosphinoyl)methylamino)methyl)furan-2-yl)-N-(4-(3-fluorobenzyloxy)-3-chlorophenyl)quinazolin-4-amine 5-(4-(4-(3-fluorobenzyloxy)-3-chlorophenylamino)quinazolin-6-yl)furan-2-carbaldehyde (compound 1.7) and (dimethylphosphinoyl)methanamine (preparation: Maier, Ludwig *Phosphorus, Sulfur and Silicon and the Related Elements*, 53(1-4), 43-67; 1990) were suspended in dichloromethane (20 mL). Sequentially, acetic acid (3 drops) and sodium triacetoxyborohydride (2 equiv.) were added at room temperature. The mixture was stirred at room temperature until the starting material disappeared. The reaction was quenched with 2N NaOH aqueous solution and extracted with dichloromethane. The combined organic layer and extracts were dried over anhydrous magnesium sulfate, filtered and concentrated. The residue was purified by flash chromatography, eluting with 20% methanol in dichloromethane to give the desired product as yellow crystalline solid. LCMS ESI(+) m/z: 566 (M+1). $^1$H NMR (300 MHz, CD$_3$OD) δ 8.65 (s, 1H), 8.46 (s, 1H), 8.15 (m, 1H), 7.91 (d, 1H), 7.75 (m, 1H), 7.62 (m, 1H), 7.40 (m, 1H), 7.29 (m, 1H), 7.26 (m, 1H), 7.13 (m, 1H), 7.08 (m, 1H), 6.93 (d, 1H), 6.47 (d, 1H), 5.20 (s, 2H), 3.97 (s, 2H), 3.08 (m, 2H), 2.85 (m, 1H), 1.57 (m, 6H).

Example 4

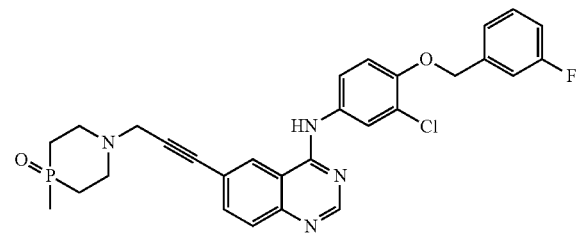 [SMILES: CP1(=O)CCN(CC#Cc2ccc3ncnc(Nc4ccc(OCc5cccc(F)c5)c(Cl)c4)c3c2)CC1]

N-(3-chloro-4-(3-fluorobenzyloxy)phenyl)-6-(3-(4-methyl-1,4-azaphosphino-1-yl)prop-1-ynyl)quinazolin-4-amine

Step A: 4-methyl-1-(prop-2-ynyl)-1,4-azaphosphinane, 4-oxide (compound 4.1)

To a mixture of Cs$_2$CO$_3$ (1.3 g, 4.0 mmol), Acetone (5.0 mL) and compound 1.2 (0.338 mg, 2.0 mmol) was added propargyl chloride (150 mg, 2.0 mmol). Stirred the mixture at 50° C. overnight. Filtration and concentration afforded a yale brown solid. No further purification was needed for next step.

Step B: N-(3-chloro-4-(3-fluorobenzyloxy)phenyl)-6-(3-(4-methyl-1,4-azaphosphino-1-yl)prop-1-ynyl)quinazolin-4-amine (compound 4)

A mixture of the amine, compound 4.1 (205 mg, 1.2 mmol), Iodide, compound 1.6 (505 mg, 1.0 mmol), PdCl$_2$(PPh$_3$)$_2$ (35 mg, 5% mol), Et$_3$N (1.0 mL) and CuI (64 mg, 20% mol) in 10 mL of DMF was heated at under N$_2$ atmosphere overnight. Concentration and purification through flash column chromatography on silica gel (5% MeOH in DCM) afforded the desirable product as brown powder. LCMS ESI (+) m/z: 550 (M+1). $^1$H NMR (CD$_3$OD, 300 MHz) δ 7.96 (d, J=2.4 Hz, 1H), 7.83 (dd, J1=3.6 Hz, J2=8.1 Hz, 1H), 7.71 (d, J=8.4 Hz, 1H), 7.60 (dd, J1=2.7 Hz, J2=9.3 Hz, 1H), 7.39 (td, J1=0.7 Hz, J2=7.5 Hz, 1H), 7.29 (d, J=7.5 Hz, 1H), 7.24 (d, J=9.9 Hz, 1H), 7.13 (d, J=9.0 Hz, 1H), 7.05

(td, J1=1.8 Hz, J2=8.1 Hz, 1H), 5.21 (s, 2H), 3.73 (s, 2H), 3.35 (s, 1H), 3.20 (m, 2H), 3.00 (m, 2H), 2.00 (m, 4H), 1.62 (d, J=13.2 Hz, 3H).

Example 5

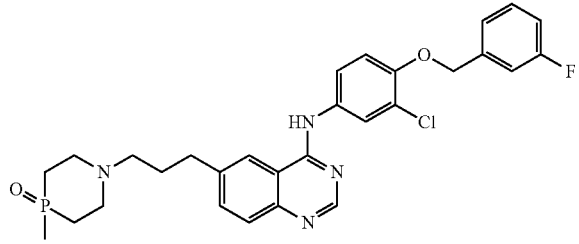 [SMILES: CP1(=O)CCN(CCCc2ccc3ncnc(Nc4ccc(OCc5cccc(F)c5)c(Cl)c4)c3c2)CC1]

N-(3-chloro-4-(3-fluorobenzyloxy)phenyl)-6-(3-(4-methyl-1,4-azaphosphino-1-yl)propyl)quinazolin-4-amine A mixture of the triple bond compound (compound 4, 100 mg, 0.18 mmol) and 10% Pd—C (10 mg) in MeOH (20 mL) under $H_2$ atmosphere at room temperature for three hours. Filtration and concentration followed purification through flash column chromatography on silica gel (5% MeOH in DCM) afforded the desirable product as a brown powder. LCMS ESI(+) m/z: 554 (M+1). $^1$H NMR (CD$_3$OD, 300 MHz) δ 8.46 (s, 1H), 8.18 (s, 1H), 7.88 (d, J=2.7 Hz, 1H), 7.75 (dd, J1=1.2 Hz, J2=8.7 Hz, 1H), 7.71 (d, J=8.4 Hz, 1H), 7.58 (dd, J1=2.7 Hz, J2=9.0 Hz, 1H), 7.39 (td, J1=0.7 Hz, J2=7.5 Hz, 1H), 7.29 (d, J=7.5 Hz, 1H), 7.24 (d, J=9.8 Hz, 1H), 7.14 (d, J=9.0 Hz, 1H), 7.04 (m, 1H), 5.22 (s, 2H), 3.45 (s, 2H), 3.35 (s, 1H), 3.10-2.50 (m, 8H), 1.99-1.95 (m, 6H), 1.56 (d, J=13.2 Hz, 3H).

Example 6 dimethyl 2-((5-(4-(3-chloro-4-(3-fluorobenzyloxy)phenylamino)quinazolin-6-yl)furan-2-yl)methylamino)ethylphosphonate Step A: dimethyl 2-(1,3-dioxoisoindolin-2-yl)ethylphosphonate (compound 6.1)

A mixture of 2-(2-bromoethyl)isoindoline-1,3-dione (7.62 g, 30 mmol) and trimethyl phosphite (100 g) was refluxed under $N_2$ atmosphere for 10 hours. Concentration and purification through column chromatography on silica gel (100% EtOAc) gave the desired product as a white solid (5.2 g).

Step B: dimethyl 2-aminoethylphosphonate (compound 6.2)

Compound 6.1 (2.83 g, 10 mmol) was dissolved in 40 mL of ethanol and then 9.5 mmol of hydrazine monohydrate was added. The resulting mixture was refluxed for three hours. Filtered off the white solid formed from the reaction and concentrated the filtrate to give a sticky liquid which can be used for next step without further purification.

Step C: dimethyl 2-((5-(4-(3-chloro-4-(3-fluorobenzyloxy)phenylamino)quinazolin-6-yl)furan-2-yl)methylamino)ethylphosphonate (compound 6)

To a suspension of compound 6.2 (153 mg, 1 mmol) and the compound 1.7 (473 mg, 1 mmol) in DCE (5 mL) was added DIPEA (1.5 mmol) and HOAc (1.5 mmol). After stirring the mixture for 30 minutes, 2.0 mmol of NaBH(OAc)$_3$ was added followed by Stirring the mixture overnight. 1.0 mL of 5M NaOH was added and the mixture was extracted with DCM (2×20 mL). Combined organics was washed with brine and dried over MgSO$_4$. Filtration and concentration followed by purification through flash column chromatography on silica gel (10% methanol in DCM) to get pale brown powder. LCMS ESI(+) m/z: 612 (M+1). $^1$H NMR (CD$_3$OD, 300 MHz) δ 8.64 (s, 1H), 8.45 (s, 1H), 8.13 (d, J=8.4 Hz, 1H), 7.89 (s, 1H), 7.73 (d, J=8.4 Hz, 1H), 7.61 (d, J=7.9 Hz, 1H), 7.38 (m, 1H), 7.28 (d, J=8.8 Hz, 1H), 7.23 (d, J=5.4 Hz, 1H), 7.05 (m, 1H), 6.90 (d, J=2.7 Hz, 1H), 6.44 (d, J=2.7 Hz, 1H), 5.20 (s, 2H), 3.73 (s, 3H), 3.70 (s, 3H), 2.90 (m, 2H), 2.10 (m, 2H).

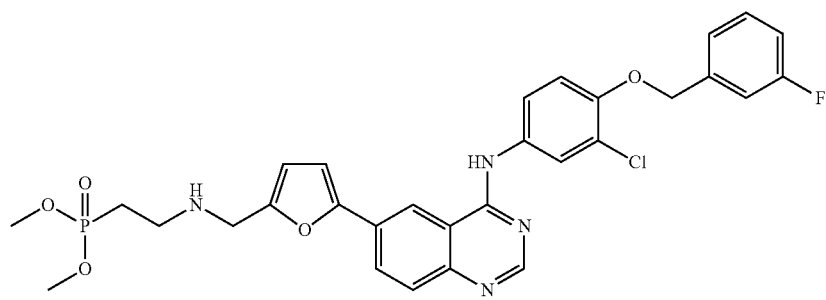 [SMILES: COP(=O)(CCNCc1ccc(-c2ccc3ncnc(Nc4ccc(OCc5cccc(F)c5)c(Cl)c4)c3c2)o1)OC]

Example 7

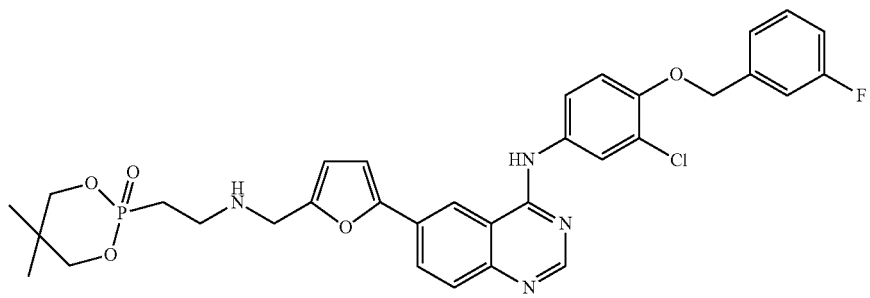 [SMILES: CC1(C)COP(=O)(CCNCc2ccc(-c3ccc4ncnc(Nc5ccc(OCc6cccc(F)c6)c(Cl)c5)c4c3)o2)OC1]

N-(3-chloro-4-(3-fluorobenzyloxy)phenyl)-6-(5-((2-(5,5-dimethyl-1,3,2-dioxaphosphino-2-yl)ethylamino)methyl)furan-2-yl)quinazolin-4-amine

Step A: 2-(1,3-dioxoisoindolin-2-yl)ethylphosphonic dichloride (compound 7.1)

2.83 g of compound 6.2 (10 mmol) was dissolved in 100 mL of DCM and the solution was cooled to 0° C. 2.90 g of TMSBr (20 mmol) was dropwisely added. The mixture was stirred at room temperature for two hours. Concentrated the mixture and afforded a brown residue which was dissolved in 100 mL of DCM. 10 mL of thionyl chloride was added at room temperature and the resulting mixture was stirred at 50° C. for two hours. Concentration of the mixture under reduced pressure afforded sticky oil which was pure enough for next step.

Step B: 2-(2-(5,5-dimethyl-1,3,2-dioxaphosphino-2-yl)ethyl)isoindoline-1,3-dione (compound 7.2)

To the solution of 2.92 g of compound 7.1 (10 mmol) in 100 mL of toluene was added xxx g of xxxalcohol and 1.2 mL of triethylamine at room temperature. The resulting mixture was stirred at 100° C. for two hours. Concentration followed by purification through column chromatography on silica gel gave 3.00 g of desired product as a white solid.

Step C: 2-(5,5-dimethyl-1,3,2-dioxaphosphino-2-yl)ethanamine (compound 7.3)

1.62 g of compound 7.2 (5.0 mmol) was dissolved in 40 mL of ethanol and then 4.5 mmol of hydrazine monohydrate was added. The resulting mixture was refluxed for three hours. Filtered off the white solid formed from the reaction and concentrated the filtrate to give a sticky liquid which can be used for next step without further purification.

Step D: N-(3-chloro-4-(3-fluorobenzyloxy)phenyl)-6-(5-((2-(5,5-dimethyl-1,3,2-dioxaphosphino-2-yl)ethylamino)methyl)furan-2-yl)quinazolin-4-amine (compound 7)

To a suspension of compound 7.3 (193 mg, 1 mmol) and the compound 1.7 (473 mg, 1 mmol) in DCE (5 mL) was added DIPEA (1.5 mmol) and HOAc (1.5 mmol). After stirring the mixture for 30 minutes, 2.0 mmol of NaBH(OAc)$_3$ was added followed by Stirring the mixture overnight. 1.0 mL of 5M NaOH was added and the mixture was extracted with DCM (2×20 mL). Combined organics was washed with brine and dried over MgSO$_4$. Filtration and concentration followed by purification through flash column chromatography on silica gel (10% methanol in DCM) to get pale brown powder. LCMS ESI(+) m/z: 652 (M+1). $^1$H NMR (CD$_3$OD, 300 MHz) δ 8.66 (s, 1H), 8.44 (s, 1H), 8.11 (dd, J1=0.9 Hz, J2=8.4 Hz, 1H), 7.90 (d, J=2.4 Hz, 1H), 7.75 (d, J=8.7 Hz, 1H), 7.62 (dd, J1=2.4 Hz, J2=9.0 Hz, 1H), 7.38 (td, J1=0.7 Hz, J2=7.5 Hz, 1H), 7.28 (d, J=8.8 Hz, 1H), 7.23 (d, J=8.4 Hz, 1H), 7.08 (d, J=7.5 Hz, 1H), 7.03 (td, J1=1.8 Hz, J2=8.1 Hz, 1H), 6.92 (d, J=3.3 Hz, 1H), 6.51 (d, J=3.3 Hz, 1H), 5.20 (s, 2H), 4.00 (d, 4H), 3.05 (m, 1H), 2.30 (m, 2H), 1.04 (s, 3H), 0.99 (s, 3H).

Example 8

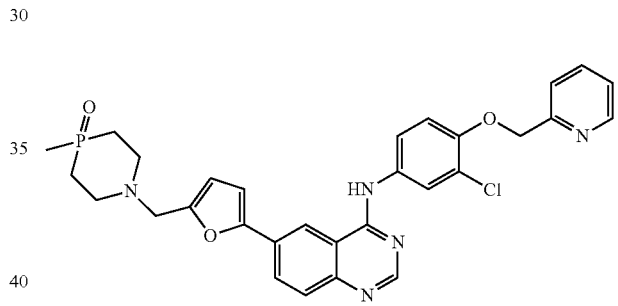

N-(3-chloro-4-(pyridin-2-ylmethoxy)phenyl)-6-(5-((4-methyl-1,4-azaphosphino-1-yl)methyl)furan-2-yl)quinazolin-4-amine

Step A: 3-chloro-4-(2-pyridylmethoxyl)-nitrobenzene (compound 8.1)

To a solution of 2-chloro-1-fluoro-4-nitro-benzene (8.75 g, 50 mmol) in dry Acetone (100 ml) was added 10.0 g of K$_2$CO$_3$ and 5.45 g of 2-pyridylmethanol (50 mmol). The reaction mixture was then stirred at 65° C. overnight. Filtration and concentration gave a solid which was recrystallized to give the desired product as a white solid (10.2 g).

Step B: 3-chloro-4-(2-pyridylmethoxyl)-phenylamine (compound 8.2)

2.65 g of compound 8.1 (10 mmol) was suspended in MeOH (50 ml) and treated wet 5% Pt/C (Degussa type, Aldrich, 1.5 g). The flask is flushed with hydrogen gas from a balloon and the reaction mixture was stirred under hydrogen balloon for 2 hours. The reaction mixture was filtered through a Celite plug and the solvent is removed under reduced pressure to yield 2.0 g of the desired product.

Step C: [3-chloro-4-(2-pyridylmethoxyl)-phenyl]-(6-iodo-quinazolin-4-yl)-amine hydrochloride salt (compound 8.3)

470 mg of compound 8.3 (2 mmol) and 580 mg of 4-chloro-6-iodo-quinazoline (2 mmol) were dissolved in isopropanol (10 ml). The reaction mixture was refluxed for 12 hours. The solid product was collected by filtration, washed with cold isopropanol (10 mL) and ether (20 mL), and air dried to afford 450 mg of the clean desired material.

Step D: 5-(4-(3-chloro-4-(pyridin-2-ylmethoxy)phenylamino)quinazolin-6-yl)furan-2-carbaldehyde (compound 8.4)

A mixture of compound 8.3 (489 mg, 1.0 mmol), 2-furylboronic acid (185 mg, 1.2 mmol) and palladium catalyst (73.0 mg, 0.10 mmol) in 1.0 mL of $K_2CO_3$ (2.0M), 1.0 mL of EtOH and 4.0 mL of DME was heated at 75° C. under nitrogen atmosphere for 4 hr. LS-MS showed the reaction completed. Concentrated the mixture under reduced pressure and washed the residue with water (2×5.0 mL) then with cool ether (10.0 mL) to get a gray solid (400 mg), which was used for next step without further purification.

Step E: N-(3-chloro-4-(pyridin-2-ylmethoxy)phenyl)-6-(5-((4-methyl-1,4-azaphosphino-1-yl)methyl)furan-2-yl)quinazolin-4-amine (compound 8)

To a suspension of compound 1.2 (169 mg, 1 mmol) and the compound 8.4 (228 mg, 0.5 mmol) in DCE (5 mL) was added DIPEA (1.0 mmol) and HOAc (1.0 mmol). After stirring the mixture for 30 minutes, 2.0 mmol of $NaBH(OAc)_3$ was added followed by Stirring the mixture overnight. 1.0 mL of 5M NaOH was added and the mixture was extracted with DCM (2×20 mL). Combined organics was washed with brine and dried over $MgSO_4$. Filtration and concentration followed by purification through flash column chromatography on silica gel (10% methanol in DCM) afforded a brown powder. LCMS ESI(+) m/z: 575 (M+1). $^1$H NMR ($CD_3OD$, 300 MHz) δ 8.65 (d, 1H), 8.55 (d, 1H), 8.47 (s, 1H), 8.16 (dd, 1H), 7.93 (d, 1H), 7.89 (dd, 1H), 7.76 (d, 1H), 7.72 (d, 1H), 7.61 (dd, 1H), 7.39 (td, 1H), 7.16 (d, 1H), 6.96 (d, 1H), 6.49 (d, 1H), 5.27 (s, 2H), 3.35 (s, 2H), 3.35 (s, 2H), 3.05-2.88 (m, 4H), 2.07-2.01 (m, 4H), 1.58 (d, 3H).

Example 9

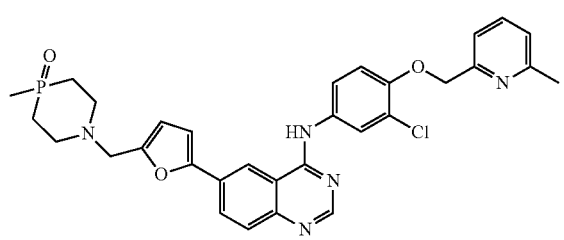

N-(3-chloro-4-((6-methylpyridin-2-yl)methoxy)phenyl)-6-(5-((4-methyl-1,4-azaphosphino-1-yl)methyl)furan-2-yl)quinazolin-4-amine Step A: 3-chloro-4-(6-methyl-2-pyridylmethoxyl)-nitrobenzene (compound 9.1)

To a solution of 2-chloro-1-fluoro-4-nitro-benzene (8.75 g, 50 mmol) in dry acetone (100 ml) was added 10.0 g of $K_2CO_3$ and 6.15 g of 6-methyl-2-pyridylmethanol (50 mmol). The reaction mixture was then stirred at 65° C. overnight. Filtration and concentration gave a solid which was recrystallized to give the desired product as a white solid (9.5 g).

Step B: 3-chloro-4-(6-methyl-2-pyridylmethoxyl)-phenylamine (compound 9.2)

2.79 g of compound 9.1 (10 mmol) was suspended in MeOH (50 ml) and treated wet 5% Pt/C (Degussa type, Aldrich, 1.5 g). The flask is flushed with hydrogen gas from a balloon and the reaction mixture was stirred under hydrogen balloon for 2 hours. The reaction mixture was filtered through a Celite plug and the solvent is removed under reduced pressure to yield 2.2 g of the desired product.

Step C: [3-chloro-4-(2-pyridylmetoxyl)-phenyl]-(6-iodo-quinazolin-4-yl)-amine hydrochloride salt (compound 9.3)

500 mg of compound 9.2 (2 mmol) and 580 mg of 4-chloro-6-iodo-quinazoline (2 mmol) were dissolved in isopropanol (10 ml). The reaction mixture was refluxed for 12 hours. The solid product was collected by filtration, washed with cold isopropanol (10 mL) and ether (20 mL), and air dried to afford 450 mg of the clean desired product.

Step D: 5-(4-(3-chloro-4-((6-methylpyridin-2-yl)methoxy)phenylamino)quinazolin-6-yl)furan-2-carbaldehyde (compound 9.4)

A mixture of compound 9.3 (502 mg, 1.0 mmol), 2-furylboronic acid (185 mg, 1.2 mmol) and palladium catalyst (73.0 mg, 0.10 mmol) in 1.0 mL of $K_2CO_3$ (2.0M), 1.0 mL of EtOH and 4.0 mL of DME was heated at 75° C. under nitrogen atmosphere for 4 hr. LS-MS showed the reaction completed. Concentrated the mixture under reduced pressure and washed the residue with water (2×5.0 mL) then with cool ether (10.0 mL) to get a gray solid (400 mg), which was used for next step without further purification.

Step E: N-(3-chloro-4-((6-methylpyridin-2-yl)methoxy)phenyl)-6-(5-((4-methyl-1,4-azaphosphino-1-yl)methyl)furan-2-yl)quinazolin-4-amine (compound 9)

To a suspension of compound 1.2 (169 mg, 1 mmol) and the compound 9.4 from step D (235 mg, 0.5 mmol) in DCE (5 mL) was added DIPEA (1.0 mmol) and HOAc (1.0 mmol). After stirring the mixture for 30 minutes, 2.0 mmol of $NaBH(OAc)_3$ was added followed by Stirring the mixture overnight. 1.0 mL of 5M NaOH was added and the mixture was extracted with DCM (2×20 mL). Combined organics was washed with brine and dried over $MgSO_4$. Filtration and concentration followed by purification through flash column chromatography on silica gel (10% methanol in DCM) afforded a brown powder. LCMS ESI(+) m/z: 589 (M+1). $^1$H NMR ($CD_3OD$, 300 MHz) δ 8.68 (d, 1H), 8.49 (s, 1H), 8.18 (dd, 1H), 7.93 (d, 1H), 7.80-7.75 (m, 2H), 7.61 (dd, 1H), 7.25

(d, 1H), 7.16 (d, 1H), 6.98 (d, 1H), 6.50 (d, 1H), 5.23 (s, 2H), 3.83 (s, 2H), 3.19-2.90 (m, 4H), 2.58 (S, 3H), 2.08-2.01 (m, 4H), 1.58 (d, 3H).

Example 10

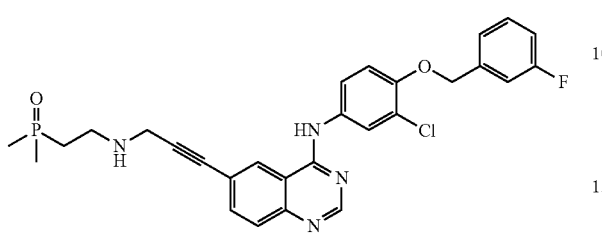

6-(3-(2-(dimethylphosphinoyl)ethylamino)prop-1-ynyl)-N-(4-(3-fluorobenzyloxy)-3-chlorophenyl)quinazolin-4-amine Step A: 3-(4-(4-(3-fluorobenzyloxy)-3-chlorophenylamino)quinazolin-6-yl)prop-2-yn-1-ol (compound 10.1)

To a solution of N-(4-(3-fluorobenzyloxy)-3-chlorophenyl)-6-iodoquinazolin-4-amine (1.52 g), trimethyl(prop-2-ynyloxy)silane (0.7 mL), triethyl amine (0.5 mL) in DMF (10 mL) was added Pd(PPh3)2Cl2 (106 mg), CuI (114 mg) and the mixture was heated at 40° C. overnight. The solvent was removed, then methanol (10 mL) and 4N HCl (2 mL) were added. The reaction mixture was stirred at room temperature for one hour and the solvent was removed. Another 10 mL methanol and triethyl amine (2 mL) were added and the reaction mixture was stirred at room temperature for one hour. The solvent was removed and the residue was purified by flash chromatography, eluting with EtOAc to give the desired product. LCMS ESI(+) m/z: 434 (M+1). Yield: 86%.

Step B: 3-(4-(4-(3-fluorobenzyloxy)-3-chlorophenylamino)quinazolin-6-yl)prop-2-ynyl methanesulfonate (compound 10.2)

To a solution of 3-(4-(4-(3-fluorobenzyloxy)-3-chlorophenylamino)quinazolin-6-yl)prop-2-yn-1-ol (compound 10.1, 800 mg), triethyl amine (0.4 mL) in dichloromethane (20 mL) at 0° C. was added MsCl (0.16 mL) and the reaction mixture was warmed to room temperature. The reaction was washed with saturated NaHCO$_3$ aqueous solution and extracted with dichloromethane. The combined organic layer and extracts were dried over anhydrous magnesium sulfate, filtered and concentrated. The residue was purified by flash chromatography, eluting with EtOAc to give the desired product. LCMS ESI(+) m/z: 513 (M+1). Yield: 43%.

Step C: 6-(3-(2-(dimethylphosphinoyl)ethylamino)prop-1-ynyl)-N-(4-(3-fluorobenzyloxy)-3-chlorophenyl)quinazolin-4-amine (compound 10)

To a solution of 3-(4-(4-(3-fluorobenzyloxy)-3-chlorophenylamino)quinazolin-6-yl)prop-2-ynyl methanesulfonate (compound 10.2, 319 mg), DIPEA (0.37 mL) in dichloromethane (20 mL) at 0° C. was added 2-(dimethylphosphinoyl)ethanamine (83 mg) and the reaction mixture was stirred at room temperature overnight. The solvent was removed and the residue was purified by flash chromatography, eluting with 20% methanol in dichloromethane to give the desired product as yellow solid. LCMS ESI(+) m/z: 538 (M+1). $^1$H NMR (300 MHz, CDCl$_3$) δ 9.47 (s, 1H), 8.87 (s, 1H), 8.70 (s, 1H), 7.95 (m, 2H), 7.85 (m, 2H), 7.62 (m, 2H), 7.38 (m, 1H), 6.98 (m, 1H), 5.10 (s, 2H), 4.25 (m, 2H), 3.87 (m, 1H), 3.58 (m, 1H), 2.05 (m, 2H), 1.57 (m, 6H).

Example 11

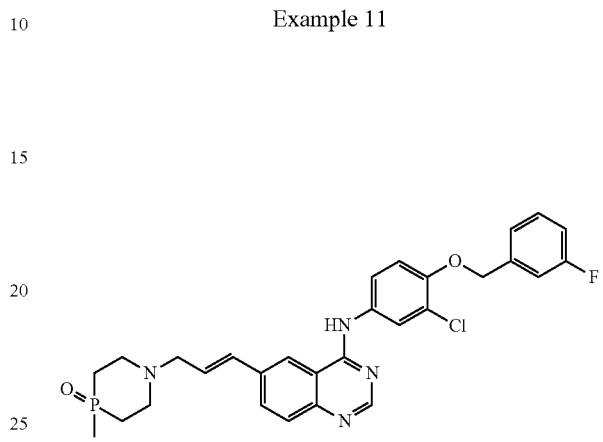

N-(4-(3-fluorobenzyloxy)-3-chlorophenyl)-6-((E)-3-(4-methyl-1,4-azaphosphino-1-yl)prop-1-enyl)quinazolin-4-amine Step A: 1-allyl-4-methyl-1,4-azaphosphinane 4-oxide (compound 11.1)

To a mixture of 4-methyl-1,4-azaphosphinane 4-oxide hydrogen chloride salt (1.69 g), sodium iodide (150 mg) and Cs2CO3 (7.15 g) in acetone (50 mL) was added allyl chloride dropwise. The mixture was stirred at room temperature overnight, filtered and concentrated to provide the desired product as white solid (1.45 g).

Step B: N-(4-(3-fluorobenzyloxy)-3-chlorophenyl)-6-((E)-3-(4-methyl-1,4-azaphosphino-1-yl)prop-1-enyl)quinazolin-4-amine (compound 11)

Under nitrogen atmosphere, Pd(dppf)$_2$Cl$_2$ (85 mg) was added to a mixture of 1-allyl-4-methyl-1,4-azaphosphinane 4-oxide (compound 11.1, 400 mg), -(4-(3-fluorobenzyloxy)-3-chlorophenyl)-6-iodoquinazolin-4-amine (1.4 g) and triethyl amine (1 mL) in DMF (10 mL). The reaction mixture was heated at 85° C. for 4 h and cooled down to room temperature. Ethyl acetate (100 mL) was added and washed with water and brine. The organic layer was dried over anhydrous magnesium sulfate, filtered and concentrated. The residue was purified by flash chromatography, eluting with 20% methanol in dichloromethane to give the desired product as yellow crystalline solid. LCMS ESI(+) m/z: 551 (M+1). $^1$H NMR (300 MHz, CDCl$_3$) δ 8.70 (m, 2H), 8.28 (s, 1H), 7.86 (m, 2H), 7.63 (m, 1H), 7.36 (m, 1H), 7.25 (m, 2H), 6.97 (m, 1H), 5.62 (s, 1H), 5.38 (s, 1H), 5.15 (s, 2H), 3.50 (s, 2H), 3.05 (m, 2H), 2.78 (m, 2H), 2.02 (m, 2H), 1.80 (m, 2H), 1.50 (d, 3H).

Example 12

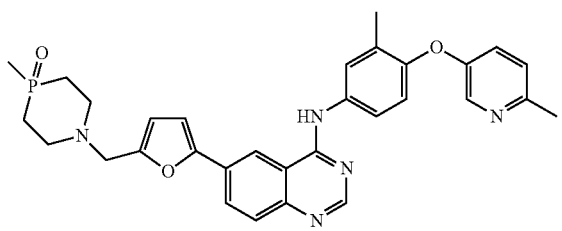

N-(4-(6-methylpyridin-3-yloxy)-3-methylphenyl)-6-(5-((4-methyl-1,4-azaphosphinan-1-yl)methyl)furan-2-yl)quinazolin-4-amine Step A:
5-(2-methyl-4-nitrophenoxy)-2-methylpyridine (compound 12.1)

The mixture of 1-chloro-2-methyl-4-nitrobenzene (17.2 g), 6-methylpyridin-3-ol (12 g) and $Cs_2CO_3$ (39 g) in DMF (150 mL) was heated at 110° C. for 4 h. The solid was filtered and water (100 mL) and EtOAc (200 mL) were added. The organic layer was dried over anhydrous magnesium sulfate, filtered and concentrated. The obtained yellow solid was used for the next step directly.

Step B:
4-(6-methylpyridin-3-yloxy)-3-methylbenzenamine (compound 12.2)

A solution of 5-(2-methyl-4-nitrophenoxy)-2-methylpyridine (compound 12.1) (5 g) in methanol (50 mL) with palladium on carbon (10%, 300 mg) was hydrogenated on a Parr shaker for 24 hours at 60 psi. The mixture was filtered through Celite and all solvents were removed under reduced pressure to give a white crystalline solid, which was used without further purification. LCMS ESI(+) m/z: 215 (M+1).

Step C: N-(4-(6-methylpyridin-3-yloxy)-3-methylphenyl)-6-iodoquinazolin-4-amine (compound 12.3)

4-(6-methylpyridin-3-yloxy)-3-methylbenzenamine (812 mg, 3.79 mmol) and 4-chloro-6-iodo-quinazoline (1 g, 3.4 mmol) were dissolved in isopropanol (50 ml). The reaction mixture was refluxed for 12 hours. The solid product was collected by filtration, washed with cold isopropanol (10 mL) and ether (20 mL), and air dried to afford 1.1 g of the clean desired material.

Step D: 5-(4-(4-(6-methylpyridin-3-yloxy)-3-methylphenylamino)quinazolin-6-yl)furan-2-carbaldehyde (compound 12.4)

Under nitrogen atmosphere, $Pd(dppf)_2Cl_2$ (85 mg) was added to a mixture of N-(4-(6-methylpyridin-3-yloxy)-3-methylphenyl)-6-iodoquinazolin-4-amine (468 mg, 1 mmole), 5-formylfuran-2-yl-2-boronic acid (170 mg) and 2M $K_2CO_3$ (4 mL) in Ethanol (4 mL) and DME (4 mL). The reaction mixture was heated at 75° C. for 4 h and cooled down to room temperature. Methylene chloride (30 mL) was added and washed with water and brine. The organic layer was dried over anhydrous magnesium sulfate, filtered and concentrated. The residue was purified by flash chromatography, eluting with 20% methanol in dichloromethane to give the desired product as white solid (430 mg). LCMS ESI(+) m/z: 437 (M+1). Yield: 98%.

Step E: N-(4-(6-methylpyridin-3-yloxy)-3-methylphenyl)-6-(5-((4-methyl-1,4-azaphosphinan-1-yl)methyl)furan-2-yl)quinazolin-4-amine (compound 12)

5-(4-(4-(6-methylpyridin-3-yloxy)-3-methylphenylamino)quinazolin-6-yl)furan-2-carbaldehyde, 4-methyl-1,4-azaphosphinane 4-oxide hydrogen chloride salt and DIPEA were suspended in dichloromethane (20 mL). Sequentially, acetic acid (3 drops) and sodium triacetoxyborohydride (2 equiv.) were added at room temperature. The mixture was stirred at room temperature until the starting material disappeared. The reaction was quenched with 2N NaOH aqueous solution and extracted with dichloromethane. The combined organic layer and extracts were dried over anhydrous magnesium sulfate, filtered and concentrated. The residue was purified by flash chromatography, eluting with 20% methanol in dichloromethane to give the desired product as yellow crystalline solid. LCMS ESI(+) m/z: 554 (M+1). $^1$H NMR (300 MHz, $CDCl_3$) δ 8.71 (s, 1H), 8.47 (s, 1H), 8.18 (d, 1H), 8.12 (s, 1H), 7.77 (d, 1H), 7.69 (m, 1H), 7.60 (d, 1H), 7.28 (m, 2H), 6.99 (m, 2H), 6.51 (d, 1H), 3.83 (s, 2H), 3.73 (m, 2H), 3.24 (m, 2H), 2.95 (m, 2H), 2.51 (s, 3H), 2.27 (s, 3H), 2.04 (m, 2H), 1.58 (m, 3H).

Example 13

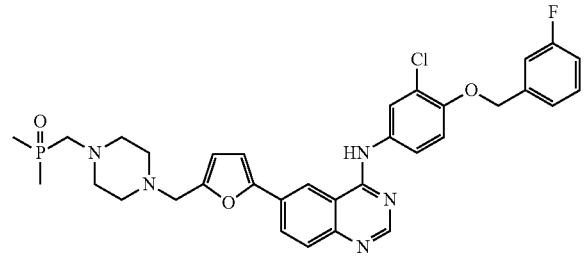 [SMILES: CP(C)(=O)CN1CCN(Cc2ccc(-c3ccc4ncnc(Nc5ccc(OCc6cccc(F)c6)c(Cl)c5)c4c3)o2)CC1]

N-(4-(3-fluorobenzyloxy)-3-chlorophenyl)-6-(5-((4-((dimethylphosphinoyl)-methyl)piperazin-1-yl)methyl)furan-2-yl)quinazolin-4-amine Step A: benzyl 4-((dimethylphosphinoyl)methyl)piperazine-1-carboxylate (compound 13.1)

To a solution of chloromethanephosphonyl dichloride (2 g, 12 mmole) in THF (30 mL) at −78° C. was added methyl magnesium chloride (8 mL, 3M in THF) slowly and the reaction mixture warmed up to room temperature overnight. To the reaction mixture was added benzyl piperazine-1-carboxylate (2.8 mL) and potassium carbonate (5 g) and the solution was refluxed overnight. The solid was removed by filtration and the solvent was removed to furnish the residue, which was purified by flash chromatography eluting with 10% methanol in dichloromethane to give the desired product. LCMS ESI(+) m/z: 311 (M+1).

Step B: 1-((dimethylphosphinoyl)methyl)piperazine (compound 13.2)

To a flask was charged with benzyl 4-((dimethylphosphinoyl)methyl)piperazine-1-carboxylate (200 mg) and 10% palladium on carbon in methanol (20 mL). The mixture was stirred at room temperature under H2 atmosphere. The mixture was filtered through Celite and all solvents were removed under reduced pressure to give a white crystalline solid, which was used without further purification. LCMS ESI(+) m/z: 177 (M+1).

Step C: N-(4-(3-fluorobenzyloxy)-3-chlorophenyl)-6-(5-((4-((dimethylphosphinoyl)-methyl)piperazin-1-yl)methyl)furan-2-yl)quinazolin-4-amine (compound 13)

5-(4-(4-(3-fluorobenzyloxy)-3-chlorophenylamino) quinazolin-6-yl)furan-2-carbaldehyde and 1-((dimethylphosphinoyl)methyl)piperazine were suspended in dichloromethane (20 mL). Sequentially, acetic acid (3 drops) and sodium triacetoxyborohydride (2 equiv.) were added at room temperature. The mixture was stirred at room temperature until the starting material disappeared. The reaction was quenched with 2N NaOH aqueous solution and extracted with dichloromethane. The combined organic layer and extracts were dried over anhydrous magnesium sulfate, filtered and concentrated. The residue was purified by flash chromatography, eluting with 20% methanol in dichloromethane to give the desired product as yellow crystalline solid. LCMS ESI(+) m/z: 635 (M+1). $^1$H NMR (300 MHz, CD$_3$OD) δ 8.59 (s, 1H), 8.44 (s, 1H), 8.11 (m, 1H), 7.89 (m, 1H), 7.72 (m, 1H), 7.57 (m, 1H), 7.38 (m, 1H), 7.26 (m, 2H), 7.08 (m, 2H), 6.90 (d, 1H), 6.46 (d, 1H), 5.17 (s, 2H), 3.66 (s, 2H), 2.80 (m, 2H), 2.68 (m, 8H), 1.57 (d, 6H).

Example 14

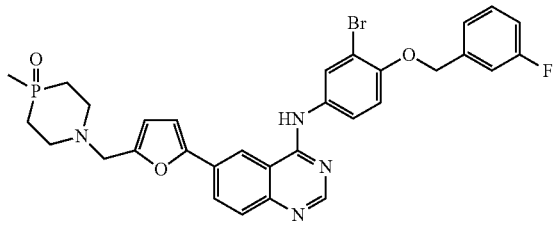 [SMILES: CP1(=O)CCN(Cc2ccc(-c3ccc4ncnc(Nc5ccc(OCc6cccc(F)c6)c(Br)c5)c4c3)o2)CC1]

N-(4-(3-fluorobenzyloxy)-3-bromophenyl)-6-(5-((4-methyl-1,4-azaphosphino-1-yl)methyl)furan-2-yl) quinazolin-4-amine Step A: (1-((2-bromo-4-nitrophenoxy)methyl)-3-fluorobenzene (compound 14.1)

The mixture of 2-bromo-1-fluoro-4-nitrobenzene (5 g), (3-fluorophenyl)methanol (2.86 g) and K$_2$CO$_3$ (9.4 g) in Acetone (50 mL) was refluxed for 4 h. The solid was filtered and the solvent was removed. The obtained yellow solid was recrystallized from EtOAc/Hexane to provide brown solid (6.8 g). Yield: 92%.

Step B: 4-(3-fluorobenzyloxy)-3-bromobenzenamine (compound 14.2)

A solution of (1-((2-bromo-4-nitrophenoxy)methyl)-3-fluorobenzene (3.26 g) in methanol (50 mL) with palladium on carbon (10%, 300 mg) was hydrogenated on a Parr shaker for 24 hours at 60 psi. The mixture was filtered through Celite and all solvents were removed under reduced pressure to give a white crystalline solid, which was used without further purification. LCMS ESI(+) m/z: 297 (M+1).

Step C: N-(4-(3-fluorobenzyloxy)-3-bromophenyl)-6-iodoquinazolin-4-amine (compound 14.3)

4-(3-fluorobenzyloxy)-3-bromobenzenamine (1.48 g, 5 mmol) and 4-chloro-6-iodo-quinazoline (1.45 g, 5 mmol) were dissolved in isopropanol (50 ml). The reaction mixture was refluxed for 12 hours. The solid product was collected by filtration, washed with cold isopropanol (10 mL) and ether (20 mL), and air dried to afford 2.7 g of the clean desired material.

Step D: 5-(4-(4-(3-fluorobenzyloxy)-3-bromophenylamino)quinazolin-6-yl)furan-2-carbaldehyde (compound 14.4)

Under nitrogen atmosphere, Pd(dppf)$_2$Cl$_2$ (80 mg) was added to a mixture of N-(4-(3-fluorobenzyloxy)-3-bromophenyl)-6-iodoquinazolin-4-amine (550 mg, 1 mmole), 5-formylfuran-2-yl-2-boronic acid (170 mg, 1.2 mmole) and 2M K$_2$CO$_3$ (4 mL) in Ethanol (4 mL) and DME (4 mL). The reaction mixture was heated at 75° C. for 4 h and cooled down to room temperature. Methylene chloride (30 mL) was added and washed with water and brine. The organic layer was dried over anhydrous magnesium sulfate, filtered and concentrated. The residue was purified by flash chromatography, eluting with 20% methanol in dichloromethane to give the desired product as white solid (460 mg). LCMS ESI(+) m/z: 519 (M+1). Yield: 89%.

Step E: N-(4-(3-fluorobenzyloxy)-3-bromophenyl)-6-(5-((4-methyl-1,4-azaphosphino-1-yl)methyl)furan-2-yl)quinazolin-4-amine (compound 14)

5-(4-(4-(3-fluorobenzyloxy)-3-bromophenylamino) quinazolin-6-yl)furan-2-carbaldehyde (444 mg, 0.86 mmole), 4-methyl-1,4-azaphosphinane 4-oxide hydrogen chloride salt (137 mg, 1 mmole) and DIPEA were suspended in dichloromethane (20 mL). Sequentially, acetic acid (3 drops) and sodium triacetoxyborohydride (2 equiv.) were added at room temperature. The mixture was stirred at room temperature until the starting material disappeared. The reaction was quenched with 2N NaOH aqueous solution and extracted with dichloromethane. The combined organic layer and extracts were dried over anhydrous magnesium sulfate, filtered and concentrated. The residue was purified by flash chromatography, eluting with 20% methanol in dichloromethane to give the desired product as yellow crystalline solid (388 mg). LCMS ESI(+) m/z: 637 (M+1). Yield: 71%. $^1$H NMR (300 MHz, CD$_3$OD) δ 8.64 (s, 1H), 8.46 (s, 1H), 8.15 (m, 1H), 8.04 (m, 1H), 7.75 (m, 1H), 7.65 (m, 1H), 7.38

(m, 1H), 7.26 (m, 2H), 7.08 (m, 2H), 6.95 (m, 1H), 6.48 (d, 1H), 5.21 (s, 2H), 3.80 (s, 2H), 2.88 (m, 4H), 2.03 (m, 4H), 1.57 (d, 3H).

Example 15

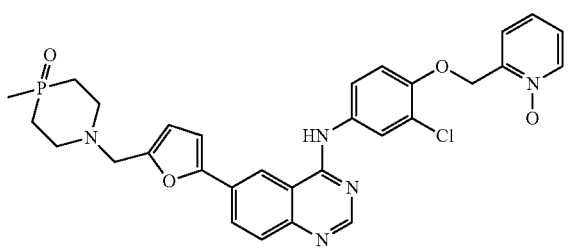

2-((2-chloro-4-(6-(5-((4-methyl-1,4-azaphosphino-1-yl)methyl)furan-2-yl)quinazolin-4-ylamino)phenoxy)methyl)pyridine 1-oxide Step A: 3-chloro-4-(2-pyridylmethoxyl)-N-Boc-phenylamine (compound 15.1)

To a solution of 2.35 g of compound 8.3 (10 mmol) in 50 mL of DCM was added 3.0 g of (Boc)₂O and 2.5 g of DMAP. The resulting mixture was stirred at room temperature for five hours. Concentration and purification of the residue through flash column chromatography on silica gel gave the desired product.

Step B: 3-chloro-4-(N-oxidepyridine-2-methoxyl)-phenylamine TFA salt (compound 15.2)

To a solution of 1.34 g of compound 15.1 (4.0 mmol) in 50 mL of DCM was added 1.5 g of m-CPBA (6.0 mmol) and the resulting mixture was stirred at room temperature for two hours. 10 mL of 2.0N NaOH was added and the organics was extracted with 100 mL of DCM and then dried over MgSO₄. Filtration and concentration gave a brown residue which was dissolved again in 100 mL of DCM. 5.0 mL of TFA was added and the mixture was stirred at room temperature until LC-MS showed the deprotection completed. Concentration under reduced pressure gave the desired product as a TFA salt which was used directly for next step without further purification.

Step C: [3-chloro-4-(N-oxidepyridine-2-methoxyl)-phenyl]-(6-iodo-quinazolin-4-yl)-amine hydrochloride salt (compound 15.3)

1.0 g of compound 15.2 (2 mmol) and 1.2 g of 4-chloro-6-iodo-quinazoline (2 mmol) were dissolved in isopropanol (50 ml). The reaction mixture was refluxed for 12 hours. The solid product was collected by filtration, washed with cold isopropanol (10 mL) and ether (20 mL), and air dried to afford 1.5 g of the clean desired product.

Step D: 2-((2-chloro-4-(6-(5-formylfuran-2-yl)quinazolin-4-ylamino)phenoxy)methyl)pyridine 1-oxide (compound 15.4)

A mixture of compound 15.3 (505 mg, 1.0 mmol), 2-furylboronic acid (168 mg, 1.2 mmol) and palladium catalyst (73.0 mg, 0.10 mmol) in 1.0 mL of K₂CO₃ (2.0M), 1.0 mL of EtOH and 4.0 mL of DME was heated at 75° C. under nitrogen atmosphere for 4 hr. LS-MS showed the reaction completed. Concentrated the mixture under reduced pressure and washed the residue with water (2×5.0 mL) then with cool ether (10.0 mL) to get a gray solid (400 mg), which was used for next step without further purification.

Step E: 2-((2-chloro-4-(6-(5-((4-methyl-1,4-azaphosphino-1-yl)methyl)furan-2-yl)quinazolin-4-ylamino)phenoxy)methyl)pyridine 1-oxide (compound 15)

To a suspension of compound 1.2 (169 mg, 1 mmol) and the compound 15.4 from step D (237 mg, 0.5 mmol) in DCE (5 mL) was added DIPEA (1.0 mmol) and HOAc (1.0 mmol). After stirring the mixture for 30 minutes, 2.0 mmol of NaBH(OAc)₃ was added followed by Stirring the mixture overnight. 1.0 mL of 5M NaOH was added and the mixture was extracted with DCM (2×20 mL). Combined organics was washed with brine and dried over MgSO₄. Filtration and concentration followed by purification through flash column chromatography on silica gel (10% methanol in DCM) afforded a brown powder. LCMS ESI(+) m/z: 591 (M+1). ¹H NMR (CD₃OD, 300 MHz) δ 8.64 (d, 1H), 8.48 (s, 1H), 8.39 (d, 1H), 8.16 (d, 1H), 8.13 (d, 1H), 7.99 (d, 1H), 7.80 (d, 1H), 7.76 (d, 1H), 7.70-7.65 (m, 2H), 7.52 (m, 1H), 7.20 (d, 1H), 6.95 (d, 1H), 6.48 (d, 1H), 5.39 (s, 2H), 3.81 (s, 2H), 3.08-2.90 (m, 4H), 2.07-2.01 (m, 4H), 1.58 (d, 3H).

Example 16

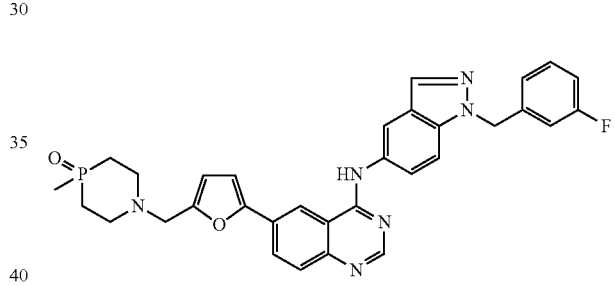

N-(1-(3-fluorobenzyl)-1H-indazol-5-yl)-6-(5-((4-methyl-1,4-azaphosphino-1-yl)methyl)furan-2-yl)quinazolin-4-amine Step A: 1-(3-fluorobenzyl)-5-nitro-1H-indazole (compound 16.1)

A suspension of 5-nitrobenzoindazole (8.16 g, 50 mmol), 3-fluorobenzyl bromide (10.4 g, 55 mmol) and potassium carbonate (13.8 g, 100 mmol) in acetone (200 mL) was refluxed overnight. After reaction cooled to room temperature, the reaction mixture was diluted with dichloromethane (100 mL), filtered through silica gel (about 100 g), and rinsed with 1:1 ethyl acetate:dichloromethane (about 100 mL). The residue after concentration was purified with column chromatography eluting with 0-30% ethyl acetate in dichloromethane to give the title compound as a white crystalline solid (the first fraction, 5.69 g, 42%). LCMS ESI(+) m/z: 272 (M+1).

Step B: 1-(3-fluorobenzyl)-1H-indazol-5-amine (compound 16.2)

A suspension of compound 16.1 (2.71 g, 10 mmol) and palladium 10% on carbon (1.0 g, wet) in methanol (40 mL)

was hydrogenated under a hydrogen balloon for 14 hours. The reaction mixture was then filtered through Celite (20 g), rinsed with dichloromethane/methanol (3/1), and concentrated to give the title compound as a white crystalline solid (2.40 g, 100%). The product is used without further purification. LCMS ESI(+) m/z: 242 (M+1).

Step C: N-(1-(3-fluorobenzyl)-1H-indazol-5-yl)-6-iodoquinazolin-4-amine (compound 16.3)

Compound 16.3 was prepared according to the procedure for compound 1.6 using compound 16.3 instead of compound 1.5, to give a pale yellow solid, LCMS ESI(+) m/z: 496 (M+1).

Step D; 5-(4-(1-(3-fluorobenzyl)-1H-indazol-5-ylamino)quinazolin-6-yl)furan-2-carbaldehyde (compound 16.4)

Compound 16.4 was prepared according to the procedure in Example 1, step G for the preparation of compound 1.7 to give a yellow crystalline solid, LCMS ESI(+) m/z: 464 (M+1).

Step E: N-(1-(3-fluorobenzyl)-1H-indazol-5-yl)-6-(5-((4-methyl-1,4-azaphosphino-1-yl)methyl)furan-2-yl)quinazolin-4-amine (compound 16)

The title compound was prepared according to the procedure for compound 1 using compound 16.4 instead of compound 1.7, to give a pale yellow solid, LCMS ESI(+) m/z: 581 (M+1). $^1$H NMR (DMSO-$d_6$, 300 MHz) δ 11.95 (br s, 1H), 8.88 (s, 1H), 8.43 (d, 1H), 8.23 (s, 1H), 8.17 (s, 1H), 7.96 (d, 1H), 7.84 (d, 1H), 7.81 (d, 1H), 7.37 (m, 2H), 7.18-7.02 (m, 3H), 6.92 (d, 1H), 5.73 (s, 2H), 4.61 (s, 2H), 3.39 (m, 4H), 2.27 (m, 4H), 1.58 (d, 3H).

Example 17

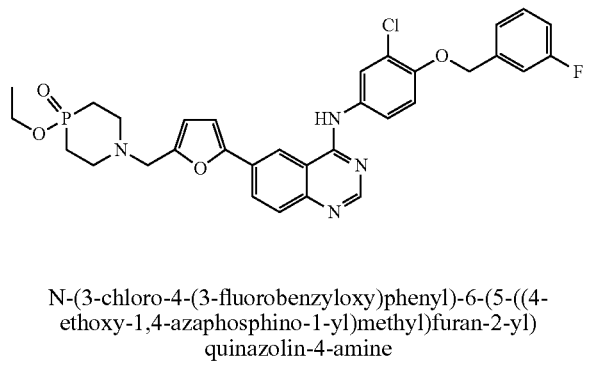

N-(3-chloro-4-(3-fluorobenzyloxy)phenyl)-6-(5-((4-ethoxy-1,4-azaphosphino-1-yl)methyl)furan-2-yl)quinazolin-4-amine Step A: 4-ethoxy-1,4-azaphosphinane, 4-oxide The title compound was prepared according to the procedure in Steps A and B of Example 1, using ethyl dichlorophosphite instead of methylphosphonic dichloride, to give the compound 17.1 as a clear viscous liquid. LCMS ESI(+) m/z: 164 (M+1)

Step B: N-(3-chloro-4-(3-fluorobenzyloxy)phenyl)-6-(5-((4-ethoxy-1,4-azaphosphino-1-yl)methyl)furan-2-yl)quinazolin-4-amine The title compound was prepared according to the procedure for compound 1 using compound 4-ethoxy-1,4-azaphos-phinane, 4-oxide instead of compound 1.2, to give a pale yellow solid, LCMS ESI(+) m/z: 621 (M+1). $^1$H NMR (CD$_3$OD, 300 MHz) δ 8.65 (d, 1H), 8.47 (s, 1H), 8.16 (dd, 1H), 7.90 (d, 1H), 7.77 (d, 1H), 7.61 (dd, 1H), 7.41 (q, 1H), 7.34-7.21 (m, 2H), 7.16 (d, 1H), 7.05 (dt, 1H), 6.96 (d, 1H), 6.49 9d, 1H), 5.22 (s, 2H), 4.08 (pentalet, 2H), 3.81 (s, 2H), 2.81 (m, 4H), 2.01 (m, 4H), 1.33 (t, 3H).

Example 18

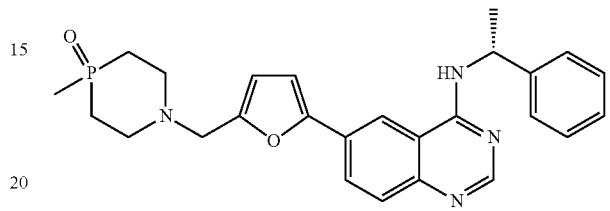

(R)-6-(5-((4-methyl-1,4-azaphosphino-1-yl)methyl)furan-2-yl)-N-(1-phenylethyl)quinazolin-4-amine The title compound was prepared according to the procedures of steps G and H for example 1 using (R)-1-phenyle-thanamine instead of compound 1.5, to give a pale yellow solid, LCMS ESI(+) m/z: 461 (M+1). $^1$H NMR (CDCl$_3$, 300 MHz) δ 8.62 (s, 1H), 8.03 (s, 1H), 7.95 (d, 1H), 7.83 (d, 1H), 7.51 (d, 2H), 7.40 (t, 2H), 7.33 (d, 1H), 6.71 (d, 1H), 6.36 (d, 1H), 5.72 (m, 1H), 3.79 (s, 2H), 3.13 (m, 2H), 2.88 (m, 2H), 2.18-1.80 (m, 4H), 1.77 (d, 3H), 1.54 (d, 3H).

Example 19

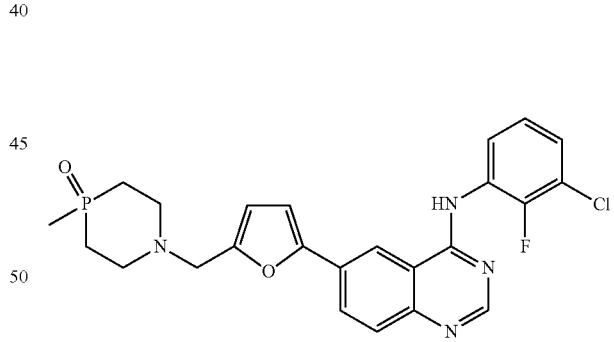

N-(3-chloro-2-fluorophenyl)-6-(5-((4-methyl-1,4-azaphosphino-1-yl)methyl)furan-2-yl)quinazolin-4-amine The title compound was prepared according to the procedures of steps G and H for example 1 using 3-chloro-2-fluoroaniline instead of compound 1.5, to give a pale yellow solid, LCMS ESI(+) m/z: 485 (M+1). $^1$H NMR (CDCl$_3$, 300 MHz) δ 8.78 (s, 1H), 8.44 (m, 1H), 8.23 (s, 1H), 8.05 (d, 1H), 7.94 (d, 1H), 7.20 (d, 1H), 6.78 (d, 1H), 6.39 (d, 1H), 3.83 (s, 2H), 3.18 (m, 2H), 2.90 (m, 2H), 2.20-1.82 (m, 4H), 1.55 (d, 3H).

Example 20

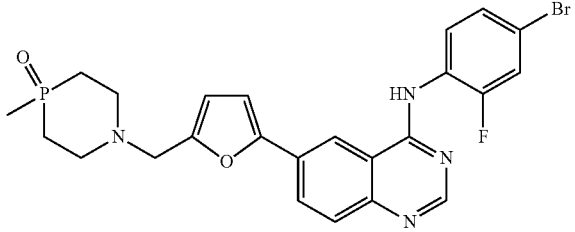 [SMILES: CP1(=O)CCN(Cc2ccc(-c3ccc4ncnc(Nc5ccc(Br)cc5F)c4c3)o2)CC1]

N-(4-Bromo-2-fluorophenyl)-6-(5-((4-methyl-1,4-azaphosphino-1-yl)methyl)furan-2-yl)quinazolin-4-amine The title compound was prepared according to the procedures of steps G and H for example 1 using 4-bromo-2-fluoroaniline instead of compound 1.5, to give a pale yellow solid, LCMS ESI(+) m/z: 529, 531 (M+1). $^1$H NMR (CDCl$_3$, 300 MHz) δ 8.76 (s, 1H), 8.41 (t, 1H), 8.22 (s, 1H), 8.05 (d, 1H), 7.93 (d, 1H), 7.39 (d, 2H), 6.78 (d, 1H), 6.39 (d, 1H), 3.82 (s, 2H), 3.15 (m, 2H), 2.90 (m, 2H), 2.40-1.90 (m, 4H), 1.55 (d, 3H).

Example 21

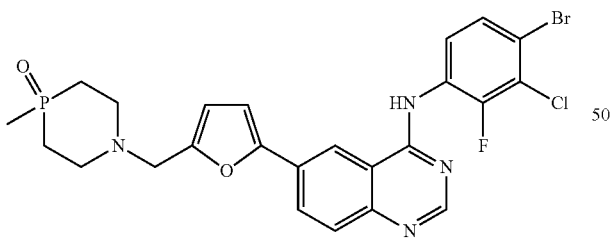

N-(4-Bromo-3-chloro-2-fluorophenyl)-6-(5-((4-methyl-1,4-azaphosphino-1-yl)methyl)furan-2-yl)quinazolin-4-amine The title compound was prepared according to the procedures of steps G and H for example 1 using 4-bromo-3-chloro-2-fluoroaniline instead of compound 1.5, to give a pale yellow solid, LCMS ESI(+) m/z: 563, 565 (M+1). $^1$H NMR (CDCl$_3$, 300 MHz) δ 8.76 (s, 1H), 8.36 (t, 1H), 8.26 (s, 1H), 8.05 (d, 1H), 7.93 (d, 1H), 7.51 (dd, 1H), 6.78 (d, 1H), 6.39 (d, 1H), 3.84 (s, 2H), 3.15 (m, 2H), 2.90 (m, 2H), 2.40-1.90 (m, 4H), 1.55 (d, 3H).

Example 22

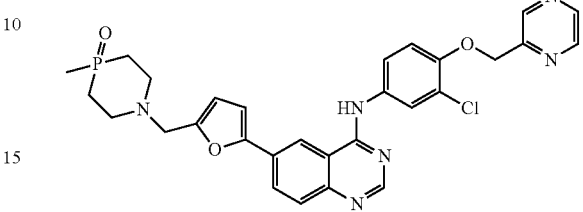

N-(3-chloro-4-(pyrazin-2-ylmethoxy)phenyl)-6-(5-((4-methyl-1,4-azaphosphino-1-yl)methyl)furan-2-yl)quinazolin-4-amine Step A:
3-chloro-4-(2-pyrazinemethoxyl)-nitrobenzene (compound 22.1)

To a solution of 2-chloro-1-fluoro-4-nitro-benzene (875 mg, 5.0 mmol) in dry Acetone (10.0 ml) was added 1.0 g of K$_2$CO$_3$ and 545 mg of 2-pyrazinylmethanol (5.0 mmol). The reaction mixture was then stirred at 65° C. overnight. Filtration and concentration gave a solid which was recrystallized to give the desired product as a red solid.

Step B:
3-chloro-4-(2-pyrazinemethoxyl)-phenylamine (compound 8.3)

265 mg of compound 22.2 (1.0 mmol) was suspended in MeOH (50 ml) and treated wet 5% Pt/C (Degussa type, Aldrich, 1.5 g). The flask is flushed with hydrogen gas from a balloon and the reaction mixture was stirred under hydrogen balloon for 2 hours. The reaction mixture was filtered through a Celite plug and the solvent is removed under reduced pressure to yield 200 mg of the desired product.

Step C: [3-chloro-4-(2-pyrazinemetoxyl)-phenyl]-(6-iodo-quinazolin-4-yl)-amine hydrochloride salt (compound 22.3)

235 mg of compound 15.3 (1.0 mmol) and 290 mg of 4-chloro-6-iodo-quinazoline (1.0 mmol) were dissolved in isopropanol (10 ml). The reaction mixture was refluxed for 12 hours. The solid product was collected by filtration, washed with cold isopropanol (10 mL) and ether (20 mL), and air dried to afford 200 mg of the clean desired material.

Step D: 5-(4-(3-chloro-4-(pyrazin-2-ylmethoxy)phenylamino)quinazolin-6-yl)furan-2-carbaldehyde (compound 22.4)

A mixture of compound 15.4 (489 mg, 1.0 mmol), 2-furylboronic acid (185 mg, 1.2 mmol) and palladium catalyst (73.0 mg, 0.10 mmol) in 1.0 mL of K$_2$CO$_3$ (2.0M), 1.0 mL of EtOH and 4.0 mL of DME was heated at 75° C. under nitrogen atmosphere for 4 hr. LS-MS showed the reaction completed. Concentrated the mixture under reduced pressure and washed the residue with water (2×5.0 mL) then with cool ether (10.0 mL) to get a gray solid which was used for next step without further purification.

Step E: N-(3-chloro-4-(pyrazin-2-ylmethoxy)phenyl)-6-(5-((4-methyl-1,4-azaphosphino-1-yl)methyl)furan-2-yl)quinazolin-4-amine (compound 22)

To a suspension of compound 1.2 (169 mg, 1 mmol) and the compound 15.5 from step D (228 mg, 0.5 mmol) in DCE (5 mL) was added DIPEA (1.0 mmol) and HOAc (1.0 mmol). After stirring the mixture for 30 minutes, 2.0 mmol of NaBH(OAc)$_3$ was added followed by Stirring the mixture overnight. 1.0 mL of 5M NaOH was added and the mixture was extracted with DCM (2×20 mL). Combined organics was washed with brine and dried over MgSO$_4$. Filtration and concentration followed by purification through flash column chromatography on silica gel (15% methanol in DCM) afforded a red powder. LCMS ESI(+) m/z: 576 (M+1).

Example 23

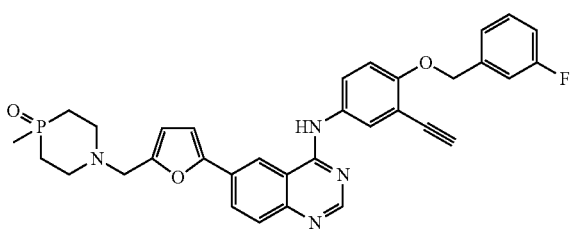 [SMILES: C#Cc1cc(Nc2ncnc3ccc(-c4ccc(CN5CCP(C)(=O)CC5)o4)cc23)ccc1OCc1cccc(F)c1]

N-(4-(3-fluorobenzyloxy)-3-ethynylphenyl)-6-(5-((4-methyl-1,4-azaphosphino-1-yl)methyl)furan-2-yl)quinazolin-4-amine Step A: (2-(2-(3-fluorobenzyloxy)-5-nitrophenyl)ethynyl)triisopropylsilane (compound 23.1)

To a solution of 1-((2-bromo-4-nitrophenoxy)methyl)-3-fluorobenzene (1 g), ethynyltriisopropylsilane (1.032 mL), pyrrolidine (0.3 mL) in DMF (20 mL) was added Pd(PPh$_3$)$_2$Cl$_2$ (501 mg), CuI (117 mg) and the mixture was heated at 80° C. overnight. The solvent was removed, the residue was purified by flash chromatography, eluting with 10% EtOAc in hexane to give the desired product (2-(2-(3-fluorobenzyloxy)-5-nitrophenyl)ethynyl)triisopropylsilane (compound 23.1, 472 mg) and 4-(3-fluorobenzyloxy)-3-(2-(triisopropylsilyl)ethynyl)benzenamine (compound 23.2, 440 mg). LCMS ESI(+) m/z: 428 (M+1) and LCMS ESI(+) m/z: 398 (M+1).

Step B: 4-(3-fluorobenzyloxy)-3-(2-(triisopropylsilyl)ethynyl)benzenamine (compound 23.2)

To a flask was charged with (2-(2-(3-fluorobenzyloxy)-5-nitrophenyl)ethynyl)triisopropylsilane (compound 23.1, 472 mg, 1.11 mmole), Fe (309 mg), HOAc (4 mL) and EtOH (10 mL). The reaction mixture was refluxed for 3 h and the solvent was removed. Methylene was added and washed with aqueous NaHCO$_3$. The organic layer was dried over anhydrous magnesium sulfate, filtered and concentrated. The residue was purified by flash chromatography, eluting with 30% EtOAc in Hexane to give the desired product as yellow crystalline. LCMS ESI(+) m/z: 398 (M+1).

Step C: N-(4-(3-fluorobenzyloxy)-3-(2-(triisopropylsilyl)ethynyl)phenyl)-6-iodoquinazolin-4-amine (compound 23.3)

4-(3-fluorobenzyloxy)-3-(2-(triisopropylsilyl)ethynyl)benzenamine (900 mg, 2.27 mmol) and 4-chloro-6-iodoquinazoline (657 mg, 2.27 mmol) were dissolved in isopropanol (50 ml). The reaction mixture was refluxed for 12 hours. The solid product was collected by filtration, washed with cold isopropanol (10 mL) and ether (20 mL), and air dried to afford the clean desired material.

Step D: 5-(4-(4-(3-fluorobenzyloxy)-3-(2-(triisopropylsilyl)ethynyl)phenylamino)quinazolin-6-yl)furan-2-carbaldehyde (compound 23.4)

Under nitrogen atmosphere, Pd(dppf)$_2$Cl$_2$ (48 mg) was added to a mixture of N-(4-(3-fluorobenzyloxy)-3-(2-(triisopropylsilyl)ethynyl)phenyl)-6-iodoquinazolin-4-amine (420 mg, 0.65 mmole), 5-formylfuran-2-yl-2-boronic acid (108 mg, 1.2 equiv.) and 2M K$_2$CO$_3$ (4 mL) in Ethanol (4 mL) and DME (4 mL). The reaction mixture was heated at 75° C. for 4 h and cooled down to room temperature. Methylene chloride (30 mL) was added and washed with water and brine. The organic layer was dried over anhydrous magnesium sulfate, filtered and concentrated. The residue was purified by flash chromatography, eluting with 20% methanol in dichloromethane to give the desired product as white solid (300 mg). LCMS ESI(+) m/z: 620 (M+1). Yield: 75%.

Step E: N-(4-(3-fluorobenzyloxy)-3-(2-(triisopropylsilyl)ethynyl)phenyl)-6-(5-((4-methyl-1,4-azaphosphino-1-yl)methyl)furan-2-yl)quinazolin-4-amine (compound 23.5)

5-(4-(4-(3-fluorobenzyloxy)-3-(2-(triisopropylsilyl)ethynyl)phenylamino)quinazolin-6-yl)furan-2-carbaldehyde (573 mg, 0.926 mmole) and 4-methyl-1,4-azaphosphinane 4-oxide (185 mg, 1.5 equiv.) were suspended in dichloromethane (20 mL). Sequentially, acetic acid (3 drops) and sodium triacetoxyborohydride (2 equiv.) were added at room temperature. The mixture was stirred at room temperature until the starting material disappeared. The reaction was quenched with 2N NaOH aqueous solution and extracted with dichloromethane. The combined organic layer and extracts were dried over anhydrous magnesium sulfate, filtered and concentrated. The residue was purified by flash chromatography, eluting with 20% methanol in dichloromethane to give the desired product as yellow crystalline solid (452 mg). LCMS ESI(+) m/z: 737 (M+1). Yield: 66%.

Step F: N-(4-(3-fluorobenzyloxy)-3-ethynylphenyl)-6-(5-((4-methyl-1,4-azaphosphino-1-yl)methyl)furan-2-yl)quinazolin-4-amine (compound 23)

The mixture of Compound 23.4 (50 mg) and CsF (52 mg) in DMF was stirred at 50° C. for 2 h. The filtration removed the solid and the residue was purified by flash chromatography, eluting with 20% methanol in dichloromethane to give the desired product as yellow crystalline solid (42 mg). LCMS ESI(+) m/z: 581 (M+1). Yield: 86%. $^1$H NMR (300 MHz, CD$_3$OD) δ 8.62 (d, 1H), 8.43 (s, 1H), 8.13 (m, 1H), 7.81 (m, 1H), 7.75 (m, 1H), 7.66 (m, 1H), 7.38 (m, 1H), 7.29 (m, 2H), 7.05 (m, 2H), 6.94 (m, 1H), 6.48 (d, 1H), 5.21 (s, 2H), 3.80 (s, 2H), 3.74 (s, 1H), 2.88 (m, 4H), 2.03 (m, 4H), 1.57 (d, 3H).

Example 24

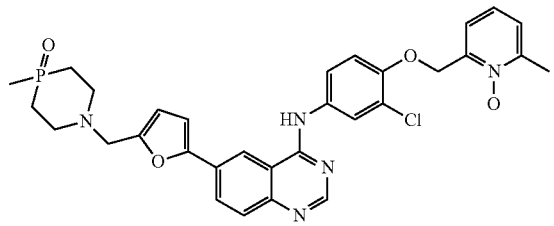

2-((2-chloro-4-(6-(5-((4-methyl-1,4-azaphosphino-1-yl)methyl)furan-2-yl)quinazolin-4-ylamino)phenoxy)methyl)-6-methylpyridine 1-oxide The title compound was prepared according to the procedures for example 1 using compound 9.2 at step A instead of compound 8.2, to give a pale yellow solid, LCMS ESI(+) m/z: 604 (M+1). $^1$H NMR (CD$_3$OD, 300 MHz) δ 8.68 (s, 1H), 8.49 (s, 1H), 8.17 (dd, 1H), 8.00 (d, 1H), 7.78 (d, 1H), 7.73 (m, 1H), 7.68 (dd, 1H), 7.62-7.50 (m, 2H), 7.22 (d, 1H), 6.97 (d, 1H), 6.50 (d, 1H), 5.42 (s, 2H), 3.82 (s, 2H), 3.10-2.80 (m, 4H), 2.59 (s, 3H), 2.05 (m, 4H), 1.58 (d, 3H).

Example 25

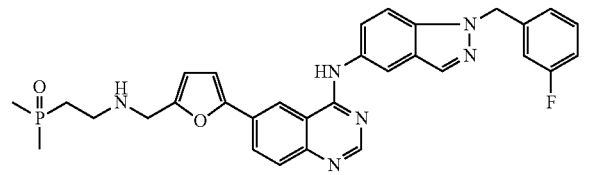 [SMILES: CP(C)(=O)CCNCc1ccc(-c2ccc3ncnc(Nc4ccc5c(cnn5Cc5cccc(F)c5)c4)c3c2)o1]

6-(5-((2-(dimethylphosphinoyl)ethylamino)methyl)furan-2-yl)-N-(1-(3-fluorobenzyl)-1H-indazol-5-yl)quinazolin-4-amine 5-(4-(1-(3-fluorobenzyl)-1H-indazol-5-ylamino)quinazolin-6-yl)furan-2-carbaldehyde and 2-(dimethylphosphinoyl)ethanamine (compound 2.2, 82 mg) were suspended in dichloromethane (20 mL). Sequentially, acetic acid (3 drops) and sodium triacetoxyborohydride (237 mg) were added at room temperature. The mixture was stirred at room temperature until the starting material disappeared. The reaction was quenched with 2N NaOH aqueous solution and extracted with dichloromethane. The combined organic layer and extracts were dried over anhydrous magnesium sulfate, filtered and concentrated. The residue was purified by flash chromatography, eluting with 20% methanol in dichloromethane to give the desired product as yellow crystalline solid (138 mg). LCMS ESI(+) m/z: 569 (M+1). Yield: 43%. $^1$H NMR (300 MHz, CD$_3$OD) δ 8.75 (d, 1H), 8.40 (s, 1H), 8.18 (m, 1H), 8.12 (m, 2H), 7.76 (m, 1H), 7.68 (m, 1H), 7.61 (m, 1H), 7.30 (m, 2H), 7.03 (m, 2H), 6.92 (m, 3H), 6.46 (d, 1H), 5.69 (s, 2H), 3.91 (s, 2H), 2.99 (m, 2H), 2.10 (m, 2H), 1.52 (d, 3H).

Example 26

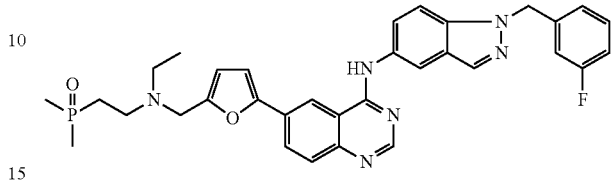

2-(N-((5-(4-(1-(3-fluorobenzyl)-1H-indazol-5-ylamino)quinazolin-6-yl)furan-2-yl)methyl)-N-(2-(dimethylphosphino)ethyl)amino)ethane To a solution of 6-(5-((2-(dimethylphosphinoyl)ethylamino)methyl)furan-2-yl)-N-(1-(3-fluorobenzyl)-1,1-indazol-5-yl)quinazolin-4-amine, acetaldehyde (20 mg) and two drops of acetic acid in ethanol (10 mL) was added NaBH$_4$CN (8 mg). The reaction mixture was stirred at room temperature for 1 h. The reaction was quenched with 2N NaOH aqueous solution and extracted with dichloromethane. The combined organic layer and extracts were dried over anhydrous magnesium sulfate, filtered and concentrated. The residue was purified through the Preparative HPLC to provide the desired product. LCMS ESI(+) m/z: 597 (M+1). $^1$H NMR (300 MHz, CD$_3$OD) δ 9.20 (d, 1H), 8.66 (s, 1H), 8.45 (m, 1H), 8.18 (s, 1H), 8.07 (s, 1H), 7.85 (m, 1H), 7.66 (m, 2H), 7.36 (m, 1H), 7.21 (d, 2H), 6.09-7.13 (m, 4H), 5.72 (d, 2H), 4.65 (d, 2H), 3.95 (m, 4H), 2.60 (m, 2H), 1.52 (d, 3H), 1.45 (t, 3H).

Example 27

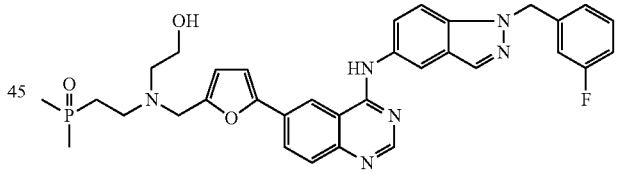

2-(N-((5-(4-(1-(3-fluorobenzyl)-1H-indazol-5-ylamino)quinazolin-6-yl)furan-2-yl)methyl)-N-(2-(dimethylphosphinoyl)ethyl)amino)ethanol Step A: 2-(N-((5-(4-(1-(3-fluorobenzyl)-1H-indazol-5-ylamino)quinazolin-6-yl)furan-2-yl)methyl)-N-(2-(dimethylphosphinoyl)ethyl)amino)ethanol TBS protected (compound 27.1)

To a solution of 6-(5-((2-(dimethylphosphinoyl)ethylamino)methyl)furan-2-yl)-N-(1-(3-fluorobenzyl)-1H-indazol-5-yl)quinazolin-4-amine, (tert-Butyldimethylsilyloxy)acetaldehyde (0.017 mL) and two drops of acetic acid in ethanol (10 mL) was added NaBH$_4$CN (8 mg). The reaction mixture was stirred at room temperature for 1 h. The reaction was quenched with 2N NaOH aqueous solution and extracted with dichloromethane. The combined organic layer and extracts were dried over anhydrous magnesium sulfate, filtered and concentrated for the next step.

Step B: 2-(N-((5-(4-(1-(3-fluorobenzyl)-1H-indazol-5-ylamino)quinazolin-6-yl)furan-2-yl)methyl)-N-(2-(dimethylphosphinoyl)ethyl)amino)ethanol (compound 27)

The mixture of Compound 27.1 (20 mg) and CsF (20 mg) in DMF was stirred at 50° C. for 2 h. The filtration removed the solid and the residue was purified through the Preparative HPLC to provide the desired product. LCMS ESI(+) m/z: 613 (M+1). $^1$H NMR (300 MHz, CD$_3$OD) δ 9.20 (d, 1H), 8.67 (s, 1H), 8.45 (m, 1H), 8.19 (s, 1H), 8.08 (s, 1H), 7.89 (m, 1H), 7.66 (m, 2H), 7.36 (m, 1H), 7.21 (d, 2H), 6.09-7.13 (m, 4H), 5.72 (d, 2H), 4.75 (d, 2H), 3.95 (m, 4H), 3.78 (m, 2H), 2.60 (m, 2H), 1.52 (d, 3H).

Example 28

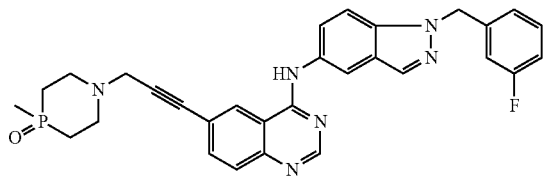 [SMILES: CP1(=O)CCN(CC#Cc2ccc3ncnc(Nc4ccc5c(cnn5Cc5cccc(F)c5)c4)c3c2)CC1]

N-(1-(3-fluorobenzyl)-1H-indazol-5-yl)-6-(3-(4-methyl-1,4-azaphosphino-1-yl)prop-1-ynyl)quinazolin-4-amine The title compound was prepared according to the procedure of step B for example 4 using compound 16.3 instead of compound 1.6, to give a pale yellow solid, LCMS ESI(+) m/z: 539 (M+1). $^1$H NMR (CDCl$_3$, 300 MHz) δ 8.69 (s, 1H), 8.48 (s, 1H), 8.04 (d, 1H), 7.83 (d, 1H), 7.73 (d, 1H), 7.69 (d, 1H), 7.34 (d, 1H), 7.27 (t, 1H), 6.97 (m, 2H), 6.88 (d, 1H) 5.60 (s, 2H), 3.74 (s, 2H), 3.20 (m, 2H), 3.00 (m, 2H), 2.00 (m, 4H), 1.61 (d, 3H).

Example 29

Biological Example

Kinase Assay for EGFR

The extent to which the compounds of the present invention modulate EGFR kinase activity can be determined using time-resolved Fret (TR-FRET) assay (LanthaScreen® kinase activity assay, from Invitrogen). The assay employs EGFR kinase (PV3872, Invitrogen), Tb-Py20 antibody (PV3552, Invitrogen) and fluorescein-poly GT (PV3610, In vitrogen)

The assay is performed in a Black 384-well plate (available from Corning). EGFR kinase (is diluted in TR-FRET Dilution Buffer (PV3189, InVitrogen) at concentration of 0.4 ug/ml as stock solution, and then 2-fold serial diluted. Addition of 1 mM ATP initiated the reaction, and the reaction is incubated for 1 h reaction at room temperature. 10 μL of the Tb-antibody (from Invitrogen)+EDTA (from Invitrogen) solution prepared was added to each well of the assay plate and mix briefly, and incubated for 30 min. The signal is monitored by using M5 microplate reader (Ex=332 nm, Em=488 nm and 518 nm). Each compound is tested in duplicate wells. EGFR without compound is used as control. Staurosporine (available from Sigma) is used as positive control compound. Inhibition was calculated as percentage of the EGFR activity (without compound)

Example 30

Biological Example

Kinase Assay for ErbB2

The assay is performed similarly to the kinase assay for ErbB2 as described above, except ErbB2 kinase protein is used instead of EGFR kinase protein.

Example 31

Cell Proliferation Inhibition Assay for BT474

Human breast cancer BT474 cells was cultured in low glucose DMEM (Life Technologies 12320-032) containing 10% fetal bovine serum (FBS) at 37° C. in a humidified 10% CO$_2$, 90% air incubator. Cells were harvested using trypsin/EDTA, counted using a haemocytometer, and plated 10000 cell/well in a 96-well clear tissue culture plate. The cells were incubated for 24 h at 37° C. to allow adherence. A serials of concentrations of each compound (ranging from 30 uM to 0.16 nM, 5-fold dilution) in 96-well plate, and incubated for 72 h. Each concentration was tested in triplicate wells. During the cell proliferation assay, BT474 cells were cultured in low-glucose DMEM containing 5% FBS, 50 ug/ml gentamicin, and 0.3% v/v DMSO. The culture medium was removed via aspiration, and the cell viability was detected by using CCK-8 cell proliferation kit.

The biological activities of EGFR kinase inhibition, ErbB2 (HER2) kinase inhibition and BT474 proliferation inhibition are listed in Table 1

TABLE 1

| Example # | EGFR inhibition[a] inhibit % at 100 nM or IC50 (nM) | ErbB2 inhibition[a] % inhibition at 100 nM or IC50 (nM) | BT474 proliferation[b] Inhibition IC50 (nM) (8 points) |
|---|---|---|---|
| 1 | ++ | ++ | ++ |
| 2 | ++ | ++ | ++ |
| 3 | ++ | ++ | + |
| 4 | ++ | ++ | ++ |
| 5 | ++ | ++ | |
| 6 | ++ | ++ | |
| 7 | ++ | ++ | |
| 8 | ++ | ++ | ++ |
| 9 | + | + | + |
| 10 | ++ | − | |
| 11 | ++ | ++ | |
| 12 | ++ | ++ | |
| 13 | ++ | ++ | + |
| 14 | ++ | ++ | |
| 15 | ++ | ++ | ++ |
| 16 | ++ | ++ | |
| 17 | ++ | ++ | ++ |
| 18 | ++ | + | |
| 19 | ++ | + | |
| 20 | + | ++ | |
| 21 | ++ | − | |
| 22 | ++ | ++ | |
| 23 | ++ | ++ | + |
| 24 | ++ | ++ | + |
| 25 | ++ | ++ | + |

TABLE 1-continued

| Example # | EGFR inhibition[a] inhibit % at 100 nM or IC50 (nM) | ErbB2 inhibition[a] % inhibition at 100 nM or IC50 (nM) | BT474 proliferation[b] Inhibition IC50 (nM) (8 points) |
|---|---|---|---|
| 26 | ++ | ++ | + |
| 27 | ++ | ++ | ++ |
| 28 | ++ | ++ | + |

Symbol: "++" indicates >50% inhibition at 100 nM, or IC50 <100 nM for EGFR or ErbB2 kinases; "+" indicates between 20% to 50% inhibition at 100 nM, or IC50 between 100 and 1000 nM; "−" indicates <20% inhibition at 100 nM.

Example 32

Pharmacokinetic Studies of Example 4 in Mouse, Rat and Dog

The dog PK protocol is shown here, while PK study protocol of mouse and rat are similar to dog. Beagle dogs of this study were 6-8 month old and weighed 8 to 10 kg. Example 4 was dissolved in 2% DMA and 98% (40% HP-β-CD in deionized water) to yield concentration at 2 mg/mL for both intravenous (IV, a bolus injection via the lateral tail vein) and oral (PO, via oral gavage) administrations. Blood samples (approximately 1 ml) was collected via cephalic into tubes containing EDTA-K3 anticoagulant pre-dose and post-dose at 5 min, 15 min, 30 min, 1 h, 2 h, 4 h, 6 h, 8 h and 24 h. Blood samples were centrifuged at approximately 8000 rpm for 6 minutes at 2-8° C. and the resulting plasma were separated, labeled and stored frozen at approximately −80° C. Plasma samples analysis was performed by means of LC-MS/MS. The analytical results were confirmed using quality control samples for intra-assay variation.

Pharmacokinetic data for Example 4 are shown in Table 2. The oral bioavailability (F) for lapatinib is 32% (mouse), 29% (rat), or 63% (dog).

TABLE 2

| species | Route, dose (mg/Kg) | Cmax ng/mL | T½ hr | CL L/hr | Vz L | AUC0-t ng*hr/mL | AUC0-inf-obs ng*hr/mL | F % |
|---|---|---|---|---|---|---|---|---|
| Mouse | IV, 2 | 1515 | 0.59 | 0.39 | 0.33 | 5073 | 5083 | |
| | PO, 10 | 2838 | 1.41 | | | 8830 | 9063 | 36 |
| rat | IV, 2 | 1567 | 19.9 | 0.92 | 7.92 | 2133 | 2183 | |
| | PO, 10 | 1797 | 11.5 | | | 9702 | 9780 | 89.6 |
| dog | IV, 2 | 1147 | 2.46 | 1.34 | 1.44 | 1482 | 1488 | |
| | PO, 10 | 2380 | 3.80 | | | 7637 | 7716 | 100 |

Example 33

Anticancer Effect of Example 4 Against NCI-N87 Xenograft in Balb/c Nude Mice

NCI-N87 cells were purchased from ATCC, and were cultured in RPMI1640+10% FBS+1% P/S antibiotics. Balb/c nude mice were male, 6-8 week old, and weighed 18±2 g. The cells were implanted subcutaneously into the nude mice (right flank) with 5.0×10[6] cells in 0.1 ml PBS. When the tumor size reached a volume of 200 (150-200) mm³, the tumor-bearing nude mice derived from NCI-N87 cells were randomly assigned into four groups (10 mice/group). All groups were dosed oral, BID. One group were dosed with vehicle, one group with Lapatinib (75 mg/kg of free base, in the form of ditosylate monoydrate), and the rest two groups with Example 4 (50, 100 mg/kg, p.o. Bid, respectively). The administration period lasted 4 weeks. The tumor volume were measured twice a week, and the body weight were measured immediately before measuring the tumor volume throughout the whole study. On day 11 after initiation of the treatment, the dosing of Example 4 at 100 mg/kg was suspended, and the dosing of the group was resumed on day 15 at a reduced dose of 75 mg/Kg. The tumor growth inhibition rates were 85% and 88% for 50 mg/Kg and 100/75 mg/Kg dosage group of Example 4 compound, while it was 48% tumor growth inhibition rate for lapatinib at 75 mg/Kg. (See FIG. 1).

Figure 2:
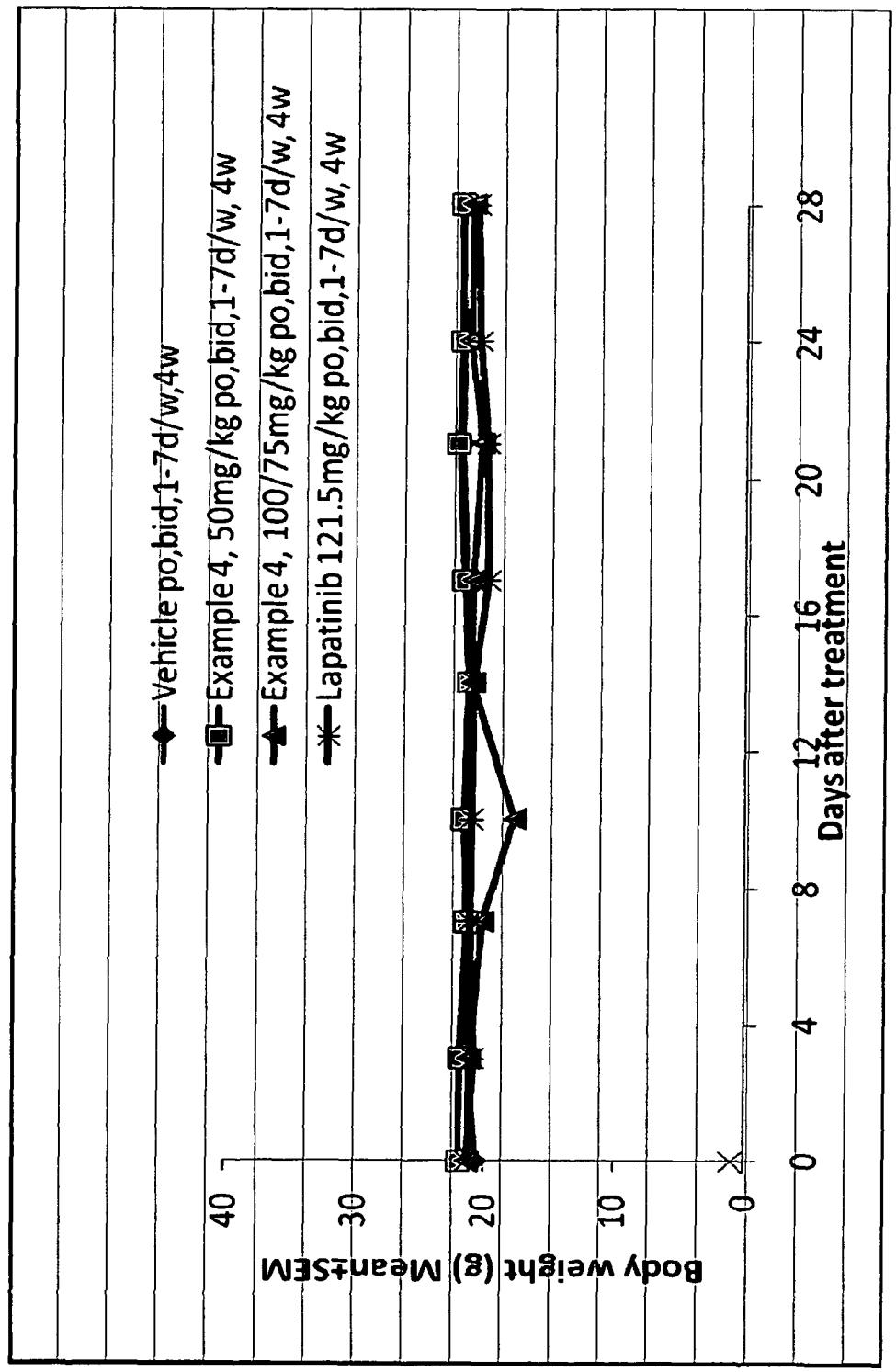
FIG. 2 shows the body weight change of the NCI-N87 xenograft Balb/c nude mice during administration of Example 4.

Nude mouse bodyweight change was shown in FIG. 2. Significant body weight loss (average 16.9%) was observed for Example 4 at 100 mg/Kg, po, bid dosing group on day 10. However after dosing suspension for 3 days and resumption of dosing at 75 mg/kg, po, bid on day 14, the body weight of nude mice recovered and remained normal for the group.

All references throughout, such as publications, patents, patent applications and published patent applications, are incorporated herein by reference in their entireties.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:

1. A compound of formula A:

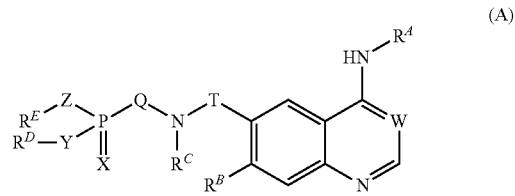

(A)

wherein:

W is N;

$R^A$ is a substituted monocyclic, bicyclic or tricyclic aryl or heteroaryl moiety, or an arylalkyl group;

$R^B$ is hydrogen, halogen, cyano, nitro, trifluoromethyl, difluoromethyl, trifluoromethoxy, difluoromethoxy, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkylalkyl, heterocyclyl, heterocyclylalkyl, —$NR^1SO_2R^2$, —$SO_2NR^1R^3$, —$C(O)R^4$, —$C(O)OR^5$, —$OC(O)R^4$, —$NR^1C(O)OR^5$, —$NR^1C(O)R^4$, —$C(O)NR^1R^3$, —$NR^1R^3$, —$NR^1C(O)NR^1R^3$, —$OR^5$, —$S(O)R^2$, —$SO_2R^2$ or —$SR^2$, wherein each said alkyl, alkenyl, alkynyl, cycloalkyl, cycloalkylalkyl, heterocyclyl and heterocyclylalkyl is unsubstituted or optionally substituted with up to five groups independently selected from the group consisting of oxo, halogen, $C_1$-$C_6$ alkyl, $C_2$-$C_6$ alkenyl, $C_2$-$C_6$ alkynyl, $C_3$-$C_8$ cycloalkyl, $C_3$-$C_8$ cycloalkylalkyl, cyano, trifluoromethyl, difluoromethoxy, trifluoromethoxy, azido, —NR$^{11}$SO$_2$R$^{12}$, —SO$_2$NR$^{11}$R$^{13}$, —C(O)R$^{14}$, —C(O)OR$^{15}$, —OC(O)R$^{14}$, —NR$^{11}$C(O)OR$^{16}$, —NR$^{11}$C(O)R$^{14}$, —C(O)NR$^{11}$R$^{13}$, —NR$^{11}$R$^{13}$, —NR$^{11}$C(O)NR$^{11}$R$^{13}$, —OR$^{15}$, —S(O)R$^{12}$, —SO$_2$R, —SR$^{12}$, heterocyclyl and heterocyclylalkyl;

T is a divalent radical formed by removing an additional hydrogen atom from a C$_1$-C$_6$ alkyl, C$_2$-C$_6$ alkenyl, C$_2$-C$_6$ alkynyl, C$_3$-C$_8$ cycloalkyl, C$_3$-C$_8$ cycloalkylalkyl, aryl, arylalkyl, heteroaryl, heteroarylalkyl, heterocyclyl or heterocyclylalkyl; wherein each said alkyl, alkenyl, alkynyl, cycloalkyl, aryl, heteroaryl and heterocyclyl is unsubstituted or optionally substituted with up to three groups independently selected from the group consisting of oxo, halogen, C$_1$-C$_3$ alkyl, C$_2$-C$_3$ alkenyl, C$_2$-C$_3$ alkynyl, cyano, trifluoromethyl, difluoromethoxy, trifluoromethoxy, azido, —NR$^{11}$SO$_2$R$^{12}$, —SO$_2$NR$^{11}$R$^{13}$, —C(O)R$^{14}$, —C(O)OR$^{15}$, —OC(O)R$^{14}$, NR$^{11}$C(O)OR$^{15}$, —NR$^{11}$C(O)R$^{14}$, —C(O)NR$^{11}$R$^{13}$, —NR$^{11}$R$^{13}$, —NR$^{11}$C(O)NR$^{11}$R$^{13}$, —OR$^{15}$, —S(O)R$^{12}$, —SO$_2$R$^{12}$ and —SR$^{12}$;

Q is a bond or C$_1$-C$_6$ alkylene, wherein said alkylene is unsubstituted or optionally substituted with up to three groups independently selected from the group consisting of oxo, halogen, C$_1$-C$_3$ alkyl, cyano, trifluoromethyl, difluoromethoxy, trifluoromethoxy, —NR$^{11}$R$^{13}$ and —OR$^{15}$;

X is O or S;

Y and Z are independently O, S, NR$^1$ or a bond;

R$^C$ is H, C$_1$-C$_6$ alkyl, C$_3$-C$_6$ cycloalkyl, —SO$_2$NR$^3$R$^1$, —C(O)R$^4$, —C(O)OR$^5$, —C(O)NR$^1$R$^3$, or —SO$_2$R$^2$, wherein each said alkyl and cycloalkyl is unsubstituted or optionally substituted with up to five groups independently selected from the group consisting of oxo, halogen, cyano, azido and —OR$^{15}$;

R$^D$ is C$_1$-C$_8$ alkyl, C$_3$-C$_8$ cycloalkyl, aryl, arylalkyl, heteroaryl, heteroarylalkyl, heterocyclyl or heterocyclylalkyl, wherein each said alkyl, cycloalkyl, aryl, arylalkyl, heteroaryl, heteroarylalkyl, heterocyclyl and heterocyclylalkyl is unsubstituted or optionally substituted with up to five groups independently selected from the group consisting of the group consisting of oxo, halogen, cyano, —OR$^{15}$, —NR$^{11}$R$^{13}$, —SO$_2$R$^{12}$, —SR$^{12}$, trifluoromethyl, difluoromethoxy and trifluoromethoxy; and R$^E$ is C$_1$-C$_8$ alkyl, C$_3$-C$_8$ cycloalkyl, aryl, arylalkyl, heteroaryl, heteroarylalkyl, heterocyclyl or heterocyclylalkyl, wherein each said alkyl, cycloalkyl, aryl, arylalkyl, heteroaryl, heteroarylalkyl, heterocyclyl and heterocyclylalkyl is unsubstituted or optionally substituted with up to five groups independently selected from the group consisting of the group consisting of oxo, halogen, cyano, —OR$^{15}$, —NR$^{11}$R$^{13}$, —SO$_2$R$^{12}$, —SR$^{12}$, trifluoromethyl, difluoromethoxy and trifluoromethoxy;

or wherein R$^C$ and R$^D$ are together with Y, Q and the atoms to which they are attached to form a 4 to 10 membered heterocyclic ring which is optionally substituted with up to five groups independently selected from the group consisting of halogen, oxo, —OR$^{15}$, —NR$^{11}$R$^{13}$, —SO$_2$R$^{12}$, —SR$^{12}$, C$_1$-C$_6$ alkyl; C$_3$-C$_6$ cycloalkyl, trifluoromethyl, difluoromethoxy, trifluoromethoxy, azido, aryl, heteroaryl, arylalkyl, heteroarylalkyl, heterocyclyl and heterocyclylalkyl;

or wherein R$^D$ and R$^E$ are taken together with Y, Z and the phosphorus atom to which they are attached to form a 4 to 10 membered heterocyclic ring which is optionally substituted with up to five groups independently selected from the group consisting of halogen, oxo, —OR$^{15}$, —NR$^{11}$R$^{13}$, —SO$_2$R$^{12}$, —SR$^{12}$, C$_1$-C$_6$alkyl, C$_1$-C$_6$cyclylalkyl, trifluoromethyl, difluoromethoxy, trifluoromethoxy, azido, aryl, heteroaryl, arylalkyl, heteroarylalkyl, heterocyclyl and heterocyclylalkyl;

wherein:

each R$^1$ is independently hydrogen, C$_1$-C$_6$ alkyl or C$_3$-C$_6$ cycloalkyl, wherein each said alkyl and cycloalkyl is unsubstituted or optionally substituted with up to five groups independently selected from the group consisting of oxo, halogen, cyano, azido and —OR$^{15}$;

each R$^2$ is independently C$_1$-C$_6$ alkyl, C$_3$-C$_6$ cycloalkyl, aryl, arylalkyl, heteroaryl, heteroarylalkyl, heterocyclyl or heterocyclylalkyl, wherein each said alkyl, cycloalkyl, aryl, arylalkyl, heteroaryl, heteroarylalkyl, heterocyclyl and heterocyclylalkyl is unsubstituted or optionally substituted with up to five groups independently selected from the group consisting of oxo, halogen, cyano and —OR$^{15}$;

each R$^3$ is independently hydrogen, C$_1$-C$_6$ alkyl, C$_2$-C$_6$ alkenyl, C$_2$-C$_6$ alkynyl, C$_3$-C$_8$ cycloalkyl, C$_3$-C$_8$ cycloalkylalkyl, heterocyclyl or heterocyclylalkyl, wherein each said alkyl, cycloalkyl, cycloalkylalkyl, heterocyclyl and heterocyclylalkyl is unsubstituted or optionally substituted with up to five groups independently selected from the group consisting of oxo, halogen, cyano, azido and —OR$^{15}$;

each R$^4$ is independently hydrogen, C$_1$-C$_6$ alkyl or C$_3$-C$_6$ cycloalkyl, wherein each said alkyl and cycloalkyl is unsubstituted or optionally substituted with up to five groups independently selected from the group consisting of oxo, halogen, cyano, azido and —OR$^{15}$; and each R$^5$ is hydrogen, C$_1$-C$_8$ alkyl, C$_2$-C$_8$ alkenyl, C$_2$-C$_8$ alkynyl, C$_3$-C$_8$ cycloalkyl, C$_3$-C$_8$ cycloalkylalkyl, heterocyclyl or heterocyclylalkyl, wherein each said alkyl, cycloalkyl, cycloalkylalkyl, heterocyclyl and heterocyclylalkyl is unsubstituted or optionally substituted with up to five groups independently selected from the group consisting of oxo, halogen, cyano and azido;

or wherein when R$^1$ and R$^2$ are attached to the same atom or are attached to adjacent atoms, R$^1$ and R$^2$ are together with the atom or the atoms to which they are attached to form a 4 to 10 membered heterocyclic ring which is optionally substituted with up to three groups independently selected from the group consisting of halogen, oxo, cyano, trifluoromethyl, difluoromethoxy, trifluoromethoxy, azido, heterocyclyl and heterocyclylalkyl;

or wherein when R$^1$ and R$^3$ are attached to the same atom or are attached to adjacent atoms, R$^1$ and R$^3$ are taken together with the atom or the atoms to which they are attached to form a 4 to 10 membered heterocyclic ring which is optionally substituted with up to three groups independently selected from the group consisting of halogen, oxo, cyano, trifluoromethyl, difluoromethoxy, trifluoromethoxy, azido, heterocyclyl and heterocyclylalkyl;

or wherein when R$^1$ and R$^4$ are attached to the same atom or are attached to adjacent atoms, R$^1$ and R$^4$ are taken together with the atom or the atoms to which they are attached to form a 4 to 10 membered heterocyclic ring which is optionally substituted with up to three groups independently selected from the group consisting of halogen, oxo, cyano, trifluoromethyl, difluoromethoxy, trifluoromethoxy, azido, heterocyclyl and heterocyclylalkyl;

or wherein when R$^1$ and R$^5$ are attached to the same atom or are attached to adjacent atoms, R$^1$ and R$^5$ are taken together with the atom or the atoms to which they are attached to form a 4 to 10 membered heterocyclic ring which is optionally substituted with up to three groups independently selected from the group consisting of halogen, oxo, cyano, trifluoromethyl, difluoromethoxy, trifluoromethoxy, azido, heterocyclyl and heterocyclylalkyl;

wherein:

each $R^{11}$ is independently hydrogen, $C_1$-$C_6$ alkyl or $C_3$-$C_6$ cycloalkyl;

each $R^{12}$ is independently $C_1$-$C_6$ alkyl, $C_3$-$C_6$ cycloalkyl, aryl, arylalkyl, heteroaryl, heteroarylalkyl, heterocyclyl or heterocyclylalkyl;

each $R^{13}$ is independently hydrogen, $C_1$-$C_6$ alkyl, $C_2$-$C_6$ alkenyl, $C_2$-$C_6$ alkynyl, $C_3$-$C_8$ cycloalkyl, $C_3$-$C_8$ cycloalkylalkyl, heterocyclyl or heterocyclylalkyl;

each $R^{14}$ is independently hydrogen, $C_1$-$C_6$ alkyl or $C_3$-$C_6$ cycloalkyl;

each $R^{15}$ is hydrogen, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkylalkyl, heterocyclyl or heterocyclylalkyl; and each $R^{16}$ is independently $C_1$-$C_6$ alkyl, $C_3$-$C_6$ cycloalkyl, $C_3$-$C_8$ cycloalkylalkyl, heterocyclyl or heterocyclylalkyl;

wherein each heteroaryl is independently a monocyclic aromatic radical of 5 to 10 ring atoms or a polycyclic aromatic radical, containing one or more ring heteroatoms selected from nitrogen, oxygen and sulfur; and each heterocyclyl is independently a saturated or partially unsaturated cyclic radical of 3 to 8 ring atoms in which at least one ring atom is a heteroatom selected from nitrogen, oxygen and sulfur;

or a salt thereof.

2. The compound of claim 1, wherein the compound is of the formula (Aa):

(Aa)

wherein:

W is N;

$R^A$ is a substituted monocyclic, bicyclic or tricyclic aryl or heteroaryl moiety, or an arylalkyl group;

$R^B$ is hydrogen, halogen, cyano, nitro, trifluoromethyl, difluoromethyl, trifluoromethoxy, difluoromethoxy, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkylalkyl, heterocyclyl, heterocyclylalkyl, —$NR^1SO_2R^2$, —$SO_2NR^1R^3$, —$C(O)R^4$, —$C(O)OR^5$, —$OC(O)R^4$, —$NR^1C(O)OR^5$, —$NR^1C(O)R^4$, —$C(O)NR^1R^3$, —$NR^1R^3$, —$NR^1C(O)NR^1R^3$, —$OR^5$, —$S(O)R^2$, —$SO_2R^2$ or —$SR^2$, wherein each said alkyl, alkenyl, alkynyl, cycloalkyl, cycloalkylalkyl, heterocyclyl and heterocyclylalkyl is unsubstituted or optionally substituted with up to five groups independently selected from the group consisting of oxo, halogen, $C_1$-$C_6$ alkyl, $C_2$-$C_6$ alkenyl, $C_2$-$C_6$ alkynyl, $C_3$-$C_8$ cycloalkyl, $C_3$-$C_8$ cycloalkylalkyl, cyano, trifluoromethyl, difluoromethoxy, trifluoromethoxy, azido, —$NR^{11}SO_2R^{12}$, —$SO_2NR^{11}R^{13}$, —$C(O)R^{14}$, —$C(O)OR^{15}$, —$OC(O)R^{14}$, —$NR^{11}C(O)OR^{16}$, —$NR^{11}C(O)R^{14}$, —$C(O)NR^{11}R^{13}$, —$NR^{11}R^{13}$, —$NR^{11}C(O)NR^{11}R^{13}$, —$OR^{15}$, —$S(O)R^{12}$, —$SO_2R^{12}$, —$SR^{12}$, heterocyclyl and heterocyclylalkyl;

$A^1$, $A^2$, $A^3$, $A^4$ and $A^5$ are taken together to form a five-membered heteroaryl;

each $A^1$, $A^2$, $A^3$, $A^4$ and $A^5$ is independently O, N, S, C or CH; provided that at least one of $A^1$, $A^2$, $A^3$, $A^4$ and $A^5$ is a heteroatom selected from the group consisting of O, N, and S, and at least one of $A^1$, $A^2$, $A^3$, $A^4$ and $A^5$ is C or CH;

U is $C_1$-$C_3$ alkylene optionally substituted with up to three groups independently selected from the group consisting of halogen, cyano, oxo, —$OR^{15}$ and $C_1$-$C_3$alkyl; provided that U is attached to the five-membered heteroaryl through a carbon atom on the heteroaryl; and $R^F$ is hydrogen, halogen, cyano, nitro, trifluoromethyl, difluoromethyl, trifluoromethoxy, difluoromethoxy, $C_1$-$C_6$ alkyl, $C_3$-$C_6$ cycloalkyl, $C_4$-$C_6$ cycloalkylalkyl, heterocyclyl, heterocyclylalkyl, —$NR^1SO_2R^2$, —$SO_2NR^3R^1$, —$C(O)R^4$, —$C(O)OR^5$, —$NR^1C(O)OR^5$, $NR^1C(O)R^4$, —$C(O)NR^1R^3$, —$NR^1R^3$, —$NR^1C(O)NR^1R^3$, —$OR^5$, —$S(O)R^2$, —$SO_2R^2$, or —$SR^2$;

Q is a bond or $C_1$-$C_6$ alkylene, wherein said alkylene is unsubstituted or optionally substituted with up to three groups independently selected from the group consisting of oxo, halogen, $C_1$-$C_3$ alkyl, cyano, trifluoromethyl, difluoromethoxy, trifluoromethoxy, —$NR^{11}R^{13}$ and $OR^{15}$:

X is O or S;

Y and Z are independently 0, S, $NR^1$ or a bond;

$R^C$ is H, $C_1$-$C_6$ alkyl, $C_3$-$C_6$ cycloalkyl, —$SO_2NR^3R^1$, —$C(O)R^4$, —$C(O)OR^5$, $C(O)NR^1R^3$, or —$SO_2R^2$, wherein each said alkyl and cycloalkyl is unsubstituted or optionally substituted with up to five groups independently selected from the group consisting of oxo, halogen, cyano, azido and —$OR^{15}$;

$R^D$ is $C_1$-$C_8$ alkyl, $C_3$-$C_8$ cycloalkyl, aryl, arylalkyl, heteroaryl, heteroarylalkyl, heterocyclyl or heterocyclylalkyl, wherein each said alkyl, cycloalkyl, aryl, arylalkyl, heteroaryl, heteroarylalkyl, heterocyclyl and heterocyclylalkyl is unsubstituted or optionally substituted with up to five groups independently selected from the group consisting of the group consisting of oxo, halogen, cyano, —$OR^{15}$, —$NR^{11}R^{13}$, —$SO_2R^{12}$, —$SR^{12}$, trifluoromethyl, difluoromethoxy and trifluoromethoxy; and $R^E$ is $C_1$-$C_8$ alkyl, $C_3$-$C_8$ cycloalkyl, aryl, arylalkyl, heteroaryl, heteroarylalkyl, heterocyclyl or heterocyclylalkyl, wherein each said alkyl, cycloalkyl, aryl, arylalkyl, heteroaryl, heteroarylalkyl, heterocyclyl and heterocyclylalkyl is unsubstituted or optionally substituted with up to five groups independently selected from the group consisting of the group consisting of oxo, halogen, cyano, —$OR^{15}$, —$NR^{11}R^{13}$, —$SO_2R^{12}$, —$SR^{12}$, trifluoromethyl, difluoromethoxy and trifluoromethoxy;

or wherein $R^C$ and $R^D$ are together with Y, Q and the atoms to which they are attached to form a 4 to 10 membered heterocyclic ring which is optionally substituted with up to five groups independently selected from the group consisting of halogen, oxo, —$OR^{15}$, —$NR^{11}R^{13}$, —$SO_2R^{12}$, —$SR^{12}$, $C_1$-$C_6$ alkyl; $C_3$-$C_6$cycloalkyl, trifluoromethyl, difluoromethoxy, trifluoromethoxy, azido, aryl, heteroaryl, arylalkyl, heteroarylalkyl, heterocyclyl and heterocyclylalkyl;

or wherein $R^D$ and $R^E$ are taken together with Y, Z and the phosphorus atom to which they are attached to form a 4 to 10 membered heterocyclic ring which is optionally substituted with up to five groups independently selected from the group consisting of halogen, oxo, —OR$^{15}$, —NR$^{11}$R$^{13}$, —SO$_2$R$^{12}$, —SR$^{12}$, C$_1$-C$_6$alkyl, C$_1$-C$_6$cyclylalkyl, trifluoromethyl, difluoromethoxy, trifluoromethoxy, azido, aryl, heteroaryl, arylalkyl, heteroarylalkyl, heterocyclyl and heterocyclylalkyl;

wherein:

each R$^1$ is independently hydrogen, C$_1$-C$_6$alkyl or C$_3$-C$_6$cycloalkyl, wherein each said alkyl and cycloalkyl is unsubstituted or optionally substituted with up to five groups independently selected from the group consisting of oxo, halogen, cyano, azido and —OR$^{15}$;

each R$^2$ is independently C$_1$-C$_6$alkyl, C$_3$-C$_6$ cycloalkyl, aryl, arylalkyl, heteroaryl, heteroarylalkyl, heterocyclyl or heterocyclylalkyl, wherein each said alkyl, cycloalkyl, aryl, arylalkyl, heteroaryl, heteroarylalkyl, heterocyclyl and heterocyclylalkyl is unsubstituted or optionally substituted with up to five groups independently selected from the group consisting of oxo, halogen, cyano and —OR$^{15}$;

each R$^3$ is independently hydrogen, C$_1$-C$_6$alkyl, C$_2$-C$_6$ alkenyl, C$_2$-C$_6$ alkynyl, C$_3$-C$_8$ cycloalkyl, C$_3$-C$_8$ cycloalkylalkyl, heterocyclyl or heterocyclylalkyl, wherein each said alkyl, cycloalkyl, cycloalkylalkyl, heterocyclyl and heterocyclylalkyl is unsubstituted or optionally substituted with up to five groups independently selected from the group consisting of oxo, halogen, cyano, azido and —OR$^{15}$;

each R$^4$ is independently hydrogen, C$_1$-C$_6$ alkyl or C$_3$-C$_6$ cycloalkyl, wherein each said alkyl and cycloalkyl is unsubstituted or optionally substituted with up to five groups independently selected from the group consisting of oxo, halogen, cyano, azido and —OR$^{15}$; and each R$^5$ is hydrogen, C$_1$-C$_8$ alkyl, C$_2$-C$_8$ alkenyl, C$_2$-C$_8$ alkynyl, C$_3$-C$_8$ cycloalkyl, C$_3$-C$_8$ cycloalkylalkyl, heterocyclyl or heterocyclylalkyl, wherein each said alkyl, cycloalkyl, cycloalkylalkyl, heterocyclyl and heterocyclylalkyl is unsubstituted or optionally substituted with up to five groups independently selected from the group consisting of oxo, halogen, cyano and azido;

or wherein when R$^1$ and R$^2$ are attached to the same atom or are attached to adjacent atoms, R$^1$ and R$^2$ are together with the atom or the atoms to which they are attached to form a 4 to 10 membered heterocyclic ring which is optionally substituted with up to three groups independently selected from the group consisting of halogen, oxo, cyano, trifluoromethyl, difluoromethoxy, trifluoromethoxy, azido, heterocyclyl and heterocyclylalkyl;

or wherein when R$^1$ and R$^3$ are attached to the same atom or are attached to adjacent atoms, R$^1$ and R$^3$ are taken together with the atom or the atoms to which they are attached to form a 4 to 10 membered heterocyclic ring which is optionally substituted with up to three groups independently selected from the group consisting of halogen, oxo, cyano, trifluoromethyl, difluoromethoxy, trifluoromethoxy, azido, heterocyclyl and heterocyclylalkyl;

or wherein when R$^1$ and R$^4$ are attached to the same atom or are attached to adjacent atoms, R$^1$ and R$^4$ are taken together with the atom or the atoms to which they are attached to form a 4 to 10 membered heterocyclic ring which is optionally substituted with up to three groups independently selected from the group consisting of halogen, oxo, cyano, trifluoromethyl, difluoromethoxy, trifluoromethoxy, azido, heterocyclyl and heterocyclylalkyl;

or wherein when R$^1$ and R$^5$ are attached to the same atom or are attached to adjacent atoms, R$^1$ and R$^5$ are taken together with the atom or the atoms to which they are attached to form a 4 to 10 membered heterocyclic ring which is optionally substituted with up to three groups independently selected from the group consisting of halogen, oxo, cyano, trifluoromethyl, difluoromethoxy, trifluoromethoxy, azido, heterocyclyl and heterocyclylalkyl;

wherein:

each R$^{11}$ is independently hydrogen, C$_1$-C$_6$ alkyl or C$_3$-C$_6$cycloalkyl;

each R$^{12}$ is independently C$_1$-C$_6$ alkyl, C$_3$-C$_6$ cycloalkyl, aryl, arylalkyl, heteroaryl, heteroarylalkyl, heterocyclyl or heterocyclylalkyl;

each R$^{13}$ is independently hydrogen, C$_1$-C$_6$ alkyl, C$_2$-C$_6$ alkenyl, C$_2$-C$_6$ alkynyl, C$_3$-C$_8$ cycloalkyl, C$_3$-C$_8$ cycloalkylalkyl, heterocyclyl or heterocyclylalkyl;

each R$^{14}$ is independently hydrogen, C$_1$-C$_6$ alkyl or C$_3$-C$_6$ cycloalkyl;

each R$^{15}$ is hydrogen, C$_1$-C$_8$ alkyl, C$_2$-C$_8$ alkenyl, C$_2$-C$_8$ alkynyl, C$_3$-C$_8$ cycloalkyl, C$_3$-C$_8$ cycloalkylalkyl, heterocyclyl or heterocyclylalkyl; and each R$^{16}$ is independently C$_1$-C$_6$ alkyl, C$_3$-C$_6$ cycloalkyl, C$_3$-C$_8$ cycloalkylalkyl, heterocyclyl or heterocyclylalkyl;

wherein each heteroaryl is independently a monocyclic aromatic radical of 5 to 10 ring atoms or a polycyclic aromatic radical, containing one or more ring heteroatoms selected from nitrogen, oxygen and sulfur; and each heterocyclyl is independently a saturated or partially unsaturated cyclic radical of 3 to 8 ring atoms in which at least one ring atom is a heteroatom selected from nitrogen, oxygen and sulfur;

or a salt thereof.

3. The compound of claim 2, where the five-membered heteroaryl is selected from the group consisting of:

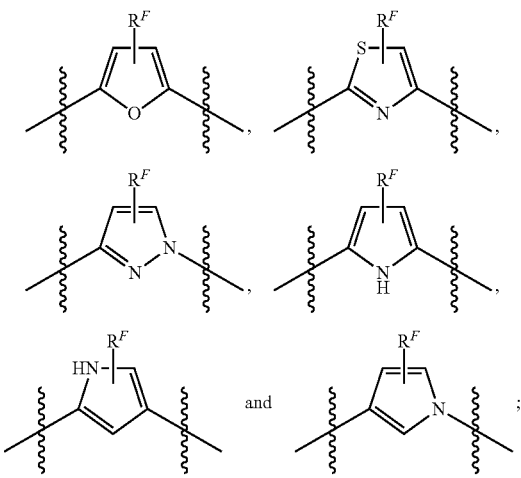

or a salt thereof.

4. The compound of claim 2, wherein the compound is of the formula (Aa-1):

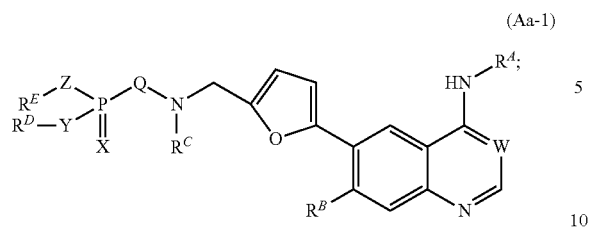

or a salt thereof.

5. The compound of claim 4, wherein the compound is of the formula (Aa-2):

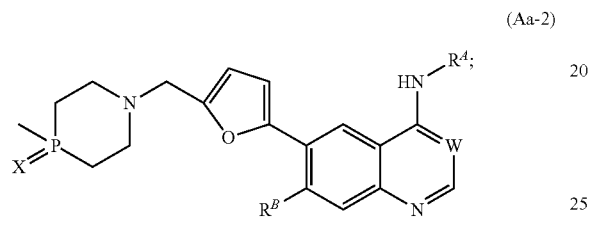

or a salt thereof.

6. The compound of claim 1, wherein the compound is of the formula (Ab)

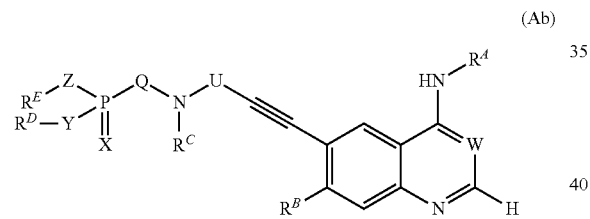

wherein U is $C_1$-$C_3$ alkylene optionally substituted with up to three groups independently selected from the group consisting of halogen, cyano, oxo, —$OR^{15}$ and $C_1$-$C_3$alkyl; or a salt thereof.

7. The compound of claim 6, wherein the compound is of the formula (Ab-1):

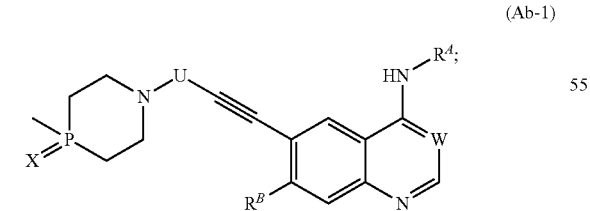

or a salt thereof.

8. The compound of claim 7, wherein U is methylene; or a salt thereof.

9. The compound of claim 1, wherein the compound is of the formula (Ac):

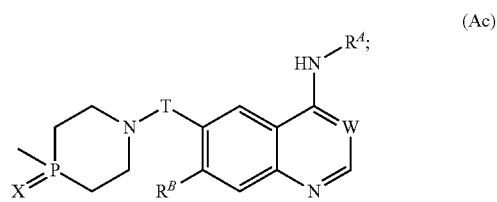

or a salt thereof.

10. The compound of claim 1, wherein $R^A$ is selected from the group consisting of:

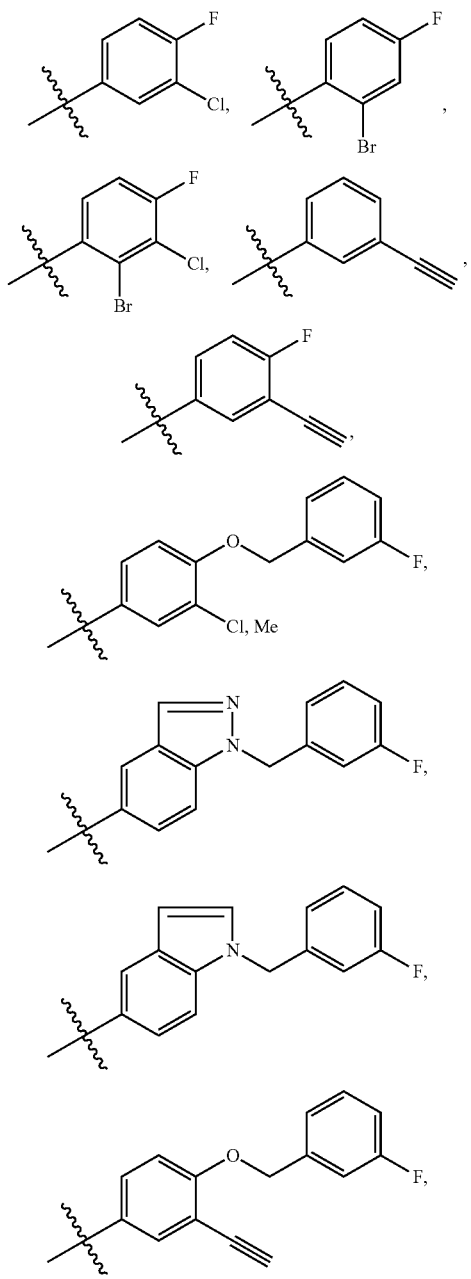

-continued

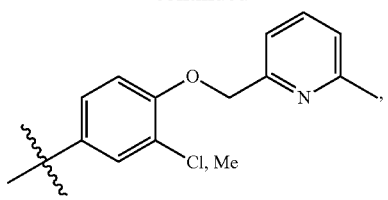

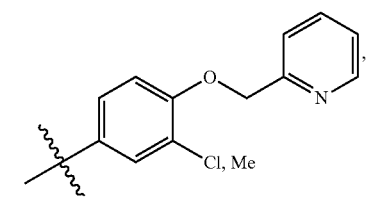

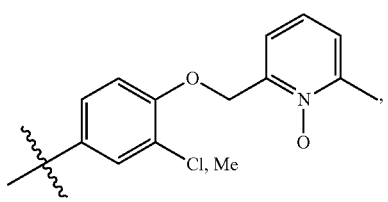

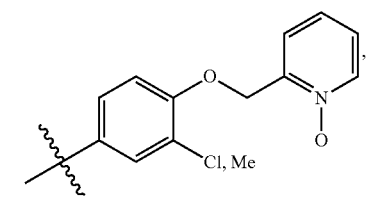

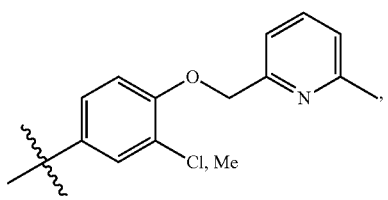

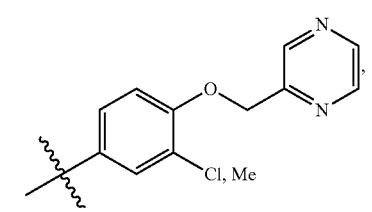

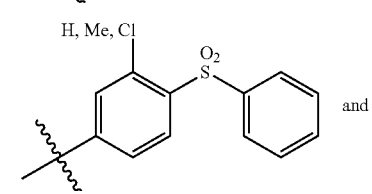

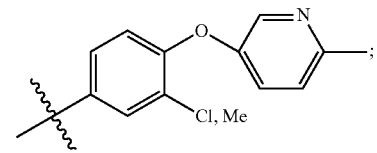

or a salt thereof.

11. The compound of claim 10, wherein $R^A$ is

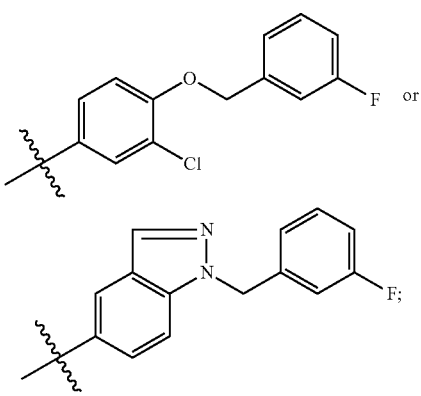

or a salt thereof.

12. The compound of claim 1, where $R^B$ is selected from the group consisting of hydrogen, halogen, and —OR⁵; or a salt thereof.

13. The compound of claim 12, wherein $R^B$ is hydrogen; or a salt thereof.

14. The compound of claim 1, wherein X is O; or a salt thereof.

15. A compound is selected from the group consisting of:
N-(3-chloro-4-(3-fluorobenzyloxyl)phenyl)-6-(5-((4-methyl-1,4-azaphosphino-1-yl)methyl)furan-2-yl) quinazolin-4-amine;
6-(5-((2-(dimethylphosphino)ethylaminoyl)methyl)furan-2-yl)-N-(4-(3-fluorobenzyloxy)-3-chlorophenyl) quinazolin-4-amine;
6-(5-(((dimethylphosphinoyl)methylamino)methyl)furan-2-yl)-N-(4-(3-fluorobenzyloxy)-3-chlorophenyl) quinazolin-4-amine;
N-(3-chloro-4-(3-fluorobenzyloxyl)phenyl)-6-(3-(4-methyl-1,4-azaphosphino-1-yl)prop-1-ynyl)quinazolin-4-amine;
N-(3-chloro-4-(3-fluorobenzyloxyl)phenyl)-6-(3-(4-methyl-1,4-azaphosphino-1-yl)propyl)quinazolin-4-amine;
dimethyl 2-((5-(4-(3-chloro-4-(3-fluorobenzyloxyl)phenylamino)quinazolin-6-yl)furan-2-yl)methylamino) ethylphosphonate;
N-(3-chloro-4-(3-fluorobenzyloxyl)phenyl)-6-(5-((2-(5,5-dimethyl-1,3,2-dioxaphosphino-2-yl)ethylamino) methyl)furan-2-yl)quinazolin-4-amine;
N-(3-chloro-4-(pyridin-2-ylmethoxy)phenyl)-6-(5-((4-methyl-1,4-azaphosphino-1-yl)methyl)furan-2-yl) quinazolin-4-amine;
N-(3-chloro-4-((6-methylpyridin-2-yl)methoxy)phenyl)-6-(5-((4-methyl-1,4-azaphosphino-1-yl)methyl)furan-2-yl)quinazolin-4-amine;
6-(3-(2-(dimethylphosphinoyl)ethylamino)prop-1-ynyl)-N-(4-(3-fluorobenzyloxy)-3-chlorophenyl)quinazolin-4-amine;
N-(4-(3-fluorobenzyloxy)-3-chlorophenyl)-6-((E)-3-(4-methyl-1,4-azaphosphino-1-yl)prop-1-enyl)quinazolin-4-amine;
N-(4-(6-methylpyridin-3-yloxy)-3-methylphenyl)-6-(5-((4-methyl-1,4-azaphosphinan-1-yl)methyl)furan-2-yl) quinazolin-4-amine;
N-(4-(3-fluorobenzyloxy)-3-chlorophenyl)-6-(5-((4-((dimethylphosphinoyl)-methyl)piperazin-1-yl)methyl)furan-2-yl)quinazolin-4-amine;

N-(4-(3-fluorobenzyloxy)-3-bromophenyl)-6-(5-((4-methyl-1,4-azaphosphino-1-yl)methyl)furan-2-yl)quinazolin-4-amine;

2-((2-chloro-4-(6-(5-((4-methyl-1,4-azaphosphino-1-yl)methyl)furan-2-yl)quinazolin-4-ylamino)phenoxy)methyl)pyridine 1-oxide;

N-(1-(3-fluorobenzyl)-1H-indazol-5-yl)-6-(5-((4-methyl-1,4-azaphosphino-1-yl)methyl)furan-2-yl)quinazolin-4-amine;

N-(3-chloro-4-(3-fluorobenzyloxyl)phenyl)-6-(5-((4-ethoxy-1,4-azaphosphino-1-yl)methyl)furan-2-yl)quinazolin-4-amine;

(R)-6-(5-((4-methyl-1,4-azaphosphino-1-yl)methyl)furan-2-yl)-N-(1-phenylethyl)quinazolin-4-amine;

N-(3-chloro-2-fluorophenyl)-6-(5-((4-methyl-1,4-azaphosphino-1-yl)methyl)furan-2-yl)quinazolin-4-amine;

N-(4-Bromo-2-fluorophenyl)-6-(5-((4-methyl-1,4-azaphosphino-1-yl)methyl)furan-2-yl)quinazolin-4-amine;

N-(4-Bromo-3-chloro-2-fluorophenyl)-6-(5-((4-methyl-1,4-azaphosphino-1-yl)methyl)furan-2-yl)quinazolin-4-amine;

N-(3-chloro-4-(pyrazin-2-ylmethoxy)phenyl)-6-(5-((4-methyl-1,4-azaphosphino-1-yl)methyl)furan-2-yl)quinazolin-4-amine;

N-(4-(3-fluorobenzyloxy)-3-ethynylphenyl)-6-(5-((4-methyl-1,4-azaphosphino-1-yl)methyl)furan-2-yl)quinazolin-4-amine;

2-((2-chloro-4-(6-(5-((4-methyl-1,4-azaphosphino-1-yl)methyl)furan-2-yl)quinazolin-4-ylamino)phenoxy)methyl)-6-methylpyridine 1-oxide;

6-(5-((2-(dimethylphosphinoyl)ethylamino)methyl)furan-2-yl)-N-(1-(3-fluorobenzyl)-1H-indazol-5-yl)quinazolin-4-amine;

2-(N-((5-(4-(1-(3-fluorobenzyl)-1H-indazol-5-ylamino)quinazolin-6-yl)furan-2-yl)methyl)-N-(2-(dimethylphosphino)ethyl)amino)ethane;

2-(N-((5-(4-(1-(3-fluorobenzyl)-1H-indazol-5-ylamino)quinazolin-6-yl)furan-2-yl)methyl)-N-(2-(dimethylphosphinoyl)ethyl)amino)ethanol; and N-(1-(3-fluorobenzyl)-1H-indazol-5-yl)-6-(3-(4-methyl-1,4-azaphosphino-1-yl)prop-1-ynyl)quinazolin-4-amine;

or a salt thereof.

16. The compound of claim 15, or a salt thereof, wherein the compound is:

N-(3-chloro-4-(3-fluorobenzyloxyl)phenyl)-6-(3-(4-methyl-1,4-azaphosphino-1-yl)prop-1-ynyl)quinazolin-4-amine.

17. A composition comprising a compound of claim 1, or a pharmaceutically acceptable salt thereof, and a pharmaceutically acceptable carrier.

18. A composition comprising a compound of claim 16, or a pharmaceutically acceptable salt thereof, and a pharmaceutically acceptable carrier.

19. A method of treating a Her2 positive breast cancer in a mammal, comprising administering to said mammal a therapeutically effective amount of a compound of claim 1, or a salt thereof.

20. The method of claim 19, wherein the mammal is human.

21. A method of treating a Her2 positive breast cancer in a mammal, comprising administering to said mammal a therapeutically effective amount of a compound of claim 16, or a salt thereof.

22. The method of claim 21, wherein the mammal is human.

23. A kit comprising a compound of claim 1, or a salt thereof.

24. A kit comprising a compound of claim 16, or a salt thereof.

* * * * *